(12) United States Patent
Patil et al.

(10) Patent No.: US 11,919,836 B2
(45) Date of Patent: *Mar. 5, 2024

(54) PRODRUGS OF FENCAMFAMINE

(71) Applicant: PRAXIS BIORESEARCH, LLC, Menlo Park, CA (US)

(72) Inventors: Sandeep Patil, Menlo Park, CA (US); Ron Bihovsky, Wynnewood, PA (US); Steven A Smith, San Jose, CA (US); Yuhua Ji, Palo Alto, CA (US); Valentino Stella, Lawrence, KS (US); Daniel D. Long, San Francisco, CA (US); Daniel Marquess, Half Moon Bay, CA (US)

(73) Assignee: Praxis Bioresearch, LLC, Menlo Park, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 16/847,988

(22) Filed: Apr. 14, 2020

(65) Prior Publication Data

US 2020/0399203 A1 Dec. 24, 2020

Related U.S. Application Data

(63) Continuation of application No. 15/758,466, filed as application No. PCT/US2016/051534 on Sep. 13, 2016, now Pat. No. 10,662,146.

(60) Provisional application No. 62/308,078, filed on Mar. 14, 2016, provisional application No. 62/298,267, filed on Feb. 22, 2016, provisional application No. 62/219,052, filed on Sep. 15, 2015.

(51) Int. Cl.
| | | |
|---|---|---|
| *C07C 271/24* | (2006.01) | |
| *A61K 9/00* | (2006.01) | |
| *A61K 47/10* | (2017.01) | |
| *A61K 47/26* | (2006.01) | |
| *A61K 47/38* | (2006.01) | |
| *A61K 47/54* | (2017.01) | |
| *A61K 47/64* | (2017.01) | |
| *C07C 233/06* | (2006.01) | |
| *C07C 237/04* | (2006.01) | |
| *C07C 237/20* | (2006.01) | |
| *C07C 237/22* | (2006.01) | |
| *C07C 271/56* | (2006.01) | |
| *C07K 5/062* | (2006.01) | |

(52) U.S. Cl.
CPC .......... *C07C 237/04* (2013.01); *A61K 9/0019* (2013.01); *A61K 9/0053* (2013.01); *A61K 9/0095* (2013.01); *A61K 47/10* (2013.01); *A61K 47/26* (2013.01); *A61K 47/38* (2013.01); *A61K 47/542* (2017.08); *A61K 47/64* (2017.08); *C07C 233/06* (2013.01); *C07C 237/20* (2013.01); *C07C 237/22* (2013.01); *C07C 271/24* (2013.01); *C07C 271/56* (2013.01); *C07K 5/06026* (2013.01); *C07K 5/06052* (2013.01); *C07B 2200/07* (2013.01); *C07C 2602/42* (2017.05)

(58) Field of Classification Search
CPC .......................... C07C 2602/42; C07C 271/24
See application file for complete search history.

(56) References Cited

U.S. PATENT DOCUMENTS

| | | |
|---|---|---|
| 3,536,707 A | 10/1970 | Shin |
| 5,760,049 A | 6/1998 | Viner |
| 5,824,684 A | 10/1998 | Viner |
| 5,900,418 A | 5/1999 | Viner |
| 5,908,850 A | 6/1999 | Zeitlin et al. |
| 5,916,903 A | 6/1999 | Viner |
| 5,981,549 A | 11/1999 | Viner |
| 6,166,032 A | 12/2000 | Viner |
| 6,261,537 B1 | 7/2001 | Klaveness et al. |
| 6,264,917 B1 | 7/2001 | Klaveness et al. |
| 6,331,289 B1 | 12/2001 | Klaveness et al. |
| 6,340,476 B1 | 1/2002 | Midha et al. |
| 6,555,136 B2 | 4/2003 | Midha |
| 6,680,047 B2 | 1/2004 | Klaveness et al. |
| 6,713,089 B1 | 3/2004 | Bertelsen et al. |
| 7,790,905 B2 | 9/2010 | Tawa et al. |
| 7,906,140 B2 | 3/2011 | Bromley et al. |
| 7,927,613 B2 | 4/2011 | Almarsson et al. |
| 7,964,607 B2 | 6/2011 | Verhoest et al. |
| 8,231,899 B2 | 7/2012 | Bertelsen et al. |
| 8,252,323 B2 | 8/2012 | Bromley et al. |
| 8,278,295 B2 | 10/2012 | Claffey et al. |
| 8,354,438 B2 | 1/2013 | Chez |
| 8,414,914 B2 | 4/2013 | Bromley et al. |

(Continued)

FOREIGN PATENT DOCUMENTS

| | | |
|---|---|---|
| CN | 103826633 A | 5/2014 |
| CN | 108348775 | 7/2018 |

(Continued)

OTHER PUBLICATIONS

Pubchem; CID 598419; "Fencamfamin propionyl"; create date 2005 (Year: 2005).*
Pubchem; CID 91752742; "Fencamfamin N-TFA"; create date Apr. 28, 2015 (Year: 2015).*
Drugbank; https://go.drugbank.com/drugs/DB01463; accessed Oct. 13, 2022 (Year: 2020).*
Communication Pursuant To Article 94(3) EPC dated Oct. 28, 2021 in European Patent Application No. 16 847 141.5.
Atkinson, A., et al., NCCN Practice Guidelines for Cancer-Related Fatigue; vol. 14, pp. 151-161, (2000).
Caromna, D. et al., Chiral Octahedral Phosphano-Oxazoline Iridium(III) Complexes as Catalysts in Asymmetric Cycloaddition Reactions ,Organometallics, vol. 32, pp. 1609-1619, (2013).

(Continued)

*Primary Examiner* — Timothy P Thomas
(74) *Attorney, Agent, or Firm* — Knobbe, Martens, Olson & Bear LLP

(57) ABSTRACT

Disclosed herein are pharmaceutical compositions comprising fencamfamine or fencamfamine related prodrug derivatives for targeted therapeutic applications and methods of synthesizing the compositions.

14 Claims, 22 Drawing Sheets

(56) References Cited

U.S. PATENT DOCUMENTS

| | | |
|---|---|---|
| 8,618,117 B2 | 12/2013 | Claffey et al. |
| 8,969,337 B2 | 3/2015 | Blumberg et al. |
| 10,662,146 B2 | 5/2020 | Patil |
| 2002/0058061 A1 | 5/2002 | Midha et al. |
| 2002/0102215 A1 | 8/2002 | Klaveness et al. |
| 2002/0102217 A1 | 8/2002 | Klaveness et al. |
| 2003/0170181 A1 | 9/2003 | Midha |
| 2003/0194439 A1 | 10/2003 | Midha et al. |
| 2004/0141922 A1 | 7/2004 | Klaveness et al. |
| 2005/0002865 A1 | 1/2005 | Klaveness et al. |
| 2005/0147668 A1 | 7/2005 | Bertelsen et al. |
| 2005/0281772 A1 | 12/2005 | Bromley et al. |
| 2006/0052428 A1 | 3/2006 | Chez |
| 2009/0030003 A1 | 1/2009 | Verhoest et al. |
| 2009/0325999 A1 | 12/2009 | Du |
| 2010/0190771 A1 | 7/2010 | Claffey et al. |
| 2011/0117184 A1 | 5/2011 | Bromley et al. |
| 2011/0207718 A1 | 8/2011 | Bird |
| 2011/0263526 A1 | 10/2011 | Satyam |
| 2012/0046232 A1 | 2/2012 | Kalivas et al. |
| 2012/0308644 A1 | 12/2012 | Bromley et al. |
| 2012/0329777 A1 | 12/2012 | Claffey et al. |
| 2013/0184265 A1 | 7/2013 | Blumberg et al. |
| 2013/0273162 A1 | 10/2013 | Li |
| 2013/0289019 A1 | 10/2013 | Chau |
| 2014/0073589 A1 | 3/2014 | Whomsley et al. |
| 2014/0088081 A1 | 3/2014 | Claffey et al. |
| 2014/0121193 A1 | 5/2014 | Katz et al. |
| 2014/0142140 A1 | 5/2014 | Bird |
| 2014/0243291 A1 | 8/2014 | Guenther et al. |
| 2014/0271835 A1 | 9/2014 | Wengner et al. |
| 2014/0364367 A1 | 12/2014 | Cotter |
| 2015/0064231 A1 | 3/2015 | Li |
| 2015/0246958 A1 | 9/2015 | Han |

FOREIGN PATENT DOCUMENTS

| | | |
|---|---|---|
| EP | 1185268 B1 | 8/2005 |
| EP | 3349853 | 7/2018 |
| GB | 913866 | 12/1962 |
| HK | 1258512 A | 11/2019 |
| JP | 6983161 | 12/2021 |
| WO | WO 2013/016668 | 1/2013 |
| WO | WO 2017/048720 A1 | 3/2017 |

OTHER PUBLICATIONS

Glaus et al., A qualitative study to explore the concept of fatigue/tiredness in cancer patients and in healthy individuals, Eur J cancer Care, pp. Jun. 5, 2 Suppl 8-23 (1996).

Holley, S. Cancer-Related Fatigue, Suffering a Different Fatigue, Cancer Practice, vol. 8, No. 2, pp. 87-95, (2000).

International Search Report & Written Opinion dated Dec. 2, 2016 in International Patent Application No. PCT/US2016/51534.

Novakov, I et al., An Improved Synthesis of N-(3-PHENYLBICYCLO[2. 2.1]-YL)-N-ETHYLAMINE Hydrochloride (Fencamfamine) Pharmaceutical Chemistry Journal vol. 45, No. 7, pp. 419-422, (2011).

Organic Syntheses, Coll. Vol. 4, p. 238 (1963) & Organic Syntheses, vol. 32, p. 41 (1952).

Portenoy et al, Management of Cancer Pain, Lancet, vol. 353, pp. 1695-1700 (1999).

Pubchem CID 598419, Created Mar. 27, 2005.

Praxis Bioresearch Awarded $1.5 Million Fast-Track SBIR Grant for Development of Novel Prodrug Stimulant with Abuse-Deterrent Properties, Published Aug. 7, 2018, BioSpace Accessible on the world wide web at <https://www.biospace.com/article/releases/praxis-bioresearch-awarded-1-5-million-fast-track-sbir-grant-for-development-of-novel-prodrug-stimulant-with-abuse-deterrent-properties/>.

Praxis Wins $1.5M NIH SBIR Grant toward Abuse-Deterrent Prodrug Stimulant, Genetic Engineering & Biotechnology News, Accessible on the world wide web at <https://www.genengnews.com/gen-news-highlights/praxis-wins-1-5m-nih-sbir-grant-toward-abuse-deterrent-prodrug-stimulant/81256115/?utm_medium=newsletter&utm_source=gen+daily+news+highlights&utm_content=01&utm_campaign=gen+daily+news+highlights_20180808&oly_enc_id=1461d5020134a9u&ajs_trait_oebid=9675b9130356b7s>, 2018.

Table of Contents of Remington: The Science and Practice of Pharmacy, Lippincott Williams & Wilkins; 20th edition, (2003).

Richardson A., et al, Fatigue in Ancer Patients: A Review of the Literature, European Journal of Cancer, vol. 4, pp. 20-32, (1995)/.

Simplico, A. et al. Prodrugs for Amines, Molecules, vol. 13 pp. 519-547, (2007).

Takenaka, N. et al., 2-Aminopyridinium Ions Activate Nitroalkenes through Hydrogen Bonding Organic Letters, vol. 9 pp. 2819-2822, (2007).

Wagner, L. et al., Fatigue and cancer: causes, prevalence and treatment approaches, British Journal of Cancer, vol. 94, pp. 822-828, (2004).

Weinstock, J. et al., Stereochemistry of a 3-Phenylnornane2-amine Journal of Organic Chemistry, vol. 26, pp. 5247-5249, (1961).

Phonphok et al., The inhibition of herpes simplex virus-1 syncytia formation by tromantadine and tromantadine analogs, XP002790050, retrieved from STN Database accession No. 1991:17086, Database CA [Online] Chemical Abstracts Service, Columbus, Ohio, US; 1989.

Extended European Search Report, dated Apr. 25, 2019, in European Application No. 16847141.5.

International Preliminary Report on Patentability, dated Mar. 20, 2018, in International Application No. PCT/US2016/051534.

Patil, S.T., et al., Novel prodrug PRX-P4-003, selectively activated by gut enzymes, may reduce the risk of iatrogenic addiction and abuse, Drug and Alcohol Dependence, vol. 186, pp. 159-166, 2018.

Praxis Bioresearch LLC, of Menlo Park, Calif., was awarded a $1.5 million fast-track Small Business Innovation Research grant from the National Institutes of Health to support development of PRX-P4-003, an abuse-deterrent dopamine norepinephrine reuptake inhibitor, p. 11, BioWorld, vol. 29, No. 15, Aug. 8, 2018, 15 pages.

Ding et al., Chiral drugs: comparison of the pharmacokinetics of [11C]d-threo and I-threo-methylphenidate in the human and baboon brain, Psychopharmacology (1997) 131:71-78.

Orange Book: Approved Drug Products with Therapeutic Equivalence Evaluations, downloaded Jul. 13, 2015 from https://www.accessdata.fda.gov/scripts/cder/ob/docs/patexclnew.cfm?Appl_No=021977&Product_No=001&table1=OB_Rx.

Office Action, dated Mar. 13, 2020, in Chinese Application No. 2016800633.

Office Action, dated Nov. 30, 2020, in Chinese Application No. 201680063327.0.

Office Action (Invitation to Correct Defects), dated Sep. 25, 2020, in EP Application No. 16847141.5.

Office Action, dated Aug. 17, 2020, in Japanese Application No. 2018-532535.

Notice of Allowance, dated Jan. 13, 2020, in U.S. Appl. No. 15/758,466.

File History of U.S. Appl. No. 15/758,466.

Da Luz Scheffer et al., Impaired dopamine metabolism is linked to fatigability in mice and fatigue in Parkinson's disease patients, Brain Communications, doi:10.1093/braincomms/fcab116, pp. 1-16, 2021.

Dobryakova, et al., The dopamine imbalance hypothesis of fatigue in multiple sclerosis and other neurological disorders, Frontier in Neurology, vol. 6, Article 52, 2015.

Roth, et al., Methylphenidate for Fatigue in Ambulatory Men with Prostate Cancer, Cancer, vol. 116, No. 21, pp. 5102-5110, doi:10.1002/cncr.25424, 2010.

Office Action received in Japanese Application No. 2018-532535 dated May 10, 2021.

Notice of Allowance received in Japanese Application No. 2018-532535 dated Oct. 25, 2021.

\* cited by examiner

PRODRUGS OF FENCAMFAMINE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD

The present disclosure relates to organic compounds, for example, prodrug derivatives of N-ethyl-3-phenylbicyclo[2.2.1]heptan-2-amine or any of its stereoisomers. More particularly disclosed herein are pharmaceutical prodrug compositions of N-ethyl-3-phenylbicyclo[2.2.1]heptan-2-amine, and methods of synthesizing the same.

BACKGROUND

Fencamfamine (Glucoenergan, Reactivan) is a stimulant which was developed in the 1960s as a treatment for reduced performance and rehabilitation from prolonged and debilitating diseases; treatment of depressive day-time fatigue, lack of concentration and lethargy (Brazil, European countries, South Africa, etc.).

SUMMARY

Some embodiments disclosed herein include compound of Formula (I) including forms such as stereoisomers, free forms, pharmaceutically acceptable salts or esters thereof, solvates, or combinations of such forms, wherein Y is defined herein.

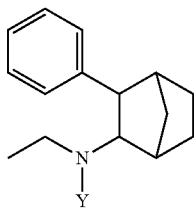

I

In some embodiments, a fencamfamine prodrug is provided. The fencamfamine prodrug comprises fencamfamine, and a Y moiety (defined below) conjugated to the fencamfamine. In some embodiments, the Y moiety is selected from the group consisting of —C(O)X and $(A)_n$; wherein X is selected from the group consisting of —$OR^1$, —$NHR^1$, —$NR^1R^5$, —$O(CR^2R^6)OR^3$, —$O(CR^2R^6)SR^3$, $O(CR^2R^6)NR^3$ and $R^4$; wherein $R^1$ is independently selected from optionally substituted $C_{1-16}$ alkyl, optionally substituted aryl, and optionally substituted cycloalkyl; wherein $R^2$, $R^5$, and $R^6$ are independently selected from hydrogen, optionally substituted $C_{1-6}$ alkyl; wherein $R^3$ is independently selected from optionally substituted $C_{1-26}$ alkanoyl; optionally substituted $C_{1-26}$ alkenoyl, optionally substituted $C_{1-26}$ alkynoyl; optionally substituted cycloalkanoyl; wherein $R^4$ is independently selected from optionally substituted $C_{1-26}$ alkyl; optionally substituted $C_{1-26}$ alkenyl, optionally substituted $C_{1-26}$ alkynyl; optionally substituted cycloalkyl; and wherein $(A)_n$ is a peptide unit formed with amino acid units wherein n is independently 1, 2, 3, or 4. In some embodiments, $R^1$ is selected from the group consisting of Me, Et, $^tBu$, 5-isopropyl-2-methylphenyl, and 2-isopropyl-5-methylphenyl. In some embodiments, $R^2$ and $R^6$ are independently selected from the group consisting of H and Me. In some embodiments, $R^2$ and $R^6$ are independently selected from the group consisting of H and Me, $R^3$ is independently selected from optionally substituted $C_{1-26}$ alkanoyl. In some embodiments, $R^2$ and $R^6$ are independently selected from the group consisting of H and Me, $R^3$ is independently selected from optionally substituted $C_{1-26}$ alkanoyl, and $R^3$ is from $C_{12}$ to $C_{18}$ in chain length. In some embodiments, $R^3$ is selected from the group consisting of acetyl, pivaloyl, butyryl, capryloyl, decanoyl, lauroyl, and stearoyl. In some embodiments, X is —$O(CHR^2)OR^3$. In some embodiments, when X is —$O(CHR^2)OR^3$, $R^2$ is independently selected from hydrogen, optionally substituted $C_{1-6}$ alkyl. In some embodiments, $R^4$ is —(CO)$CH_2CH_2COOH$. In some embodiments, $(A)_n$ is selected from the group consisting of Val, Lys, Gly, Gly-Gly, Val-Val, Gly-Ala, Phe, Phe-Phe, Ala-Gly, and Lys-Lys. In some embodiments, $R^3$ is selected from the group consisting of the acyl group of a fatty acid; C-12 fatty acid (dodecanoyl); C-16 fatty acid; C-18 fatty acid (octadecanoyl); C-20 fatty acid; C-22 fatty acid; C-24 fatty acid; and C-26 fatty acid.

In some embodiments, Y is selected from the group consisting of acyloxymethoxycarbonyl ($R^3C(O)OCH_2OCO$—); 1-acyloxyethoxycarbonyl ($R^3C(O)OCH(Me)OCO$—). X is —$O(CR^2R^6)OR^3$; $R^2$ and $R^6$ are independently selected from hydrogen, optionally substituted $C_{1-6}$alkyl; and $R^3$ is independently selected from optionally substituted $C_{1-26}$alkanoyl or optionally substituted $C_{1-26}$ alkenoyl. acyloxymethoxycarbonyl, ($R^3C(O)OCH_2OCO$—). In some embodiments, Y can be any addition to the fencamfamine structure, as depicted in any one of formula provided herein.

In some embodiments, a fencamfamine prodrug is provided. The fencamfamine prodrug comprises fencamfamine, a linker conjugated to the fencamfamine, and a fatty acid or at least one amino acid conjugated to the linker.

In some embodiments, a method for treating cancer-related fatigue is provided. Other targeted therapeutic applications include apathy in Alzheimer's Disease, major depression, attention deficit-hyperactivity disorder, etc. The method comprises administering to the subject an effective amount of any one or more of the compounds provided herein to a subject in need thereof.

In some embodiments, a prodrug composition comprising at least one conjugate of N-ethyl-3-phenylbicyclo[2.2.1]heptan-2-amine or any of its stereoisomers is provided. The conjugate is of the following formula (I):

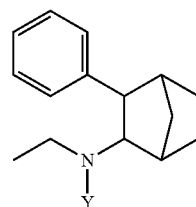

I wherein Y is selected from the group consisting of —C(O)X and $(A)_n$; wherein: X is selected from the group consisting of —$OR^1$, —$NHR^1$, —$NR^1R^5$, —$O(CR^2R^6)OR^3$, —$O(CR^2R^6)SR^3$, $O(CR^2R^6)NR^3$ and $R^4$, wherein $R^1$ is independently selected from optionally substituted $C_{1-16}$ alkyl, optionally substituted aryl, and optionally substituted cycloalkyl. Wherein $R^2$, $R^6$, and $R^6$ are independently selected from hydrogen, optionally substituted $C_{1-6}$ alkyl; wherein $R^3$ is independently selected from optionally substituted $C_{1-26}$ alkanoyl; optionally substituted $C_{1-26}$ alkenoyl, optionally substituted $C_{1-26}$ alkynoyl; optionally substituted cycloalkanoyl; wherein $R^4$ is independently selected from optionally substituted $C_{1-26}$ alkyl; optionally substituted $C_{1-26}$ alkenyl, optionally substituted $C_{1-26}$ alkynyl; optionally substituted cycloalkyl; and wherein $(A)_n$ is a peptide unit formed with amino acid units wherein n is independently 1, 2, 3, or 4.

Some embodiments disclosed herein relate to methods for treating cancer-related fatigue. in a mammal, comprising administering to the mammal an effective amount of one or more compounds of Formula (I) including forms such as stereoisomers, free forms, or a pharmaceutically acceptable salt thereof, or a pharmaceutical composition that includes one or more compounds of Formula (I) including forms such as stereoisomers, free forms, or a pharmaceutically acceptable salt thereof. Other embodiments described herein relate to using one or more compounds of Formula (I) including forms such as stereoisomers, free forms, or a pharmaceutically acceptable salt thereof, in the manufacture of a medicament for treatment of cancer-related fatigue. These and other embodiments are described in greater detail below.

DETAILED DESCRIPTION

Figure 1:
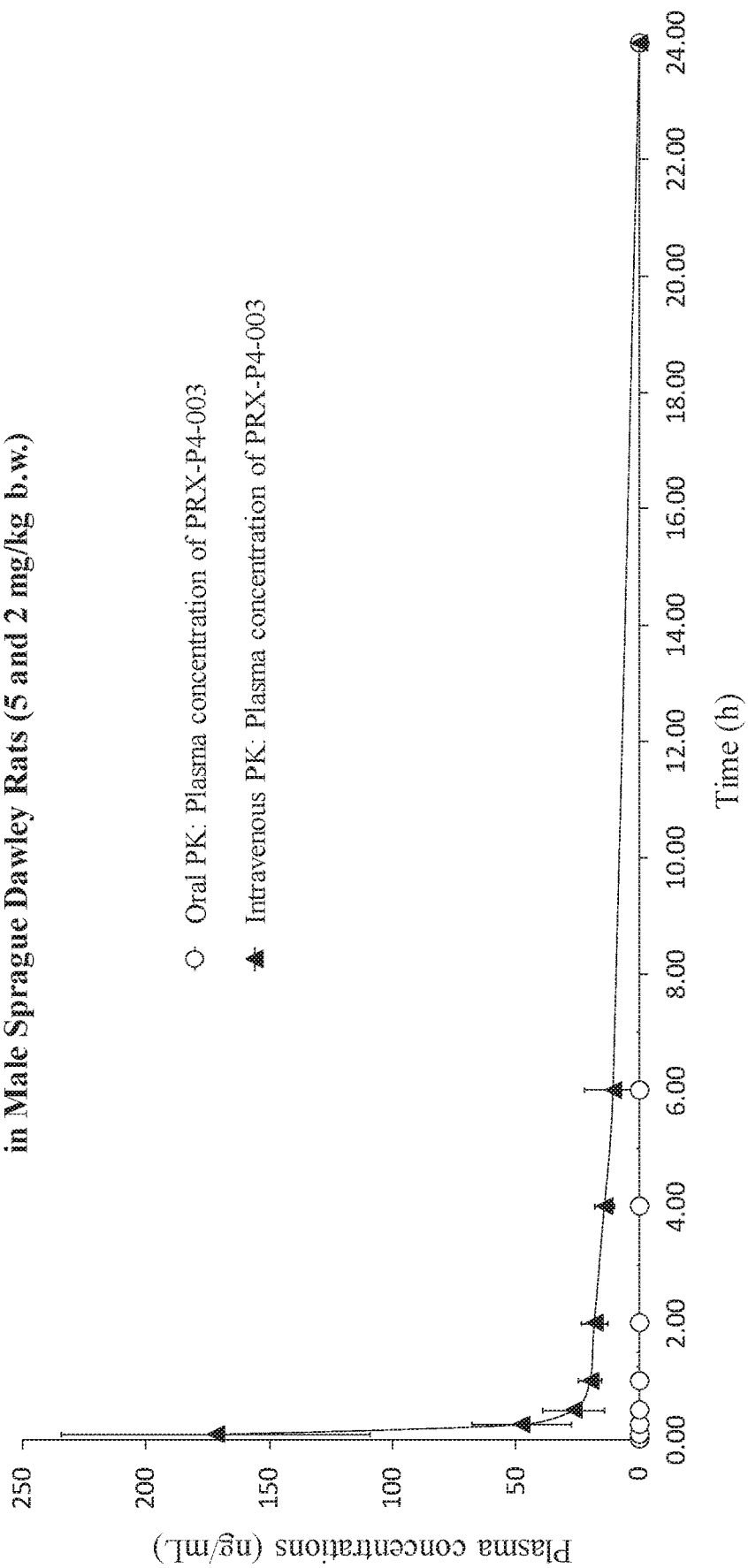
FIG. 1 depicts a set of comparative data of single dose oral and intravenous PK Study of PRX-P4-003.

The following description and examples illustrate various embodiments of the present disclosure in detail. Those of skill in the art will recognize that there are numerous variations and modifications of this disclosure that are encompassed by its scope. Accordingly, the description of the disclosed embodiment should not be deemed to limit the scope of the present disclosure.

Cancer-related fatigue (CRF) is a widespread adverse symptom related to cancer and cancer therapy. In a recent study, cancer patients reported that fatigue is the most distressing symptom associated with their cancer and cancer treatment (Richardson et al, 1995). CRF is a multicausal, multidimensional, and complex disturbance and hence is difficult to describe for patients, their families and even for health care providers (Portenoy et al, 1999). CRF can be best defined as an unusual and persistent sense of tiredness that can occur with cancer and cancer therapy (Atkinson et al, 2000). CRF may affect both physical and mental capacity and is unrelieved by rest. It is more severe, more energy draining, longer lasting and more unrelenting than other forms of fatigue (Glaus et al, 1996). CRF interferes with usual functioning and has a devastating effect on almost all aspects of patients' lives. It has a pervasive effect on motivation. Additionally, attending and completing a task becomes difficult. The most unusual characteristic of CRF is that it is unrelieved by rest or additional sleep (Holly, 2000). Most of the current pharmacological and non-pharmacological treatments offered by health care professionals are based on anecdotal evidence.

As noted above, fencamfamine (Glucoenergan, Reactivan) is a stimulant which was developed by E Merck in the 1960s. Until recently there have been reports that fencamfamine was still rarely used for treating depressive day-time fatigue, lack of concentration and lethargy, particularly in individuals who have chronic medical conditions, although its favorable safety profile makes it the most suitable drug in some cases. Fencamfamine increases drive and mental alertness and an elevation of mood and a general feeling of well-being.

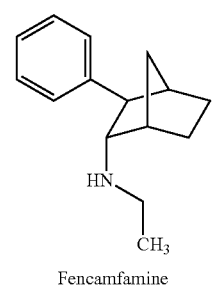 [SMILES: CCNC1C2CCC(C2)C1c1ccccc1]

Fencamfamine

Fencamfamine acts as an indirect dopamine agonist. The drug seems to inhibit the dopamine transporter (DAT) that removes dopamine from the synapses. This inhibition of DAT blocks the reuptake of dopamine and norepinephrine into the presynaptic neuron, increasing the amount of dopamine in the synapse. Also unlike amphetamines, fencamfamine does not appear to inhibit the action of monoamine oxidase enzymes and so is somewhat safer.

Due to its efficacy and extensive use in treating fatigue-related conditions fencamfamine could provide a pharmacological approach to treat CRF. In some embodiments provided herein, prodrug compositions of fencamfamine can provide a treatment for CRF while avoiding and/or reducing the drug-abuse profile but still providing the ability to dose via routine administration routes, e.g. oral.

In some embodiments, prodrug versions of fencamfamine allow for greater amounts of fencamfamine to be present in the plasma of the subject. In some embodiments, it allows for greater amounts of fencamfamine to be present in the plasma of the subject from oral administration of the prodrug to the subject.

In some embodiments, prodrug versions of fencamfamine allow for a particular isomer of fencamfamine to be provided to the subject.

The present disclosure provides derivatives and/or combinations thereof of fencamfamine (or N-ethyl-3-phenylbicyclo[2.2.1]heptan-2-amine) in prodrug form (including particular isomers thereof). In some embodiments, the fencamfamine is conjugated to at least one group Y as defined below (which may or may not be cleavable) such as but not limited to amides, acyloxyalkoxycarbonyl moieties or derivatives thereof, which are novel prodrug compositions and/or conjugates of N-ethyl-3-phenylbicyclo[2.2.1] heptan-2-amine. In some embodiments, a blocker and linker work together to form the prodrug, and thus, there is no necessary distinction between the two in terms of functional aspects for each embodiment. Thus, in some embodiments, the designation of linker and blocking moiety is a short hand to describe structural aspects, rather than functional aspects. In some embodiments, the group Y forms the prodrug.

In some embodiments, the prodrugs provided herein allow for a reduced risk of abuse or addiction by a user or patient. In some embodiments, this can be achieved by providing a release profile such that there is only an adequate amount of the active compound if the prodrug is taken orally. However, when the prodrug is taken by IV, it is not broken down into its active form in a substantial amount in the subject. With this release aspect, a subject's ability to receive, via IV, a large amount of the active form of the molecule is reduced (as taking a large amount of the prodrug via IV does not necessarily result in an increase of the active in the plasma levels, for various embodiments). Some exemplary embodiments of such prodrugs include PRX-P5-006 and PRX-P4-003 (which include a (−) isomer of fencamfamine). In some embodiments, the composition is one in which a fencamfamine is bonded to an adequately sized fatty acid (such as C-12 (dodecanoic acid) or C-18 (octadecanoic acid)). In some embodiments, linkage is via an appropriate Y moiety, such as acyloxymethoxycarbonyl ($R^3C(O)OCH_2OCO-$) or 1-acyloxyethoxycarbonyl ($R^3C(O)OCH(Me)OCO-$). In some embodiments, the composition is one represented by Formula (I) in which X is $-O(CR^2R^6)OR^3$; $R^2$ and $R^6$ are independently selected from hydrogen, optionally substituted $C_{1-6}$alkyl; and $R^3$ is independently selected from optionally substituted $C_{1-26}$ alkanoyl or optionally substituted $C_{1-26}$ alkenoyl.

In some embodiments, the prodrug composition provided herein allows for an increase in a total amount of exposure of an active form of the drug in the subject's plasma. Thus, in some embodiments, the prodrug described herein as PRX-P6-011 (which includes the (+) isomer of fencamfamine) can be used to provide a higher level of the active form of the drug over a desired time period. Such embodiments need not have the above noted IV vs oral selective activation aspects.

In some embodiments, the prodrug can have the (+) or (−) isomer of fencamfamine; however, as shown by the data provided herein, the type of Y group employed for the (+) or (−) isomers can vary and change the properties of the prodrug. Thus, various fencamfamine isomer prodrugs can have further unique characteristics and/or components, as outlined herein.

Thus, in some embodiments, prodrugs are provided that delay the time in which the active drug (fencamfamine) is made available to the brain (or within the plasma). In some embodiments, prodrugs are provided that allow for higher levels of the active drug to be present in the plasma.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there is a plurality of definitions for a term herein, those in this section prevail unless stated otherwise.

The use of the term "N-ethyl-3-phenylbicyclo[2.2.1]heptan-2-amine" herein is meant to include any of the stereoisomer forms of N-ethyl-3-phenylbicyclo[2.2.1]heptan-2-amine, including the four stereoisomers: (1S,2S,3R,4R)—N-ethyl-3-phenylbicyclo[2.2.1]heptan-2-amine, (1R,2R,3S,4S)—N-ethyl-3-phenylbicyclo[2.2.1]heptan-2-amine, (1R,2S,3R,4S)—N-ethyl-3-phenylbicyclo[2.2.1]heptan-2-amine and (1S,2R,3S,4R)—N-ethyl-3-phenylbicyclo[2.2.1]heptan-2-amine and the salts and derivatives thereof. The term "N-ethyl-3-phenylbicyclo[2.2.1]heptan-2-amine" includes all salt forms. N-ethyl-3-phenylbicyclo[2.2.1]heptan-2-amine is also known by its trade name Fencamfamine®, Glucoenergan®, and Reactivan® (E Merck, Germany). The N-ethyl-3-phenylbicyclo[2.2.1]heptan-2-amine used in the present disclosure can be any stereoisomer of N-ethyl-3-phenylbicyclo[2.2.1]heptan-2-amine, including, but not limited to, (1S,2S,3R,4R)—N-ethyl-3-phenylbicyclo[2.2.1]heptan-2-amine, (1R,2R,3S,4S)—N-ethyl-3-phenylbicyclo[2.2.1]heptan-2-amine, (1R,2S,3R,4S)—N-ethyl-3-phenylbicyclo[2.2.1]heptan-2-amine and (1S,2R,3S,4R)—N-ethyl-3-phenylbicyclo[2.2.1]heptan-2-amine. In some embodiments, the N-ethyl-3-phenylbicyclo[2.2.1]heptan-2-amine can be a mixture of two or more racemates. Depending on the chemical structure of the Y group from acyloxyalkoxycarbonyl linked fatty acids, and thiols as well as the chiral composition of the N-ethyl-3-phenylbicyclo[2.2.1]heptan-2-amine to which they are attached, the resulting prodrug conjugates can be optically active mixtures of isomers, racemic mixtures, single isomers or combinations thereof. The various isomers of fencamfamine are depicted below.

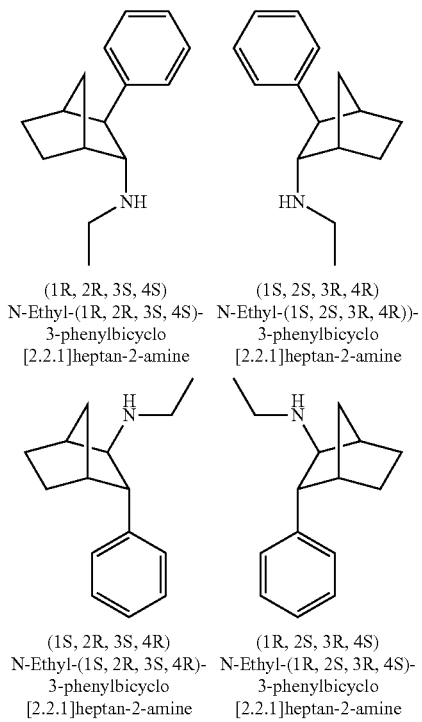

(1R, 2R, 3S, 4S)
N-Ethyl-(1R, 2R, 3S, 4S)-
3-phenylbicyclo
[2.2.1]heptan-2-amine (1S, 2S, 3R, 4R)
N-Ethyl-(1S, 2S, 3R, 4R))-
3-phenylbicyclo
[2.2.1]heptan-2-amine (1S, 2R, 3S, 4R)
N-Ethyl-(1S, 2R, 3S, 4R)-
3-phenylbicyclo
[2.2.1]heptan-2-amine (1R, 2S, 3R, 4S)
N-Ethyl-(1R, 2S, 3R, 4S)-
3-phenylbicyclo
[2.2.1]heptan-2-amine RX-002 consists of racemic fencamfamine. The (+)- and (−)-isomers designate the optical rotation of the resolved fencamfamine enantiomers. As used herein, the two Exo-phenyl,endo-amino isomers are PRX 002 (+) and (−). One of skill in the art can obtain the desired (+) or (−) enantiomers by chromatography on a chiral column (as outlined in the examples below). The (+)-enantiomer of fencamfamine is (1S,2S,3R,4R)—N-Ethyl-3-phenylbicyclo[2.2.1]heptan-2-amine. The (−)-enantiomer of fencamfamine is (1R,2R,3S,4S)—N-Ethyl-3-phenylbicyclo[2.2.1]heptan-2-amine. In some embodiments, the (1R,2R,3S,4S)-compound can be used as any of the prodrug compounds provided herein (including any of the methods). In some embodiments, the (1S,2S,3R,4R)-compound can be used as any of the prodrug compounds provided herein (including any of the methods). In some embodiments, the (1R,2R,3S,4S)-compound can be used as any of the prodrug compounds provided herein (including any of the methods). In some embodiments, the (1S,2S,3R,4R)-compound can be used as any of the prodrug compounds provided herein (including any of the methods). Thus, any one of the above isomers can be used as the active in any one of the prodrug arrangements provided herein. In some embodiments, it is one or more of the Exo isomers noted above. In some embodiments, it is one or more of the Endo isomers noted above.

As used herein, any "R" group(s) such as, without limitation, $R^1$, $R^2$, $R^3$, $R^4$, $R^6$, and $R^6$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

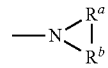

In addition, if two "R" groups are described as being "taken together" with the atom(s) to which they are attached to form a ring as an alternative, the R groups may not be limited to the variables or substituents defined previously.

As used herein, "alkyl" refers to a straight or branched hydrocarbon chain that comprises a fully saturated (no double or triple bonds) hydrocarbon group. The alkyl group may have 1 to 26 carbon atoms (whenever it appears herein, a numerical range such as "1 to 26" refers to each integer in the given range; e.g., "1 to 26 carbon atoms" means that the alkyl group may consist of 1 carbon atom, 2 carbon atoms, 3 carbon atoms, etc., up to and including 26 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from methyl, ethyl, propyl, iso-propyl, n-butyl, iso-butyl, sec-butyl, and t-butyl, pentyl (straight and branched) and hexyl (straight and branched). Typical alkyl groups include, but are in no way limited to, methyl, ethyl, propyl, isopropyl, butyl, isobutyl, tertiary butyl, pentyl (straight and branched) and hexyl (straight and branched). The alkyl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "aryl" refers to a carbocyclic (all carbon) mono-cyclic or multi-cyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "alkanoyl" used herein refers to a "carbonyl" substituted with an "alkyl" group, the "alkanoyl" group is covalently bonded to the parent molecule through the carbon of the "carbonyl" group.

As used herein, "cycloalkanoyl" used herein refers to a "carbonyl" substituted with an "cycloalkyl" group, the "alkanoyl" group is covalently bonded to the parent molecule through the carbon of the "carbonyl" group.

As used herein, "alkenoyl" used herein refers to a "carbonyl" substituted with an "alkenyl" group, the "alkenoyl" group is covalently bonded to the parent molecule through the carbon of the "carbonyl" group.

As used herein, "alkynoyl" used herein refers to a "carbonyl" substituted with an "alkynyl" group, the "alkynoyl"

group is covalently bonded to the parent molecule through the carbon of the "carbonyl" group.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "C2-4 alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

As used herein, the term "prodrug" generally refers to a compound, which is pharmaceutically acceptable and upon administration is converted to a desired active compound, here fencamfamine. In some embodiments, the prodrug can be therapeutically inactive until cleaved to release the active compound. The prodrug will contain an "active" component, in this case fencamfamine, and a Y moiety as defined. Removal of some or all of the Y moiety will convert the prodrug from an inactive form to an active drug. This is done in the body by a chemical or biological reaction.

In the present disclosure, the prodrug is a conjugate of at least one drug, N-ethyl-3-phenylbicyclo[2.2.1]heptan-2-amine, and an additional Y moiety that can be removed and/or altered within the body. Thus, the conjugates of the present disclosure are prodrugs and the prodrugs of the present disclosure are conjugates. In some embodiments, the Y moiety can include an acyl group from a carboxylic acid such as a fatty acid, for example. In some embodiments, the Y moiety can be one or more amino acids, such as one, two, or three valines bonded together as a peptide.

While not a necessary term for describing various embodiments provided here (such as when explicit structures are shown for the Y moiety, etc.), the term "blocking moiety" denotes a chemical moiety, which may be removed from a larger prodrug, but when present, reduces and/or alters a property of the active component of the prodrug.

While not a necessary term for describing various embodiments provided here (such as when explicit structures are shown for the Y moiety, etc.), the term "linker" denotes a chemical moiety, which may link the blocking moiety to the active in a prodrug.

The Y moiety itself may be removable from the prodrug, or the Y moiety (or a part thereof) can remain associated with the active, after the removal of at least part of the prodrug.

The term "active" is used herein to refer to fencamfamine, and/or N-ethyl-3-phenylbicyclo[2.2.1]heptan-2-amine (or a particular isomer or collection thereof) to distinguish it from the prodrug form. Thus, it does not necessarily denote any other metabolite or derivative from fencamfamine (such as whether or not the fencamfamine is altered further when administered to a subject). The term "active" also encompasses the prodrug compounds that have been activated by proper exposure in vivo and/or in vitro. Thus, the active form of a prodrug may include fencamfamine that is still bonded to some subpart of the prodrug form (for example, whatever remains after the body has removed an adequate section of the Y moiety). The "activated prodrug" denotes the form of the molecule after it has been processed by the body and is in an active form of fencamfamine. In some embodiments, any of the four isomers of fencamfamine noted above can be used in the prodrug, and thus, result in the isomer for the activated prodrug.

In some embodiments, the prodrug can be easier to administer or process than the parent or active form of the drug. They may, for instance, be more bioavailable by oral administration whereas the active drug is not. The prodrug may also have improved solubility in pharmaceutical compositions over the active drug. In some embodiments, a prodrug is an N-ethyl-3-phenylbicyclo[2.2.1]heptan-2-amine conjugate that is metabolized to reveal the active moiety. In some embodiments, upon in vivo administration, a prodrug is chemically converted to the biologically, pharmaceutically or therapeutically more active form of the compound. In some embodiments, a prodrug is enzymatically metabolized by one or more steps or processes to the biologically, pharmaceutically or therapeutically active form of the compound. In some embodiments, to produce a prodrug, a pharmaceutically active compound is modified such that the active compound will be regenerated upon in vivo administration. In some embodiments, the prodrug is designed to alter the metabolism or the transport characteristics of a drug in certain embodiments, to mask side-effects or toxicity, to improve bioavailability and/or water solubility, to improve the flavor of a drug, to reduce the risk of abuse, or to alter other characteristics or properties of a drug in other discrete embodiments.

In some embodiments, the present disclosure provides at least one prodrug composition comprising at least an active drug conjugated to a blocking moiety and/or linker to form a conjugated molecule or a "conjugate". The conjugate may comprise at least one N-ethyl-3-phenylbicyclo[2.2.1]heptan-2-amine and at least one blocking moiety, such as an alcohol, amine, acyl group from acyloxyalkoxycarbonyl bonded fatty acids, thiol, or derivatives thereof. In some embodiments, the conjugate comprises at least one linker, linking the active drug to the blocking moiety. In some embodiments, the linker chemically bonds the N-ethyl-3-phenylbicyclo[2.2.1]heptan-2-amine to the alcohol, amine, or thiol via one or more covalent bonds. In some embodiments, the linker serves as part of the blocking moiety and/or is the same as the blocking moiety. In some embodiments, the linker includes an acyl group from a carboxylic acid.

The term "cancer-related fatigue" encompasses any unusual and persistent sense of tiredness that can occur with cancer and cancer therapy.

The term "supportive oncology" encompasses the treatment of a subject receiving or a subject that has received a cancer therapy.

As used herein, phrases such as "decreased," "reduced," "diminished" or "lowered" is meant to include at least a 10% change in pharmacological activity with greater percentage changes being preferred for reduction in abuse potential and overdose potential. For instance, the change may also be greater than 25%, 35%, 45%, 55%, 65%, 75%, 85%, 95%, 96%, 97%, 98%, 99%, or increments therein.

Unless otherwise specified, the term "naturally occurring" refers to occurring in nature, for example, in bacteria or in a mammal (e.g., a human).

The term "abuse" encompasses uses that are inconsistent with a doctor's or manufacturer's instructions.

As used herein, "in a manner inconsistent with the manufacturer's instructions" or similar expression is meant to include, but is not limited to, consuming amounts greater than amounts described on the drug label or ordered by a licensed physician, and/or altering by any means (e.g., crushing, breaking, melting, or separating) the dosage form such that the composition may be injected, inhaled or smoked instead of being taken orally (or according to the instructions).

Depending on the blocking moiety and the alcohol, amine, acyl group from a carboxylic acid, and thiol conjugated to N-ethyl-3-phenylbicyclo[2.2.1]heptan-2-amine or derivative thereof, the at least one prodrug formed can be either a neutral (uncharged), a free acid, a free base or a pharmaceutically acceptable anionic or cationic salt form or salt mixtures with any ratio between positive and negative components. These anionic salt forms can include, but are not limited to, for example, acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, l-lactate, d,l-lactate, d,l-malate, l-malate, mesylate, pamoate, phosphate, succinate, sulfate, bisulfate, d-tartrate, l-tartrate, d,l-tartrate, meso-tartrate, benzoate, gluceptate, d-glucuronate, hybenzate, isethionate, malonate, methylsufate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, or undecylenate. The cationic salt forms can include, but are not limited to, for example, sodium, potassium, calcium, magnesium, zinc, aluminum, lithium, cholinate, lysinium, ammonium, or tromethamine.

The term "pharmaceutically acceptable carriers" includes, but is not limited to, 0.01-0.1M and preferably 0.05M phosphate buffer, or in another embodiment 0.8% saline. Additionally, such pharmaceutically acceptable carriers may be in another embodiment aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In some embodiments, the carrier can be a) 10% PEG 400 (v/v)+30% (v/v) HPβCD, 50% w/v+60% (v/v) Sterile Water for Injection or b) 0.1% (v/v) Tween 80+0.5% (w/v) Carboxymethylcellulose in water.

The term "subject" refers to a mammal, such as humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, and cats, avian species, such as chickens, turkeys, and songbirds. The subject can be, for example, a child, such as an adolescent, or an adult.

The term "treatment" refers to any treatment of a pathologic condition in a subject, such as a mammal, particularly a human, and includes: (i) preventing and/or reducing the risk of a pathologic condition from occurring in a subject which may be predisposed to the condition but has not yet been diagnosed with the condition and, accordingly, the treatment constitutes prophylactic treatment for the disease condition; (ii) inhibiting and/or reducing the speed of development of the pathologic condition, e.g., arresting its development; (iii) relieving the pathologic condition, e.g., causing regression of the pathologic condition; or (iv) relieving the conditions mediated by the pathologic condition and/or symptoms of the pathologic condition. Treatment to subjects who have previously and/or are currently, and/or are about to receive a cancer therapy are contemplated herein.

The term "therapeutically effective amount" refers to that amount of a compound of the invention that is sufficient to effect treatment, when administered to a subject in need of such treatment. The therapeutically effective amount will vary depending upon the subject and disease condition being treated, the weight and age of the subject, the severity of the disease condition, the manner of administration and the like, which can readily be determined by one of ordinary skill in the art.

Without being limited to the following theory, some of the embodiments of the prodrugs/conjugates provided herein undergo enzyme hydrolysis of the ester bond in vivo, which subsequently leads to a cascade reaction resulting in provision of of N-ethyl-3-phenylbicyclo[2.2.1]heptan-2-amine and the respective, metabolites thereof and/or derivatives and/or components thereof. The blocking moieties, such as alcohols, amines, amino acids, acyl group from acyloxyalkoxycarbonyl ((acyloxy)alkyl ester) bonded fatty acids, thiols, or derivatives thereof, of the present disclosure are non-toxic or have very low toxicity at the given dose levels and are preferably known drugs, natural products, metabolites, or GRAS (Generally Recognized As Safe) compounds (e.g., preservatives, dyes, flavors, etc.) or non-toxic mimetics or derivatives thereof.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

In some embodiments, a fencamfamine prodrug is provided. In some embodiments, the prodrug comprises fencamfamine, a Y group conjugated to the fencamfamine, such as a) a fatty acid or b) at least one amino acid. In some embodiments, the prodrug comprises fencamfamine directly bonded to an amino acid or dipeptide via the amino acid or dipeptide amide bond In some embodiments, the Y moiety comprises 1-Acyloxyethoxycarbonyl, ($R^3C(O)OCH(Me)OCO$—). In some embodiments, this fencamfamine prodrug comprises a fatty acid. In some embodiments, the fencamfamine is the 002(−) isomer.

In some embodiments, the Y group comprises acyloxymethoxycarbonyl, ($R^3C(O)OCH_2OCO$—). In some embodiments, the fencamfamine is the PRX-002 (−) isomer or PRX-002 (+) isomer.

In some embodiments, the fencamfamine prodrug comprises an amino acid or dipeptide directly bonded to fencamfamine via an amide bond. In some embodiments, the at least one amino acid comprises at least two amino acids as a peptide. In some embodiments, the at least two amino acids is a valine bonded to a valine via a peptide bond. In some embodiments, the fencamfamine is the PRX-002 (+) isomer.

In some embodiments, the fencamfamine component within the prodrug comprises any one or more of the isomers of fencamfamine as provided herein. In some embodiments, the fencamfamine comprises 1, 2, 3, or 4 of the isomers of fencamfamine. In some embodiments, the fencamfamine is only one of the isomers In some embodiments the the fatty acid is at least C-12 in length. In some embodiments, the fatty acid is at least C-16 in length. In some embodiments, the fatty acid is at least C-18 in length. In some embodiments, the fatty acid is an octadecanoic acid. In some embodiments, the fatty acid is at least C-20 in length. In some embodiments, the fatty acid is at least C-22 in length. In some embodiments, the fatty acid is at least C-24 in length. In some embodiments, the fatty acid is at least C-26 in length.

In some embodiments, a compound is provided having Formula (I):

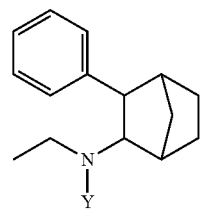

or a stereoisomer, a pharmaceutically acceptable salt, or solvate thereof, wherein Y is selected from the group consisting of —C(O)X and $(A)_n$;
wherein X is selected from the group consisting of —$OR^1$, —$NHR^1$, —$NR^1R^5$, —$O(CR^2R^6)OR^3$, —$O(CR^2R^6)SR^3$, $O(CR^2R^6)NR^3$ and $R^4$; wherein $R^1$ is independently selected from optionally substituted $C_{1-16}$ alkyl, optionally substituted aryl, and optionally substituted cycloalkyl; wherein $R^2$, $R^5$, and $R^6$ are independently selected from hydrogen, optionally substituted $C_{1-6}$ alkyl; wherein $R^3$ is independently selected from optionally substituted $C_{1-26}$ alkanoyl; optionally substituted $C_{1-26}$ alkenoyl, optionally substituted $C_{1-26}$ alkynoyl; optionally substituted cycloalkanoyl; wherein $R^4$ is independently selected from optionally substituted $C_{1-26}$ alkyl; optionally substituted $C_{1-26}$ alkenyl, optionally substituted $C_{1-26}$ alkynyl; optionally substituted cycloalkyl; and wherein $(A)_n$ is a peptide unit formed with amino acid units wherein n is independently 1, 2, 3, or 4.

In some embodiments, $R^1$ is selected from the group consisting of Me, Et, $^tBu$, 5-isopropyl-2-methylphenyl, and 2-isopropyl-5-methylphenyl.

In some embodiments, $R^2$ and $R^6$ are independently selected from the group consisting of H and Me.

In some embodiments, $R^2$ and $R^6$ are independently selected from the group consisting of H and Me, $R^3$ is independently selected from optionally substituted $C_{1-26}$ alkanoyl.

In some embodiments, $R^2$ and $R^6$ are independently selected from the group consisting of H and Me, $R^3$ is independently selected from optionally substituted $C_{1-26}$ alkanoyl, and $R^3$ is from $C_{12}$ to $C_{18}$ in chain length.

In some embodiments, $R^3$ is selected from the group consisting of acetyl, pivaloyl, butyryl, capryloyl, decanoyl, lauroyl, and stearoyl.

In some embodiments, X is —$O(CHR^2)OR^3$.

In some embodiments, when X is —$O(CHR^2)OR^3$, $R^2$ is independently selected from hydrogen, optionally substituted $C_{1-6}$alkyl.

In some embodiments, $R^4$ is —$CH_2CH_2COOH$.

In some embodiments, $(A)_n$ is selected from the group consisting of Val, Lys, Gly, Gly-Gly, Val-Val, Gly-Ala, Phe, Phe-Phe, Ala-Gly, and Lys-Lys.

In some embodiments, the compound of Formula (I) is selected from the group of at least one of the following:

Structure

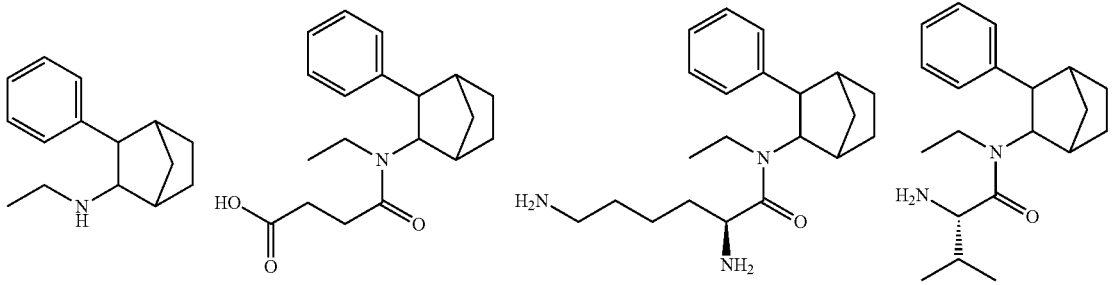

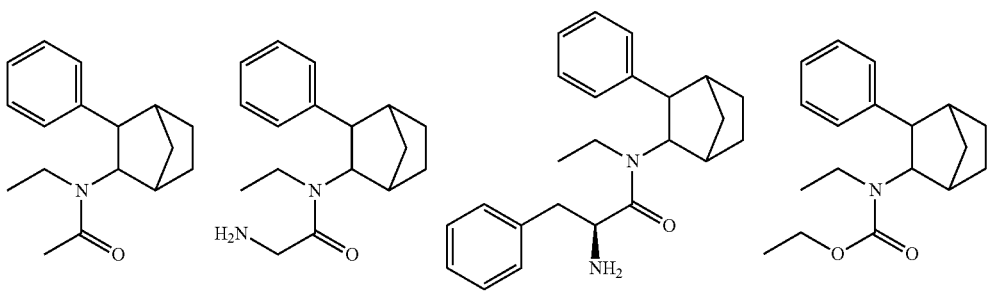

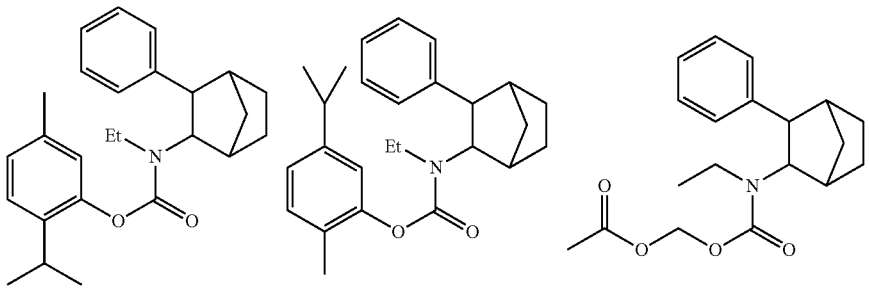

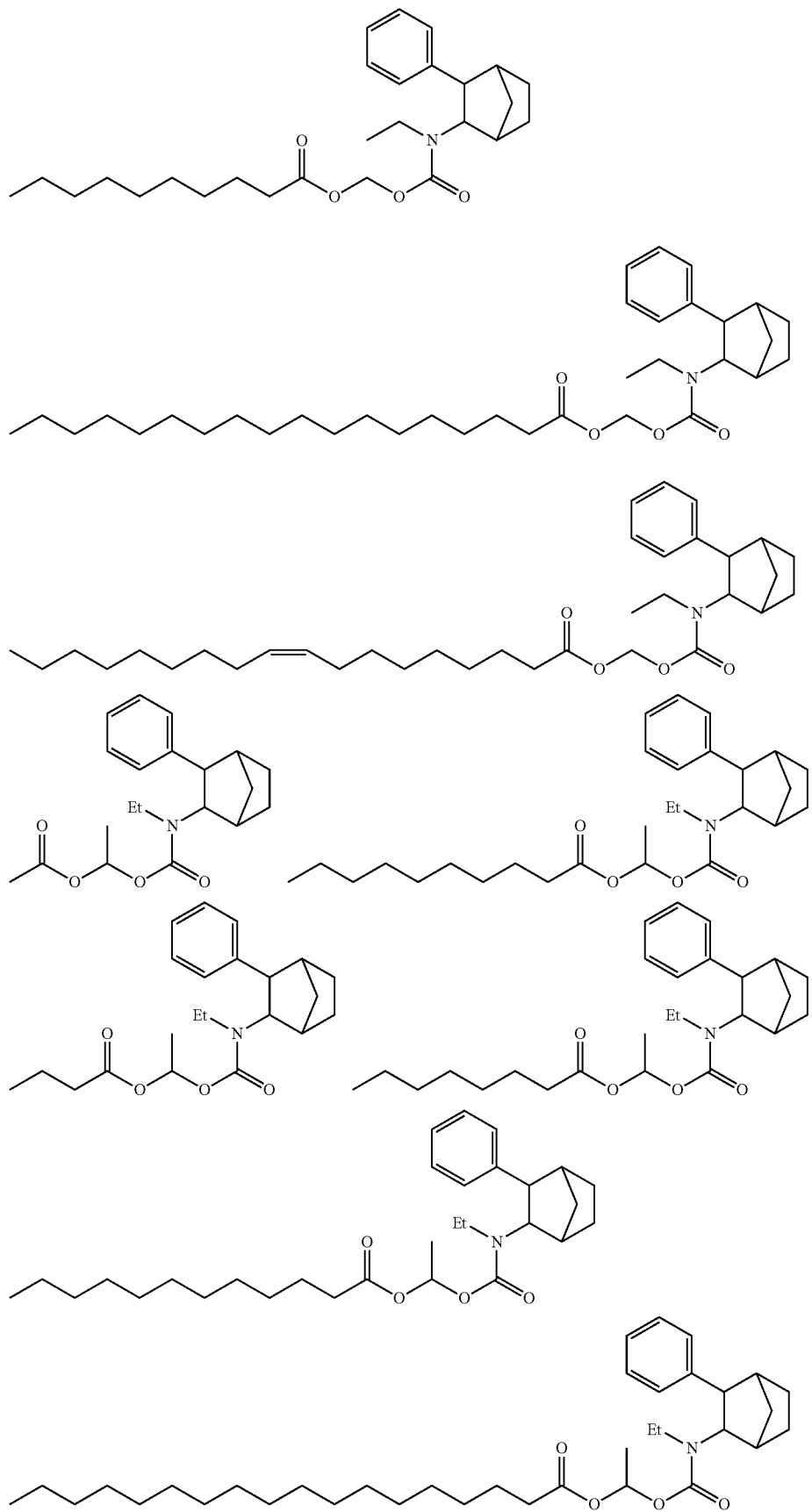

-continued
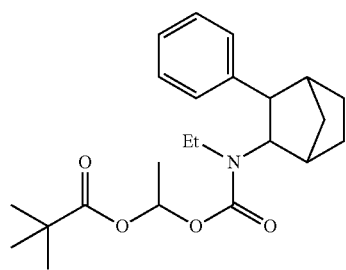
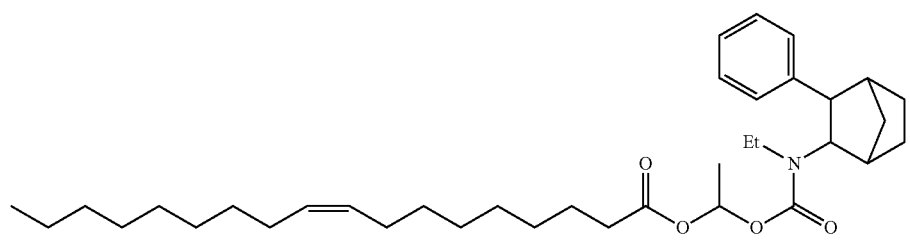
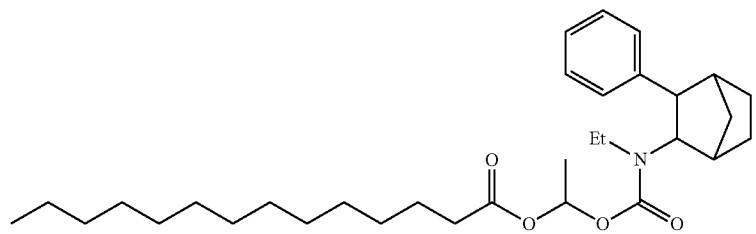
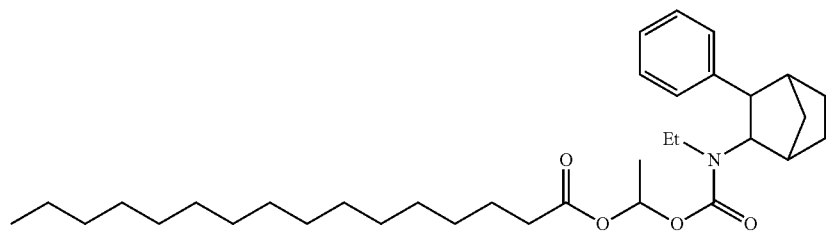
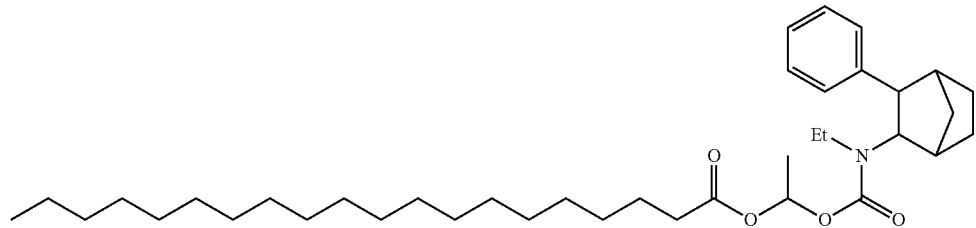
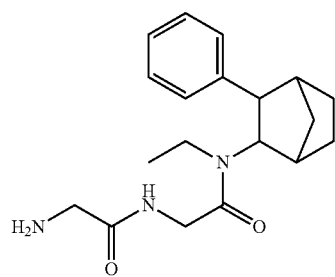
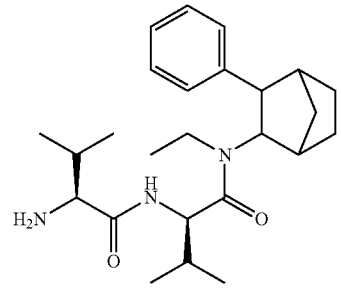
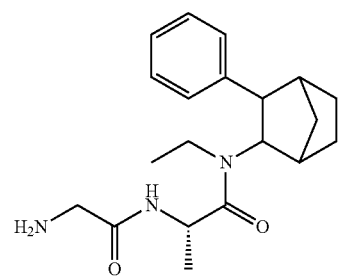

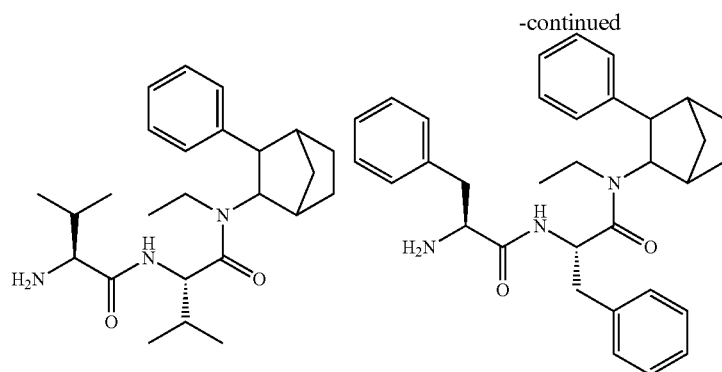
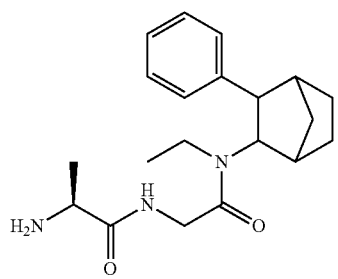
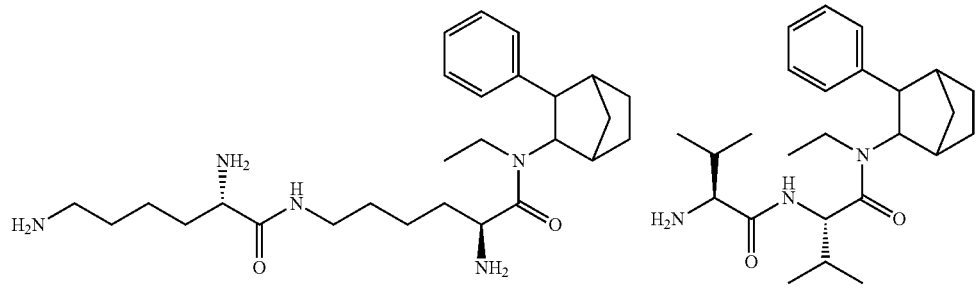
Some of the above formula can also be depicted by the following structures:
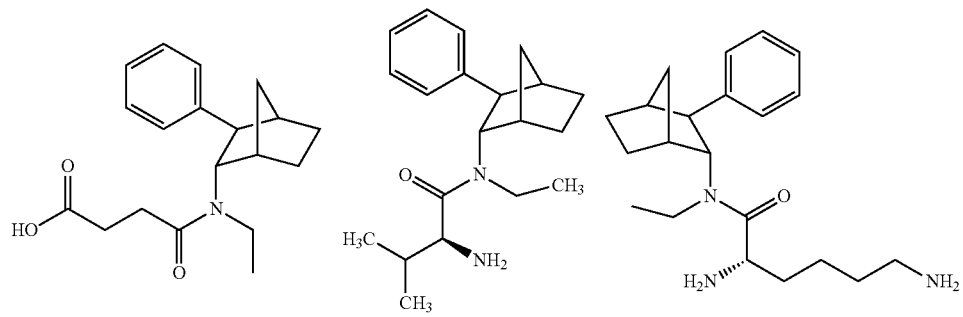
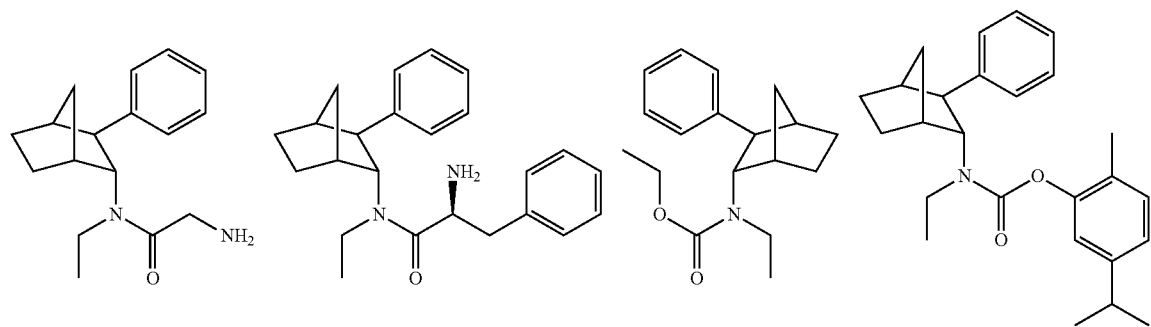

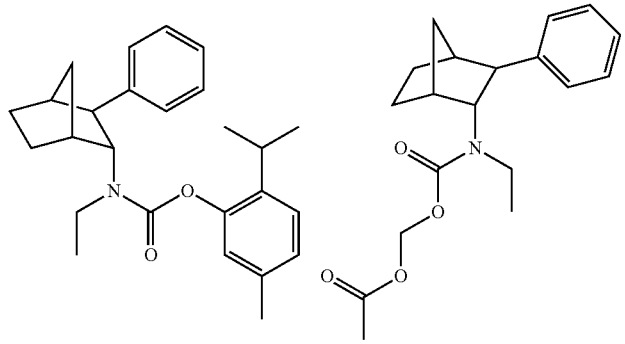
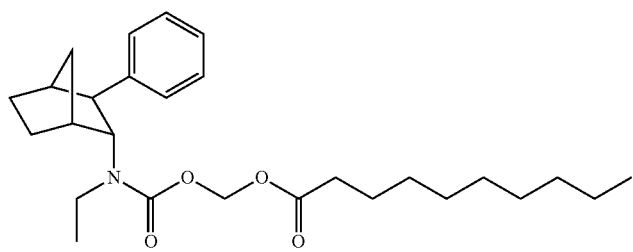
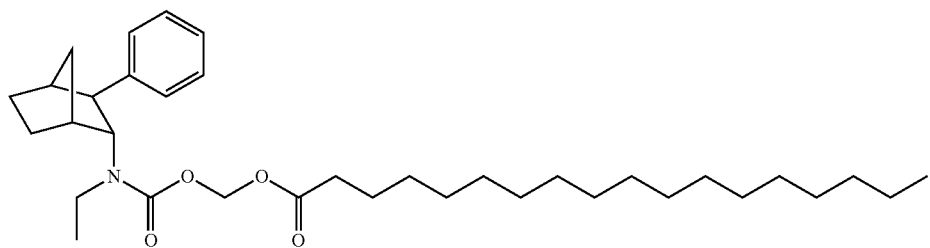
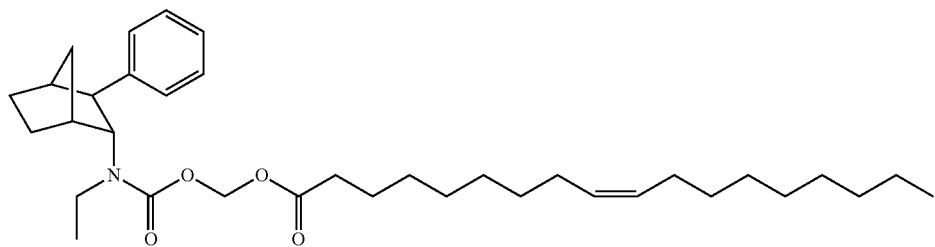
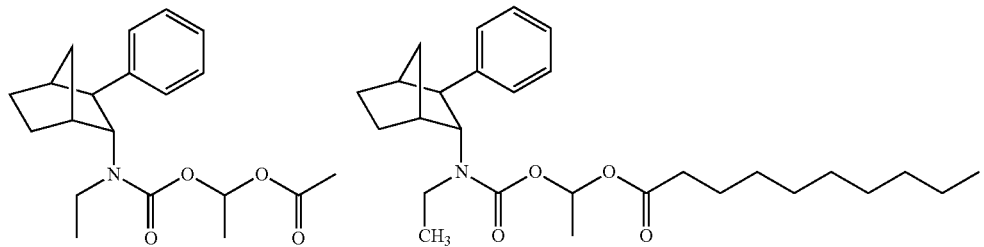
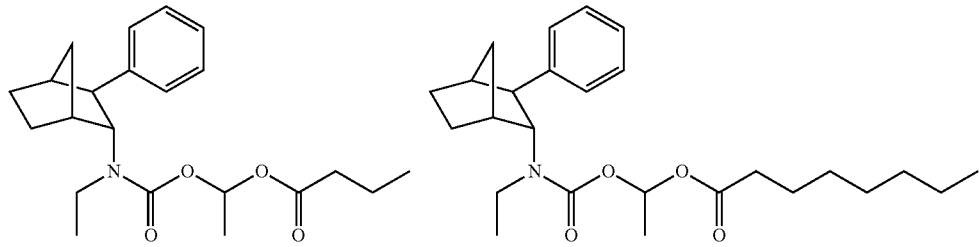

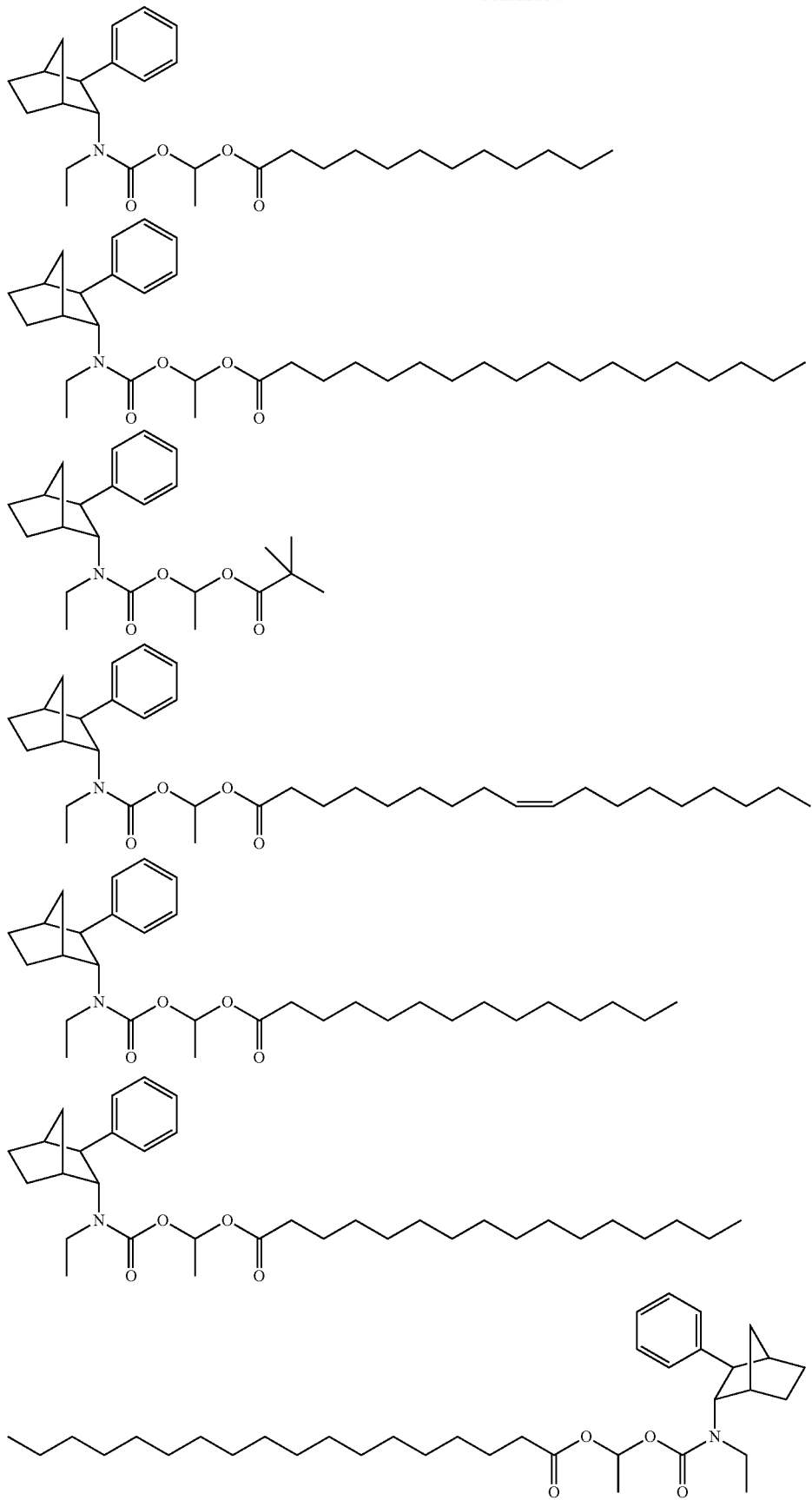

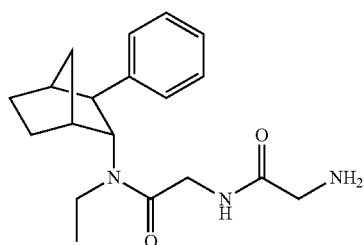
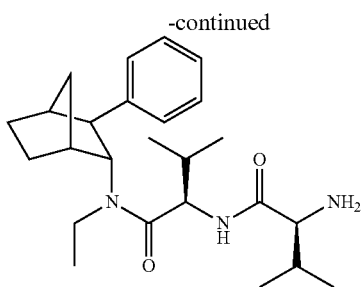
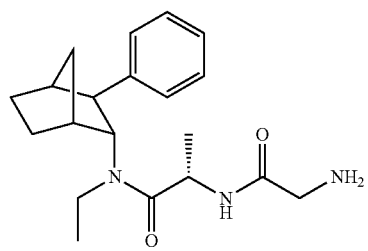
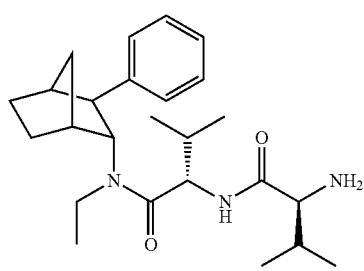
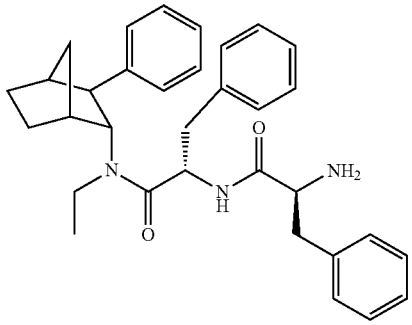
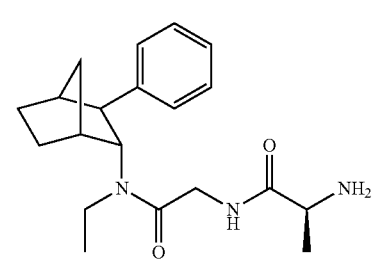
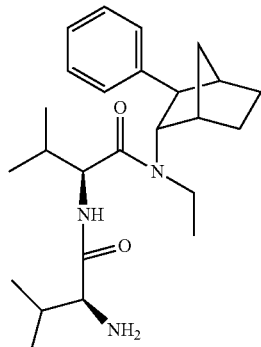
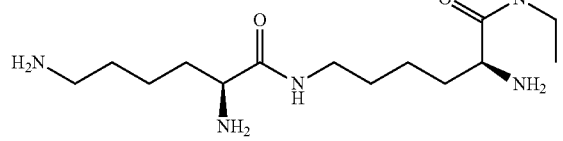
Some of the above formula can also be described by the following structures:
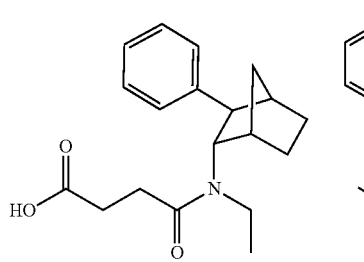
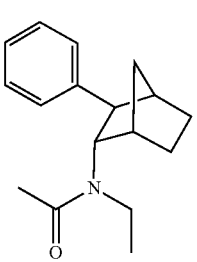
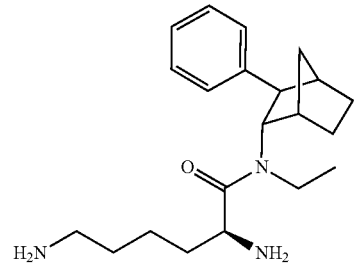
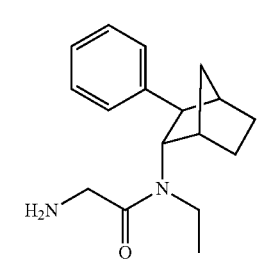
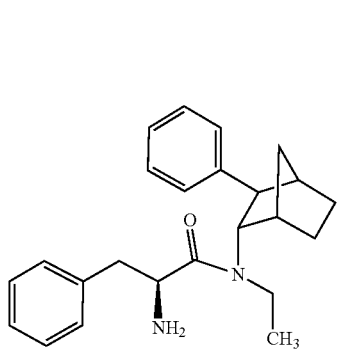
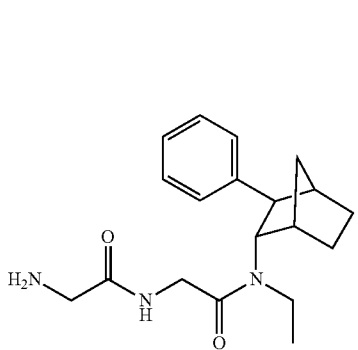
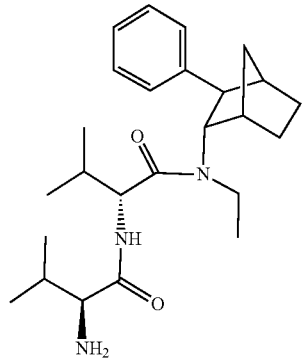

-continued
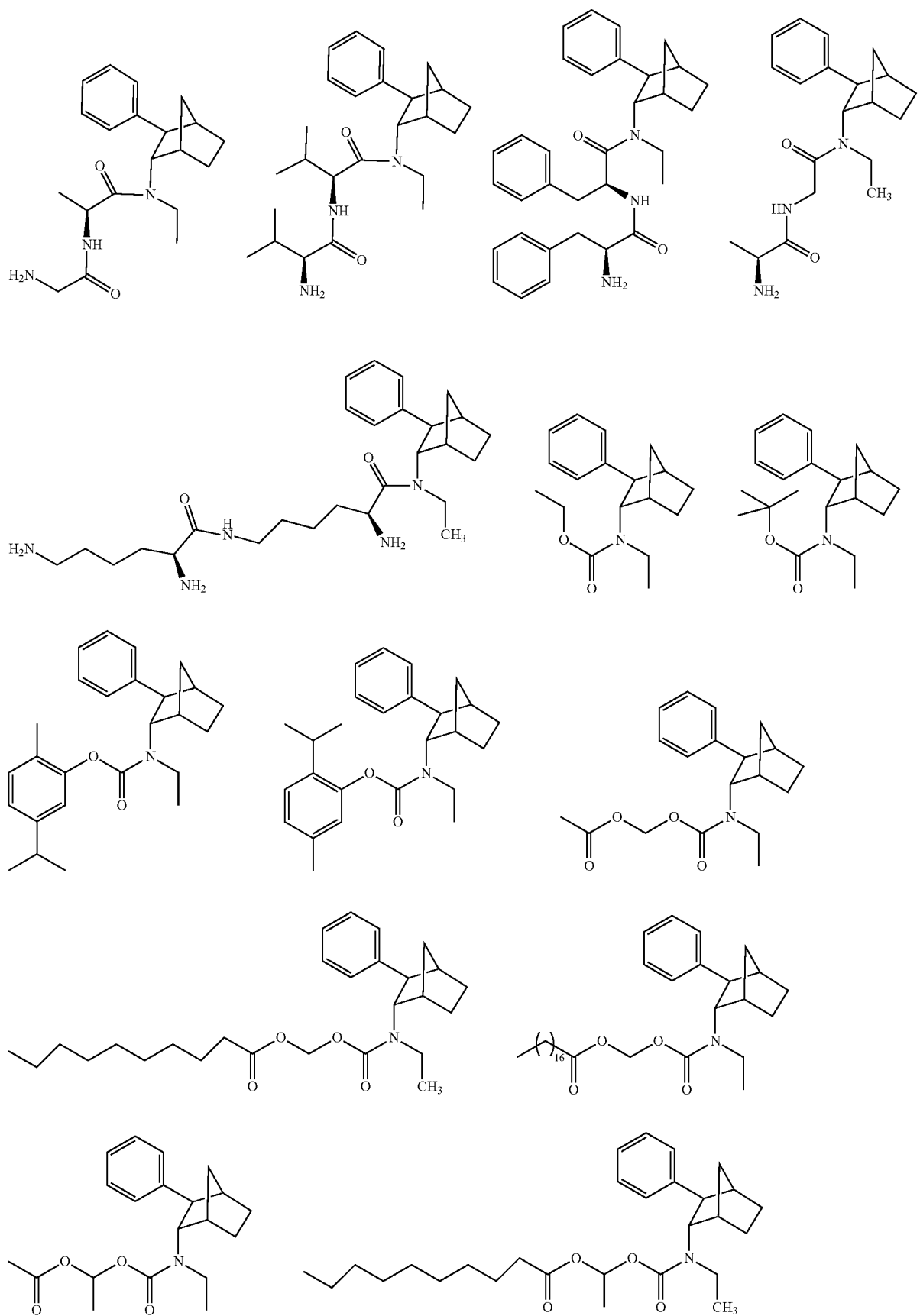

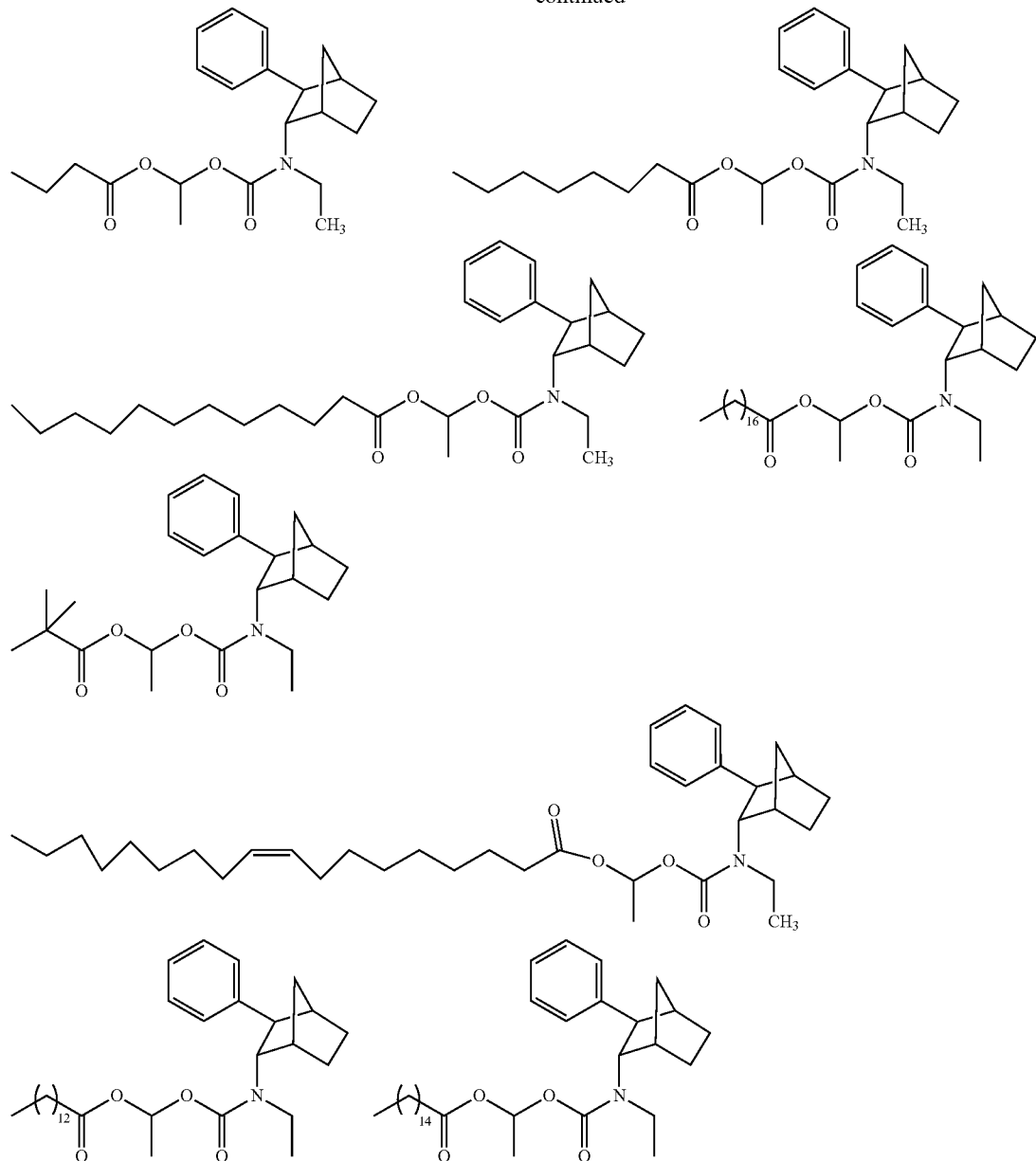

or a stereoisomer, or a pharmaceutically acceptable salt, ester, or solvate thereof. In some embodiments, any one or more of the formula identified above can be used in any of the compositions and/or methods provided herein.

In some embodiments, a pharmaceutical composition comprising the compound of any embodiment provided herein regarding fencamfamine and a pharmaceutically acceptable carrier is provided.

In some embodiments, one or more prodrug compositions of the present disclosure will surprisingly exhibit a slower rate of release over time as compared to unmodified fencamfamine.

In some embodiments, one or more prodrug compositions of the present disclosure provides reduced side effects as compared to unconjugated fencamfamine when administered at equimolar doses, and also provide reduced abuse potential as compared to unconjugated fencamfamine. In some embodiments, after administration of the prodrug of fencamfamine via IV, the amount of fencamfamine present in the subject's plasma is at least 5% less than if fencamfamine had been administered to the subject orally, for example, at least 10, 20, 30, 40, 50, 60, 70, 80, 90, 91, 92, 93, 94, 95, 96, 97, 98, 99, 99.1, 99.2, 99.3, 99.4, 99.5, 99.6, 99.7, 99.8, 99.9% or less, or 100%, including any range above any one of the preceding values and any range between any two of the preceding values.

In some embodiments one or more fencamfamine prodrug compositions of the present disclosure provides an amount sufficient to provide an extended $T_{max}$ when compared to unconjugated fencamfamine when administered at equimolar doses, and/or provides an equivalent $T_{max}$ when compared to unconjugated fencamfamine when administered at equimolar doses.

In some embodiments, one or more fencamfamine prodrug compositions of the present disclosure provides an increased level of the active drug (fencamfamine) in the plasma, when the prodrug compound is administered orally, in comparison to the amount of active present in the plasma when fencamfamine itself is administered (not as a prodrug). Thus, in some embodiments, the composition results in a higher level of active in the plasma, than would be present if the active itself had been administered. In some embodiments, the increase is at least 10, 20, 30, 40, 50, 60, 70, 80, 90, 100, 150, 200, 400% or more at any given point in time.

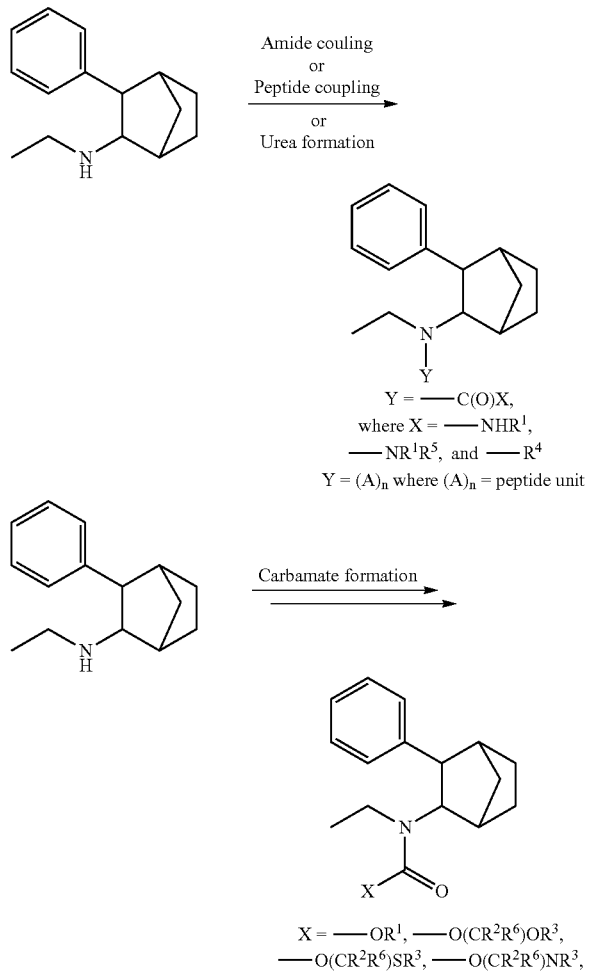

Synthetic Methods

Amide couling or Peptide coupling or Urea formation

Y = —C(O)X,
where X = —NHR$^1$,
—NR$^1$R$^5$, and —R$^4$
Y = (A)$_n$ where (A)$_n$ = peptide unit Carbamate formation X = —OR$^1$, —O(CR$^2$R$^6$)OR$^3$,
—O(CR$^2$R$^6$)SR$^3$, —O(CR$^2$R$^6$)NR$^3$, Compounds of Formula (I) described herein can be prepared in various ways. General synthetic routes to compounds of Formula (I) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims. In some embodiments, the fatty acid bonded prodrug is prepared by the reaction of PRX-002 with chloromethyl chloroformate or 1-chloroethyl chloroformate, followed by the reaction with various carboxylic acids in the presence of cesium carbonate and potassium iodide in DMF, as illustrated in the scheme 4.2. In some embodiments, the amino acid bonded prodrug is prepared by the coupling of PRX-002 with N-Boc protected amino acid and then removal of Boc group under acidic conditions. Further coupling with another N-Boc protected amino acid and subsequent deprotection provided dipeptide bonded prodrugs, as illustrated in Scheme 4.3.

Depending upon the substituents present, the compounds can be in a form of a pharmaceutically acceptable salt. The terms "pharmaceutically acceptable salt" as used herein are broad terms, and is to be given its ordinary and customary meaning to a person of ordinary skill in the art (and is not to be limited to a special or customized meaning), and refers without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity.

The compounds of preferred embodiments can include isomers, racemates, optical isomers, exo-isomers, endo-isomers, enantiomers, diastereomers, tautomers, and cis/trans conformers. All such isomeric forms are included within preferred embodiments, including mixtures thereof. As discussed above, the compounds of preferred embodiments may have chiral centers, for example, they may contain asymmetric carbon atoms and may thus exist in the form of enantiomers or diastereoisomers and mixtures thereof, e.g., racemates. Asymmetric carbon atom(s) can be present in the (R)- or (S)-configuration, or can be present as mixtures of the (R)- and (S)-forms. N-ethyl-3-phenylbicyclo[2.2.1]heptan-2-amine can exist as the Exo-phenyl,endo-amino and endo-phenyl,exo-amino substituted diastereomers. Each diastereomer is a pair of enantiomers. For e.g. the Exo-phenyl,endo-amino diastereomer is a mixture of the following two enantiomers, namely, (1S,2S,3R,4R)—N-ethyl-3-phenylbicyclo[2.2.1]heptan-2-amine and (1R,2R,3S,4S)—N-ethyl-3-phenylbicyclo[2.2.1]heptan-2-amine.

The following are enantiomeric forms of the Exo-phenyl, endo-amino isomer of the compounds of Formula (I):

Formula (I)

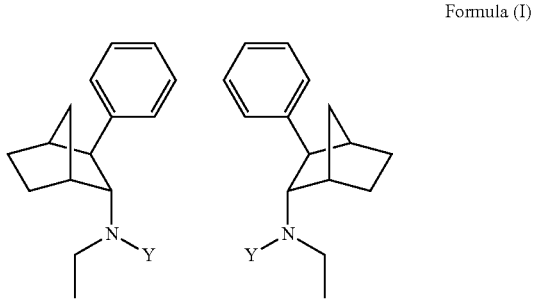

wherein Y=(L)-Val, (L)-Ala, Gly, (L)-Lys, Gly-Gly, (L)-Val-(L)-Val, (L)-Phe-(L)-Phe, (L)-Ala-Gly, (L)-Phe, Gly-(L)-Ala. In some embodiments, Y=Acyl, succinyl, alkyl-carbamoyl, aryl-oxycarbonyl, alkyl substituted-aryl-oxycarbonyl, analogues of (acyloxy)alkyl carbamates, alkyl substituted analogues of (acyloxy)alkyl carbamates, etc.

The compounds can be in amorphous form, or in crystalline forms. The crystalline forms of the compounds of preferred embodiments can exist as polymorphs, which are included in preferred embodiments. In addition, some of the compounds of preferred embodiments may also form solvates with water or other organic solvents. Such solvates are similarly included within the scope of the preferred embodiments.

In some embodiments, a fencamfamine prodrug is provided that comprises fencamfamine; a linker conjugated to the fencamfamine; and a fatty acid or at least one amino acid conjugated to the linker. In some embodiments, the moiety Y described herein can replace the linker and the fatty acid and/or at least one amino acid conjugated to the linker. In some embodiments, the linker comprises (acyloxy)ethyl ester linkage (—C(O)OCH(Me)O—). In some embodiments, the fencamfamine prodrug comprises a fatty acid. In some embodiments, the linker comprises (acyloxy)methyl ester linkage (—C(O)OCH$_2$O—). In some embodiments, the fencamfamine prodrug comprises a fatty acid. In some embodiments, the fatty acid is at least C12 in length. In some embodiments, the fatty acid is at least C16 in length. In some embodiments, the fatty acid is at least C18 in length. In some embodiments, the fencamfine prodrug comprises an amino acid conjugated to the linker. In some embodiments, the at least one amino acid comprises at least two amino acids as a peptide. In some embodiments, the at least two amino acids is a valine linked to a valine. It is noted that, when specified, the Y moiety description provided herein provides an alternative manner of describing various embodiments of the invention, without the need of separating the molecule into linker and blocker sections. Thus, the Y moiety description need not separately describe the linker and blocker components.

Embodiments of Pharmaceutical Compositions

In some embodiments, one can administer the prodrugs in an oral unit dosage form; however, other routes of administration are also possible. For various embodiments, contemplated routes of administration include but are not limited to oral, parenteral, intravenous, and subcutaneous. The prodrugs can be formulated into liquid preparations for, e.g., oral administration. Suitable forms include suspensions, syrups, elixirs, and the like. Particularly preferred unit dosage forms for oral administration include tablets and capsules. Unit dosage forms configured for administration once a day can be employed; however, in some embodiments it can be desirable to configure the unit dosage form for administration twice a day, or more.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the prodrug in admixture with excipients suitable for the manufacture of aqueous suspensions.

Formulations for oral use can also be provided as hard gelatin capsules, wherein the prodrug(s) are mixed with an inert solid diluent, such as calcium carbonate, calcium phosphate, or kaolin, or as soft gelatin capsules. In soft capsules, the prodrugs can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, antiadherents, coatings, disintegrants, fillers, flavors and colors, preservatives, sorbens, sweeteners, inert diluent, surface active or dispersing agent. Molded tablets can be made by molding, in a suitable machine, a mixture of the powdered prodrug moistened with an inert liquid diluent.

In some embodiments, each tablet or capsule contains from about 1 mg or less to about 1,000 mg or more of an prodrug of the preferred embodiments, more preferably from about 10, 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. In certain embodiments it can be preferred to incorporate two or more of the therapeutic agents to be administered into a single tablet or other dosage form (e.g., in a combination therapy); however, in other embodiments it can be preferred to provide the therapeutic agents in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as octadecanoic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein prodrug is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of prodrug doses.

In some embodiments, the pharmaceutical compositions of the prodrugs can be isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions can be maintained at the selected level using a pharmaceutically acceptable thickening agent. In some embodiments, methylcellulose can be used. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents.

In some embodiments, a pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

The prodrugs can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; $18^{th}$ and $19^{th}$ editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Pulmonary delivery can also be employed. The compound is delivered to the lungs while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of compound. Typically, each formulation is specific to the type of device employed and can involve the use of an appropriate propellant material, in addition to diluents, adjuvants, and/or carriers useful in therapy.

The compound and/or other optional active ingredients can be prepared for pulmonary delivery in particulate form with an average particle size of from 0.1 µm or less to 10 µm or more, more preferably from about 0.2, 0.3, 0.4, 0.5, 0.6, 0.7, 0.8, or 0.9 µm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 µm. Pharmaceutically acceptable carriers for pulmonary delivery of prodrug include carbohydrates such as trehalose, mannitol, xylitol, sucrose, lactose, and sorbitol. Other ingredients for use in formulations can include DPPC, DOPE, DSPC, and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Pharmaceutical formulations suitable for use with a nebulizer, either jet or ultrasonic, typically comprise the prodrug dissolved or suspended in water at a concentration of about 0.01 or less to 100 mg or more of prodrug per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation can also include a buffer and a simple sugar (e.g., for protein stabilization and regulation of osmotic pressure). The nebulizer formulation can also contain a surfactant, to reduce or prevent surface induced aggregation of the prodrug caused by atomization of the solution in forming the aerosol.

Formulations for use with a metered-dose inhaler device generally comprise a finely divided powder containing the active ingredients suspended in a propellant with the aid of a surfactant. The propellant can include conventional propellants, such as chlorofluorocarbons, hydrochlorofluorocarbons, hydrofluorocarbons, and hydrocarbons. Preferred propellants include trichlorofluoromethane, dichlorodifluoromethane, dichlorotetrafluoroethanol, 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing prodrug, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

When a compound is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

Kit Embodiments

In some embodiments, the prodrugs can be provided to an administering physician, other health care professional, or subject in the form of a kit. The kit is a package which houses a container which contains the compound in a suitable pharmaceutical composition, and instructions for administering the pharmaceutical composition to a subject. The kit can optionally also contain one or more additional therapeutic agents, e.g., chemotherapeutics currently employed for treating a cancer as described herein. For example, a kit containing one or more compositions comprising one or more prodrug in combination with one or more additional chemotherapeutic agents can be provided, or separate pharmaceutical compositions containing a prodrug of the preferred embodiments and additional therapeutic agents can be provided. The kit can also contain separate doses of a prodrug for serial or sequential administration. The kit can optionally contain one or more diagnostic tools and instructions for use. The kit can contain suitable delivery devices along with instructions for administering the prodrug(s) and any other therapeutic agent. The kit can optionally contain instructions for storage, reconstitution (if applicable), and administration of any or all therapeutic agents included. The kits can include a plurality of containers reflecting the number of administrations to be given to a subject. The kit can also include different types of fencamfamine prodrugs, as described herein. In some embodiments, the instructions can be inline with one or more of the methods outlined herein.

Methods of Use and Treatment

In some embodiments one or more prodrug compositions can be used for treating cancer-related fatigue by administering an effective amount of the composition to a subject in need thereof. In some embodiments, any of the prodrugs provided herein can be used. In some embodiments, the subject is human. In some embodiments, the subject has or had cancer. In some embodiments, the subject has gone through one or more rounds of a cancer therapy. In some embodiments, the subject has or has been diagnosed with cancer related fatigue.

In some embodiments, such as cancer-related fatigue, chronic fatigue syndrome, major depressive disorder, narcolepsy, advanced Parkinson's Disease, attention deficit-hyperactivity disorder (ADHD), substance-abuse disorders or Binge-eating disorder, the subject to be treated is in need of one or more of the benefits or properties of fencamfamine. In some embodiments, such as Alzheimer's disease, such as apathy in Alzheimer's disease and cognitive impairment in Alzheimer's disease and dopamine responsive dystonia the subject to be treated is in need of one or more of the benefits or properties of fencamfamine.

In some embodiments, the subject to be treated is at risk of abusing fencamfamine. In some embodiments, the risk is that the subject will or has taken fencamfamine via IV or injection. In some embodiments, some of the embodiments provided herein allow for a reduced risk that the subject will, or will repeat an IV administration of the prodrug.

In some embodiments, via the use of one or more of the prodrug compositions provided herein, one can provide to a subject a sufficient level of fencamfamine via oral administration, but not via IV administration (at least the amount of actived compound in the subject's plasma will be lower if given via IV than if given orally).

In some embodiments one or more prodrug compositions can be used for treating neurological disorders such as Parkinson's disease, Alzheimer's disease, and/or dopamine responsive dystonia by administering an effective amount of the composition to a subject in need thereof.

In some embodiment, the present disclosure provides at least one prodrug composition having an extended or controlled release profile as measured by plasma concentrations of released fencamfamine when compared to unconjugated fencamfamine when administered orally at equimolar doses. In some embodiments, the plasma concentration of fencamfamine released from the prodrug increases more slowly and over a longer period of time after oral administration, resulting in a delay in peak plasma concentration of released fencamfamine and in a longer duration of action when compared to unconjugated fencamfamine. In some embodiments, this can be the PRX-P6-011 using the + isomer) and/or PRX-P5-006 (using the − isomer) and/or PRX-P4-003 (using the − isomer).

In some embodiments, the subject is mammalian. In some embodiment, the subject is human.

In some embodiments, one or more of the fencamfamine prodrugs provides for an increase in an amount of fencamfamine present in a subject, compared to the administration of fencamfamine to the subject. Thus, in some embodiments, a method is provided for providing to a subject greater levels of fencamfamine by administering a prodrug of fencamfamine as described herein. In some embodiments, this can be a prodrug with a valine-valine Y moiety. In some embodiments, this can be the PRX-P6-011 compound.

In some embodiments, two or more of the fencamfamine prodrugs provided herein are combined into a composition of two or more of the fencamfamine prodrugs provided herein are administered to a subject. The two or more fencamfamine prodrugs can be administered serially or in parallel (either at overlapping volumes or over the same period of time). In some embodiments, this combination can be a first prodrug that provides delayed release and/or effects, while a second prodrug and provide a greater level of availability of the active than would be present if fencamfamine were given directly. For example, this can be achieved by having PRX-P5-006 as the first prodrug, to provide a delayed onset and/or abuse-resistance, while having PRX-P6-011 as the second prodrug so as to provide a greater initial and/or sustained level of fencamfamine isomer compared to parent.

In some embodiments, the prodrugs or conjugate compositions of the present disclosure can be administered orally and, upon administration, release N-ethyl-3-phenylbicyclo[2.2.1]heptan-2-amine, derivatives thereof (which would include some part of the Y moiety from the prodrug) or combinations thereof, after being hydrolyzed in the body. Without being bound by any particular theory, in some embodiments, the acyloxyalkoxycarbonyl bonded fatty acids that are conjugated to the N-ethyl-3-phenylbicyclo[2.2.1]heptan-2-amine, derivatives thereof or combinations thereof, of the present disclosure are naturally occurring metabolites, pharmaceutically active compounds or mimetics thereof or derivatives thereof. The prodrugs or conjugates of the present disclosure can be recognized by physiological systems resulting in hydrolysis and release of N-ethyl-3-phenylbicyclo[2.2.1]heptan-2-amine (or a derivative thereof), when taken orally, but not when taken via IV injection.

Some embodiments of the prodrugs are believed to have no or limited pharmacological activity themselves and consequently may follow a metabolic pathway that differs from the parent drug (i.e., N-ethyl-3-phenylbicyclo[2.2.1]heptan-2-amine). Without being bound by any theory, by choosing a suitable blocking moiety, such as an acyl group from a carboxylic acid, the release of N-ethyl-3-phenylbicyclo[2.2.1]heptan-2-amine into the systemic circulation can be controlled even when the prodrug is administered via routes other than oral administration.

In some embodiments, the prodrugs of N-ethyl-3-phenylbicyclo[2.2.1]heptan-2-amine, derivatives thereof or combinations thereof, of the present disclosure surprisingly release N-ethyl-3-phenylbicyclo[2.2.1]heptan-2-amine, derivatives thereof or combinations thereof, similar to free or unmodified N-ethyl-3-phenylbicyclo[2.2.1]heptan-2-amine. That is, the activated prodrug is identical or similar in its properties to the original form of the drug (fencamfamine).

In some embodiments, the at least one conjugated N-ethyl-3-phenylbicyclo[2.2.1]heptan-2-amine, derivatives thereof or combinations thereof, of the present disclosure are believed to be released in a controlled or sustained form.

In some embodiments, the at least one prodrug or conjugate generates a $T_{max}$ value of released N-ethyl-3-phenylbicyclo[2.2.1]heptan-2-amine that is longer than the $T_{max}$ value produced by "unconjugated" N-ethyl-3-phenylbicyclo[2.2.1]heptan-2-amine (i.e., the active) when administered at equimolar doses. In another embodiment, the at least one prodrug or conjugate generates a $T_{max}$ value of released N-ethyl-3-phenylbicyclo[2.2.1]heptan-2-amine that is similar to the $T_{max}$ value produced by unconjugated N-ethyl-3-phenylbicyclo[2.2.1]heptan-2-amine, when administered at equimolar doses.

In some embodiments, the AUC is about 50% or smaller of the AUC of unconjugated N-ethyl-3-phenylbicyclo[2.2.1]heptan-2-amine, when administered intranasally or intravenously at equimolar doses, for example about 50% to about 0.1%, alternatively from about 25% to about 0.1%, alternatively from about 50% to about 1%, including, but not limited to, about 50%, about 40%, about 30%, about 20%, about 10%, about 1% or any amounts in between, in increments of about 0.5%, about 1%, about 2%, about 2.5%, about 5% or about 10%.

In some embodiments, the compounds, prodrugs, compositions and/or methods of the present disclosure provide reduced potential for overdose, reduced potential for abuse and/or improve the characteristics of N-ethyl-3-phenylbicyclo[2.2.1]heptan-2-amine, derivatives thereof or combinations thereof with regard to toxicities or suboptimal release profiles.

In some embodiments, some compositions may have no or a substantially decreased pharmacological activity when administered through intravenous injection or intranasal routes of administration. However, they remain orally bioavailable. Without being limited to the below theory, overdose protection may occur due to the conjugates being exposed to different enzymes and/or metabolic pathways after oral administration whereby the conjugate of the present disclosure is exposed to the gut and first-pass metabolism as opposed to exposure to enzymes in the circulation or mucosal membranes in the nose which limits the ability of the N-ethyl-3-phenylbicyclo[2.2.1]heptan-2-amine, derivatives thereof or combinations thereof, from being released from the conjugate. Therefore, in some embodiments, abuse resistance is provided by limiting the effectiveness of alternative routes of administration. Again, not being bound by any particular theory, the bioavailability can be a result of the hydrolysis of the chemical linkage (such as a covalent linkage) following oral administration. In at least one alternative embodiment, the prodrugs of the present disclosure are envisioned to not hydrolyze or to hydrolyze at a reduced rate or to a limited extent via non-oral routes. As a result, they are believed to not generate high plasma or blood concentrations of released N-ethyl-3-phenylbicyclo[2.2.1]heptan-2-amine when injected or snorted compared to free N-ethyl-3-phenylbicyclo[2.2.1]heptan-2-amine administered through these routes.

In some embodiments, at least some compositions of the present disclosure comprising the prodrugs of one or more N-ethyl-3-phenylbicyclo[2.2.1]heptan-2-amine, derivatives thereof or combinations thereof, are resistant to abuse by parenteral routes of administration, such as intravenous "shooting," or intranasal "snorting," that are often employed during illicit use. In at least some contemplated alternative embodiments, release of N-ethyl-3-phenylbicyclo[2.2.1]heptan-2-amine, derivatives thereof or combinations thereof, is reduced when the composition of the present disclosure is delivered by parenteral routes. In some embodiments, the conjugates, since they are believed to include covalently bound N-ethyl-3-phenylbicyclo[2.2.1]heptan-2-amine, derivatives thereof or combinations thereof, are not able to be physically manipulated to release the N-ethyl-3-phenylbicyclo[2.2.1]heptan-2-amine, derivatives thereof or combinations thereof, from the conjugated N-ethyl-3-phenylbicyclo[2.2.1]heptan-2-amine, derivatives thereof or combinations thereof, by methods, for example, of grinding up or crushing of solid forms. In some embodiments, some compositions containing prodrugs or conjugates of the present disclosure preferably have no or a substantially decreased pharmacological activity when administered through injection or intranasal routes of administration. However, they remain orally bioavailable.

In some embodiments, the present disclosure provides a stimulant based treatment modality and dosage form for certain disorders requiring the stimulation of the CNS such as, cancer-related fatigue, chronic fatigue syndrome, major depressive disorder, narcolepsy, advanced Parkinson's Disease, ADHD, substance-abuse disorders, binge-eating disorder Alzheimer's disease (such as apathy in Alzheimer's disease), or Dopamine Responsive Dystonia.

In some embodiments, the at least one composition or prodrug of the present disclosure can be used in one or more methods of treating a patient having at least one disease, disorder or condition requiring stimulation of the central nervous system of one or more patients, comprising orally administering a pharmaceutically effective amount of the at least one composition or prodrug.

Certain compounds, compositions and methods provided herein can be used to treat a number of disorders such as those requiring the stimulation of the CNS such as, cancer-related fatigue i.e. fatigue caused due to chemotherapy induced anemia, fatigue caused due to radiation therapy, depression, chronic fatigue syndrome, or major depressive disorder narcolepsy. In some embodiments, certain compounds, compositions and methods provided herein can be used to treat Alzheimer's disease, such as apathy in Alzheimer's disease and cognitive impairment in Alzheimer's disease. In some embodiments, certain compounds, compositions and methods provided herein can be used to treat dopamine responsive dystonia.

In some embodiments, the prodrug provided herein is mostly (at least 50%, for example, at least 60, at least 70, at least 80, at least 90, at least 91, at least 92, at least 93, at least 94, at least 95, at least 96, at least 97, at least 98, at least 99, at least 100% metabolized by an oral route, over an IV route. In some embodiments, the prodrug component (the non-active) or any hydrolyzed products, are not toxic. In some embodiments, there is a good AUC (at least about 50% compared to the active). In some embodiments, the product allows for once a day dosing (or is configured in an amount for such dosing). In some embodiments, the product has an abuse resistant profile (delayed Tmax and/or low Cmax). In some embodiments, the prodrug, has a relatively low IV conversion rate (compared to oral). In some embodiments, the prodrug moiety is safe for human consumption.

For convenience, Table 1 displays a listing of the various chemical names with the names used herein of the actives and prodrugs, as well as the structures. The structures in Table 1 do not necessarily depict the absolute configurations of (+)- and (−)-N-Ethyl-3-phenylbicyclo[2.2.1]heptan-2-amine.

In some embodiments, any one or more of the prodrugs provided in Table 1 can be part of any composition and/or formulation and/or method provided herein.

TABLE 1

COMPOUNDS

| Compound Identification | Fencamfamne Isomer | Chemical Name | Structure |
|---|---|---|---|
| PRX-001 | (±) | N-Ethyl-3-phenylbicyclo[2.2.1]heptan-2-amine (Racemic mixture) | 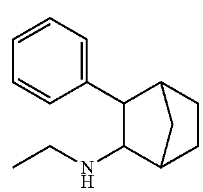 [SMILES: CCNC1C2CCC(C2)C1c1ccccc1] |
| PRX-002 | (+) | N-Ethyl-3-phenylbicyclo[2.2.1]heptan-2-amine ((+)-isomer) | 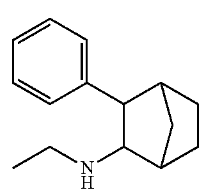 [SMILES: CCNC1C2CCC(C2)C1c1ccccc1] |

TABLE 1-continued

COMPOUNDS

| Compound Identification | Fencamfamne Isomer | Chemical Name | Structure |
|---|---|---|---|
| PRX-002 | (−) | N-Ethyl-3-phenylbicyclo[2.2.1]heptan-2-amine ((−)-isomer) | 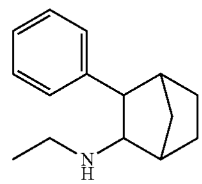 [SMILES: CCNC1C2CCC(C2)C1c1ccccc1] |
| PRX-P1-001 | (±) | N-Succinyl-N-ethyl-3-phenylbicyclo[2.2.1]heptan-2-amine | 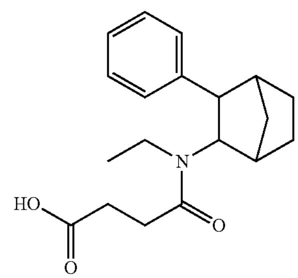 [SMILES: CCN(C(=O)CCC(=O)O)C1C2CCC(C2)C1c1ccccc1] |
| PRX-P1-005 | (−) | N-Lysyl-(−)-N-ethyl-3-phenylbicyclo[2.2.1]heptan-2-amine | 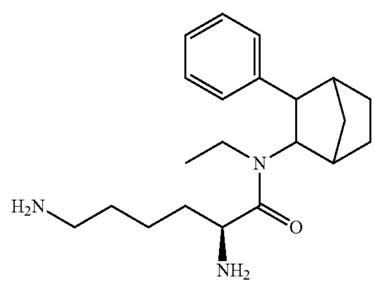 [SMILES: CCN(C(=O)[C@@H](N)CCCCN)C1C2CCC(C2)C1c1ccccc1] |
| PRX-P1-006 | (±) | N-Valyl-N-ethyl-3-phenylbicyclo[2.2.1]heptan-2-amine | 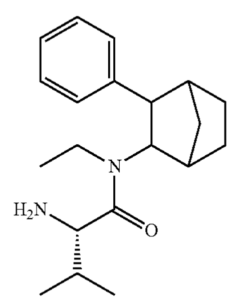 [SMILES: CCN(C(=O)[C@@H](N)C(C)C)C1C2CCC(C2)C1c1ccccc1] |
| PRX-P1-011 | (−) | N-Acetyl-(−)-N-ethyl-3-phenylbicyclo[2.2.1]heptan-2-amine | 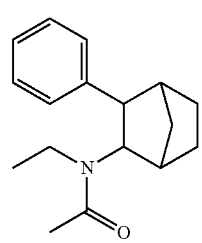 [SMILES: CCN(C(C)=O)C1C2CCC(C2)C1c1ccccc1] |

TABLE 1-continued

COMPOUNDS

| Compound Identification | Fencamfamne Isomer | Chemical Name | Structure |
|---|---|---|---|
| PRX-P1-012 | (−) | N-Glycyl-(−)-N-ethyl-3-phenylbicyclo[2.2.1]heptan-2-amine | 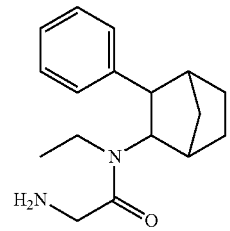 [SMILES: CCN(C(=O)CN)C1C2CCC(C2)C1c1ccccc1] |
| PRX-P1-013 | (−) | N-Phenylalanyl-(−)-N-ethyl-3-phenylbicyclo[2.2.1]heptan-2-amine | 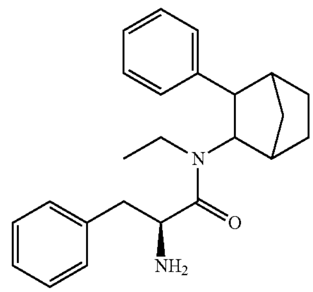 [SMILES: CCN(C(=O)[C@@H](N)Cc1ccccc1)C1C2CCC(C2)C1c1ccccc1] |
| PRX-P2-001 | (±) | N-Ethoxycarbonyl-N-ethyl-3-phenylbicyclo[2.2.1]heptan-2-amine | 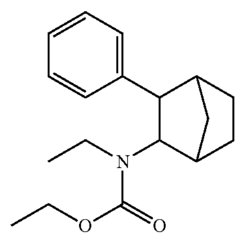 [SMILES: CCOC(=O)N(CC)C1C2CCC(C2)C1c1ccccc1] |
| PRX-P3-002 | (−) | N-(5-Isopropyl-2-methylphenoxycarbonyl)-(−)-N-ethyl-3-phenylbicyclo[2.2.1]heptan-2-amine | 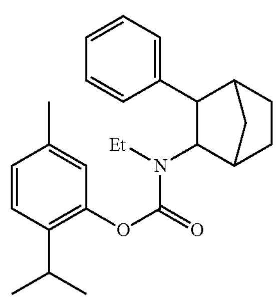 [SMILES: CCN(C(=O)Oc1cc(C)ccc1C(C)C)C1C2CCC(C2)C1c1ccccc1] |
| PRX-P3-004 | (−) | N-(2-Isopropyl-5-methylphenoxycarbonyl)-(−)-N-ethyl-3-phenylbicyclo[2.2.1]heptan-2-amine | 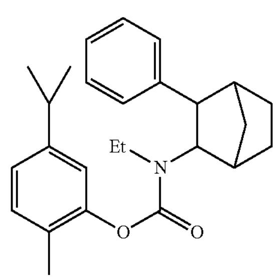 [SMILES: CCN(C(=O)Oc1cc(C(C)C)ccc1C)C1C2CCC(C2)C1c1ccccc1] |

TABLE 1-continued

COMPOUNDS

| Compound Identification | Fencamfamne Isomer | Chemical Name | Structure |
|---|---|---|---|
| PRX-P4-001 | (−) | N-(Acetoxymethoxycarbonyl)-(−)-N-ethyl-3-phenylbicyclo[2.2.1]heptan-2-amine | 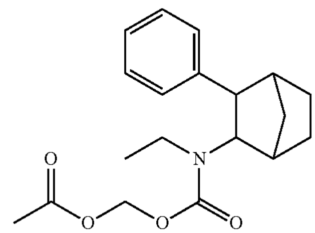 [SMILES: CCN(C(=O)OCOC(C)=O)C1C2CCC(C2)C1c1ccccc1] |
| PRX-P4-002 | (−) | N-(Decanoyloxymethoxycarbonyl)-(−)-N-ethyl-3-phenylbicyclo[2.2.1]heptan-2-amine | 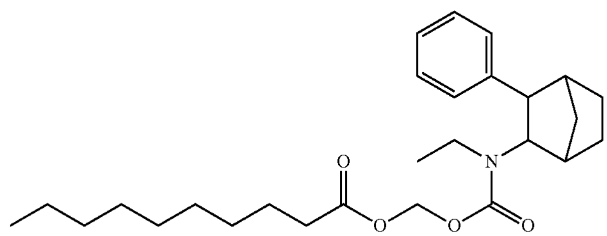 [SMILES: CCCCCCCCCC(=O)OCOC(=O)N(CC)C1C2CCC(C2)C1c1ccccc1] |
| PRX-P4-003 | (−) | N-(Octadecanoyloxymethoxycarbonyl)-(−)-N-ethyl-3-phenylbicyclo[2.2.1]heptan-2-amine | 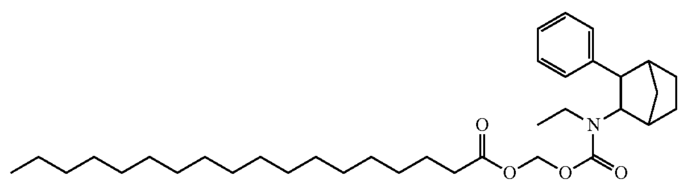 [SMILES: CCCCCCCCCCCCCCCCCC(=O)OCOC(=O)N(CC)C1C2CCC(C2)C1c1ccccc1] |
| PRX-P4-004 | (−) | N-((Z)-Octadec-9-enoyloxymethoxycarbonyl)-(−)-N-ethyl-3-phenylbicyclo[2.2.1]heptan-2-amine | 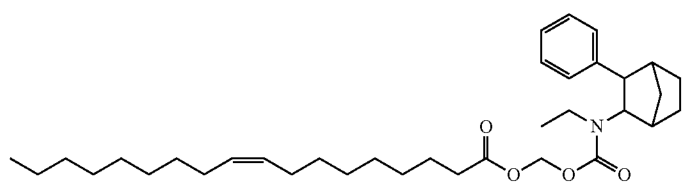 [SMILES: CCCCCCCC/C=C\CCCCCCCC(=O)OCOC(=O)N(CC)C1C2CCC(C2)C1c1ccccc1] |
| PRX-P5-001 | (−) | N-(1-Acetoxyethoxycarbonyl)-(−)-N-ethyl-3-phenylbicyclo[2.2.1]heptan-2-amine | 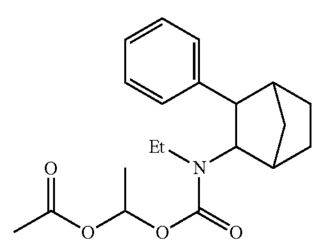 [SMILES: CCN(C(=O)OC(C)OC(C)=O)C1C2CCC(C2)C1c1ccccc1] |
| PRX-P5-002 | (−) | N-(1-Decanoyloxyethoxycarbonyl)-(−)-N-ethyl-3-phenylbicyclo[2.2.1]heptan-2-amine | 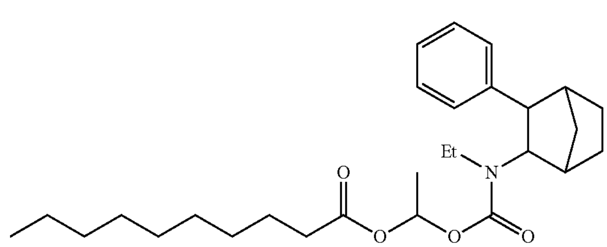 [SMILES: CCCCCCCCCC(=O)OC(C)OC(=O)N(CC)C1C2CCC(C2)C1c1ccccc1] |

TABLE 1-continued

COMPOUNDS

| Compound Identification | Fencamfamne Isomer | Chemical Name | Structure |
|---|---|---|---|
| PRX-P5-003 | (−) | N-(1-Butanoyloxyethoxycarbonyl)-(−)-N-ethyl-3-phenylbicyclo[2.2.1]heptan-2-amine | 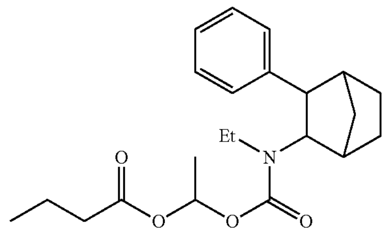 [SMILES: CCCC(=O)OC(C)OC(=O)N(CC)C1C2CCC(C2)C1c1ccccc1] |
| PRX-P5-004 | (−) | N-(1-Octanoyloxyethoxycarbonyl)-(−)-N-ethyl-3-phenylbicyclo[2.2.1]heptan-2-amine | 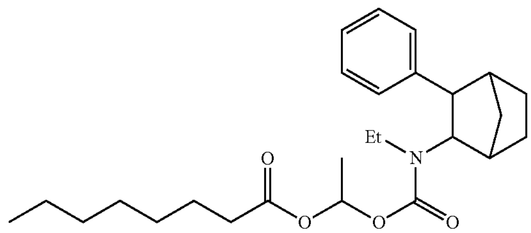 [SMILES: CCCCCCCC(=O)OC(C)OC(=O)N(CC)C1C2CCC(C2)C1c1ccccc1] |
| PRX-P5-005 | (−) | N-(1-Dodecanoyloxyethoxy-carbonyl)-(−)-N-ethyl-3-phenylbicyclo[2.2.1]heptan-2-amine | 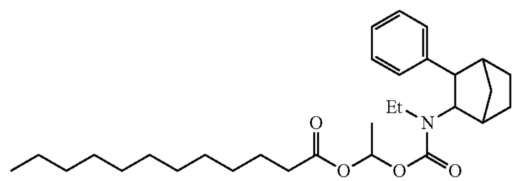 [SMILES: CCCCCCCCCCCC(=O)OC(C)OC(=O)N(CC)C1C2CCC(C2)C1c1ccccc1] |
| PRX-P5-006 | (−) | N-(1-Octadecanoyloxyethoxy-carbonyl)-(−)-N-ethyl-3-phenylbicyclo[2.2.1]heptan-2-amine | 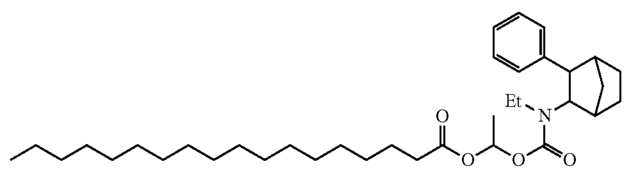 [SMILES: CCCCCCCCCCCCCCCCCC(=O)OC(C)OC(=O)N(CC)C1C2CCC(C2)C1c1ccccc1] |
| PRX-P5-007 | (−) | N-(1-(2,2-Dimethylpropionyloxy)ethoxy-carbonyl)-(−)-N-ethyl-3-phenylbicyclo[2.2.1]heptan-2-amine | 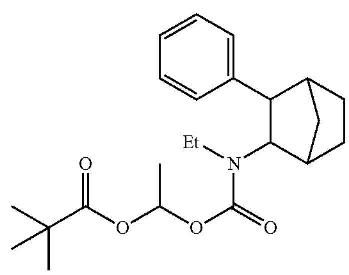 [SMILES: CCN(C(=O)OC(C)OC(=O)C(C)(C)C)C1C2CCC(C2)C1c1ccccc1] |
| PRX-P5-008 | (−) | N-(1-(Z)-Octadec-9-enoyloxy)ethoxycarbonyl)-(−)-N-ethyl-3-phenylbicyclo[2.2.1]heptan-2-amine | 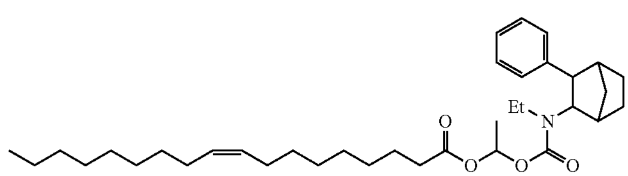 [SMILES: CCCCCCCC/C=C\CCCCCCCC(=O)OC(C)OC(=O)N(CC)C1C2CCC(C2)C1c1ccccc1] |
| PRX-P5-009 | (−) | N-(1-Tetradecanoyloxyethoxy-carbonyl)-(−)-N-ethyl-3-phenylbicyclo[2.2.1]heptan-2-amine | 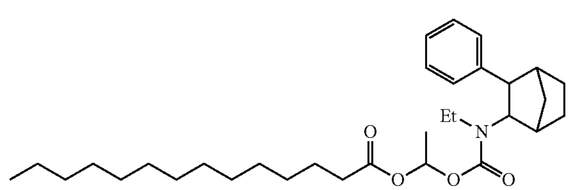 [SMILES: CCCCCCCCCCCCCC(=O)OC(C)OC(=O)N(CC)C1C2CCC(C2)C1c1ccccc1] |

TABLE 1-continued

COMPOUNDS

| Compound Identification | Fencamfamne Isomer | Chemical Name | Structure |
| --- | --- | --- | --- |
| PRX-P5-010 | (−) | N-(1-Hexadecanoyloxyethoxy-carbonyl)-(−)-N-ethyl-3-phenylbicyclo[2.2.1]heptan-2-amine | 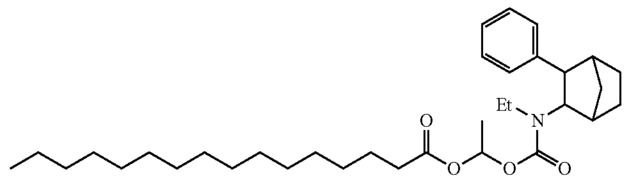 [SMILES: CCCCCCCCCCCCCCCC(=O)OC(C)OC(=O)N(CC)C1C2CCC(C2)C1c1ccccc1] |
| PRX-P5-011 | (+) | N-(1-Octadecanoyloxyethoxy-carbonyl)-(+)-N-ethyl-3-phenylbicyclo[2.2.1]heptan-2-amine | 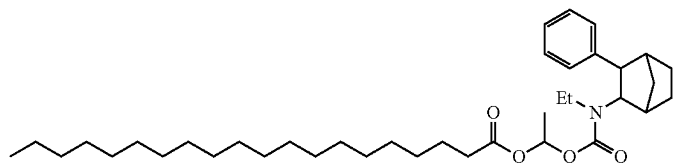 [SMILES: CCCCCCCCCCCCCCCCCCCC(=O)OC(C)OC(=O)N(CC)C1C2CCC(C2)C1c1ccccc1] |
| PRX-P6-001 | (−) | N-(Glycyl-glycyl)-(−)-N-ethyl-3-phenylbicyclo[2.2.1]heptan-2-amine | 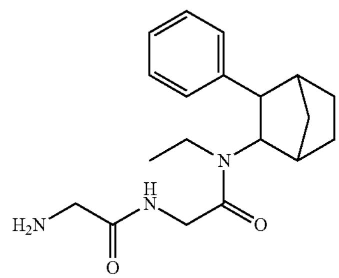 [SMILES: CCN(C(=O)CNC(=O)CN)C1C2CCC(C2)C1c1ccccc1] |
| PRX-P6-002 | (−) | N-(Valyl-D-valyl)-(−)-N-ethyl-3-phenylbicyclo[2.2.1]heptan-2-amine | 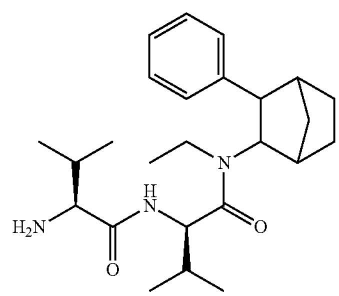 [SMILES: CCN(C(=O)[C@H](NC(=O)[C@@H](N)C(C)C)C(C)C)C1C2CCC(C2)C1c1ccccc1] |
| PRX-P6-003 | (−) | N-(Glycyl-Alanyl)-(−)-N-ethyl-3-phenylbicyclo[2.2.1]heptan-2-amine | 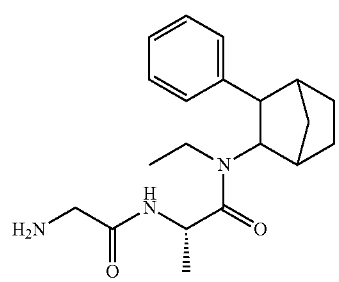 [SMILES: CCN(C(=O)[C@H](C)NC(=O)CN)C1C2CCC(C2)C1c1ccccc1] |
| PRX-P6-004 | (−) | N-(Valyl-valyl)-(−)-N-ethyl-3-phenylbicyclo[2.2.1]heptan-2-amine | 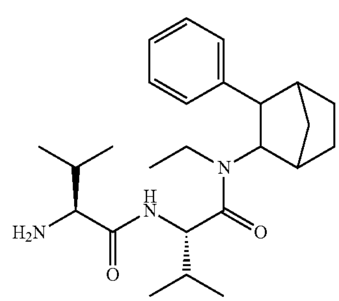 [SMILES: CCN(C(=O)[C@@H](NC(=O)[C@@H](N)C(C)C)C(C)C)C1C2CCC(C2)C1c1ccccc1] |

TABLE 1-continued

COMPOUNDS

| Compound Identification | Fencamfamne Isomer | Chemical Name | Structure |
|---|---|---|---|
| PRX-P6-005 | (−) | N-(Phenylalanyl-phenylalanyl)-(−)-N-ethyl-3-phenylbicyclo[2.2.1]heptan-2-amine | 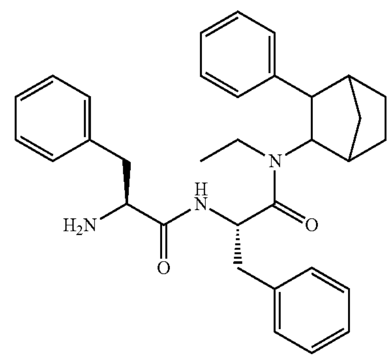 [SMILES: CCN(C(=O)[C@H](Cc1ccccc1)NC(=O)[C@@H](N)Cc1ccccc1)C1C2CCC(C2)C1c1ccccc1] |
| PRX-P6-006 | (−) | N-(Alanyl-glycyl)-(−)-N-ethyl-3-phenylbicyclo[2.2.1]heptan-2-amine | 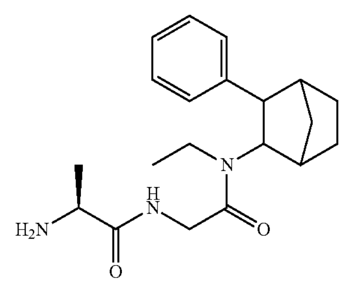 [SMILES: CCN(C(=O)CNC(=O)[C@H](C)N)C1C2CCC(C2)C1c1ccccc1] |
| PRX-P6-007 | (−) | N-(N6-Lysyl-lysyl)-(−)-N-athyl-3-phenylbicyclo[2.2.1]heptan-2-amine | 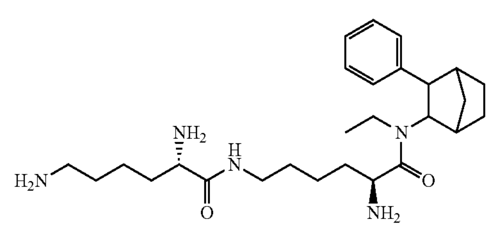 [SMILES: CCN(C(=O)[C@@H](N)CCCCNC(=O)[C@@H](N)CCCCN)C1C2CCC(C2)C1c1ccccc1] |
| PRX-P6-011 | (+) | N-(Valyl-valyl)-(+)-N-ethyl-3-phenylbicyclo[2.2.1]heptan-2-amine | 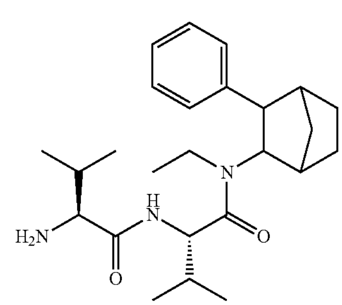 [SMILES: CCN(C(=O)[C@@H](NC(=O)[C@@H](N)C(C)C)C(C)C)C1C2CCC(C2)C1c1ccccc1] |

EXAMPLES

Preparation of Compounds of Formula (I)

Example 1. PRX-001

(Exo-phenyl,endo-amino)-n-ethyl-3-phenylbicyclo[2.2.1]heptan-2-amine (Also Known as N-Ethyl-(3-phenyl-bicyclo[2.2.1]hept-2-yl)-amine)

Fencamfamine ((Exo-phenyl,endo-amino)-N-Ethyl-3-phenylbicyclo[2.2.1]heptan-2-amine, PRX-001) was synthesized according to the scheme 1 and modifications of the methods described in *Pharmaceutical Chemistry Journal* 2011, 45(7), 419-422, *Journal of Organic Chemistry* 1961, 26, 5247-5249, GB 913866, *Organometallics*, 2013, 32, 1609-1619, and *Organic Letters* 2007, 9, 2819,

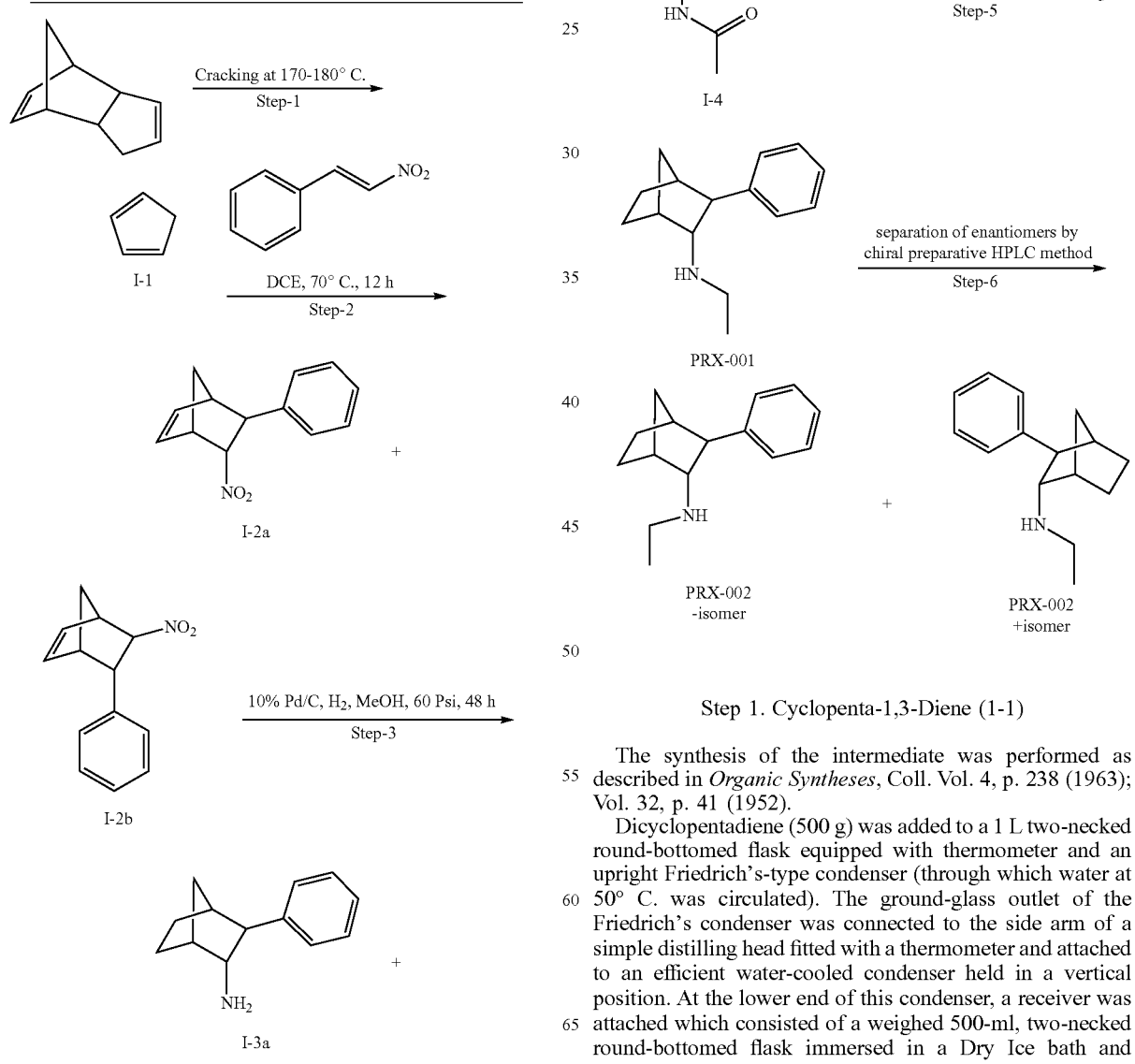

Step 1. Cyclopenta-1,3-Diene (1-1)

The synthesis of the intermediate was performed as described in *Organic Syntheses*, Coll. Vol. 4, p. 238 (1963); Vol. 32, p. 41 (1952).

Dicyclopentadiene (500 g) was added to a 1 L two-necked round-bottomed flask equipped with thermometer and an upright Friedrich's-type condenser (through which water at 50° C. was circulated). The ground-glass outlet of the Friedrich's condenser was connected to the side arm of a simple distilling head fitted with a thermometer and attached to an efficient water-cooled condenser held in a vertical position. At the lower end of this condenser, a receiver was attached which consisted of a weighed 500-ml, two-necked round-bottomed flask immersed in a Dry Ice bath and protected from the air by a calcium chloride drying tube.

The flask containing dicyclopentadiene was heated by means of oil bath until cyclopentadiene distilled (approximately 160-170° C.) into the receiver which was placed in dry ice cooling bath. After two-third of the dicyclopentadiene had been pyrolyzed during the course of 4-5 hours, the residue in the flask may tend to become viscous and a higher temperature for pyrolysis will be required in order to obtain rapid distillation of cyclopentadiene in such case it was desirable to discard the residue while it was still hot and mobile. The distilled cyclopentadiene (I-1) (200 g, 40%) was obtained as a colorless liquid and which was taken for next step immediately to avoid dimerization.

Step 2. 5-Nitro-6-Phenyl-Bicyclo[2.2.1]Hept-2-Ene (I-2A and I-2B)

To a stirred solution of β-Nitro styrene (500 g, 3.352 mol) in dichloroethane (1 L) was added freshly distilled cyclopentadiene (I-1) (800 mL) and pale yellow colored reaction mixture was stirred for 12 h under argon atmosphere at 70° C. After the completion of reaction (TLC eluent: 5% EtOAc in petroleum ether), the reaction mixture was concentrated under reduced pressure. The residue thus obtained was purified by column chromatography over 60-120 silica gel (4.5 Kg) using 1% EtOAc in petroleum ether to afford the mixture of intermediates I-2a and I-2b as a thick pale yellow colored liquid (680 g, 94%).

$^1$H-NMR (CDCl$_3$, 400 MHz) δ 7.39-7.19 (m, 5H), 6.63-6.61 (dd, J=3.2 Hz & 5.6 Hz, 1H), 6.15-6.13 (m, 1H), 5.03-5.01 (t, J=4 Hz, 1H), 3.63-3.62 (m, 1H), 3.50-3.46 (d, J=4 Hz, 1H), 3.20-3.19 (d, J=1.6 Hz, 1H), 1.92-1.89 (m, 1H), 1.78-1.74 (m, 1H).

Step 3. (Exo-Phenyl,Endo-Amino)-3-Phenylbicyclo [2.2.1]Heptan-2-Amine (1-3A)

In an autoclave hydrogenation apparatus, to the solution of the mixture of I-2a and I-2b (600 g, 2.787 mol) in methanol (6 L) was added 10% Pd/C (120 g) and the reaction mixture was stirred for 32 hours under H$_2$ pressure of 5 Kg/m$^2$. The reaction was monitored by TLC (TLC eluent: 5% MeOH in CH$_2$Cl$_2$). After the completion of reaction, the reaction mixture was filtered through Celite and the filtrate was concentrated under reduced pressure to give an 80:20 mixture of the (Exo-phenyl,endo-amino) and (Endo-phenyl,exo-amino) isomers with Rf values of 0.35 and 0.2, respectively (CH2Cl2-MeOH, 90:10, eluted twice). The crude residue obtained was purified by chromatography on silica gel (15×60 cm, 230-400 mesh) using 1.5% methanolic ammonia in dichloromethane as eluent and rechromatographed on the same column to give intermediate I-3a as a thick pale yellow colored liquid (280 g, 54% yield).

$^1$H-NMR (DMSO, 400 MHz) δ 7.26-7.23 (m, 4H), 7.16-7.12 (m, 1H), 3.05-3.02 (m, 1H), 2.22-2.21 (d, J=3.6 Hz, 1H), 2.06-2.05 (m, 1H), 1.98-1.96 (dd, J=2 Hz & 5.6 Hz, 1H), 1.89-1.83 (m, 1H), 1.65-1.51 (m, 4H), 1.37-1.26 (m, 3H).

[M+H]$^+$=188.1; HPLC Purity: 94.6%.

Step 4. (Exo-Phenyl,Endo-Amino)-N-Acetyl-3-Phenylbicyclo[2.2.1]Heptan-2-Amine (I-4)

To a solution of I-3a (50 g, 0.266 mol) in CH$_2$Cl$_2$ (350 mL) was added triethylamine (75 mL, 0.533 mol) at ambient temperature. After 10 min stirring, acetyl chloride (23 mL, 0.320 mol) was added dropwise at 0° C. and stirring was continued further for a period of 1 h. After the completion of reaction, reaction mixture was quenched with water (500 mL) and the product was extracted with DCM (2×200 mL). The organic layer was treated with 1.5N HCl (2×100 mL), sat·NaHCO$_3$ (2×100 mL), brine (2×100 mL), dried over anhydrous Na$_2$SO$_4$ and concentrated under reduced pressure to afford yellow crude semi solid intermediate 6. Further it was triturated with diethyl ether (10×500 mL) to obtain 1-4 as a pure off white solid (47 g, 82% yield), mp 159-161° C.

$^1$H NMR (CDCl$_3$, 400 MHz) δ 7.31-7.24 (m, 4H), 7.21-7.18 (m, 1H), 5.68 (s, 1H), 4.35-4.32 (m, 1H), 2.61 (s, 1H), 2.40-2.39 (d, J=3.2 Hz, 1H), 2.22-2.21 (d, J=4.8 Hz, 1H), 2.0 (s, 3H), 1.87-1.64 (m, 2H), 1.57-1.51 (m, 2H), 1.45-1.35 (m, 2H).

[M+H]$^+$=230.3, HPLC purity: 98.5%

Step 5: (Exo-Phenyl,Endo-Amino)-N-Ethyl-3-Phenylbicyclo[2.2.1]Heptan-2-Amine (PRX-001)

To a stirred suspension of lithium aluminum hydride (30 g, 0.348 mol) in dry THF (200 mL) was added dropwise a solution of I-4 (40 g, 0.174 mol) dry THF (200 mL) at 0° C. After addition, the reaction mixture was refluxed at 70° C. for 16 h under argon atmosphere. After the completion of the reaction (TLC eluent: 70% EtOAc in petroleum ether), the reaction mixture was added dropwise to an ice cold solution of 4N NaOH (2 L) solution with stirring. After complete quenching, it was filtered through Celite. The filtrate was extracted with EtOAc (3×400 mL) and washed with brine (2×200 mL). The organic layer was dried over anhydrous sodium sulfate and concentrated under reduced pressure to obtain crude PRX-001, (33 g) as a pale yellow liquid.

To a solution of crude PRX-001 (33 g) in diethyl ether (66 mL) was added ethereal HCl (130 mL) at 0° C. After 1 h, the off-white precipitate. was collected, washed with excess of diethyl ether and dried under vacuum. The obtained solid was dissolved in EtOAc (200 mL), basified with 2N NaOH solution. The separated organic layer was treated with brine (2×100 mL), dried over anhydrous sodium sulfate and concentrated under reduced pressure to obtain PRX-001 as a pure pale yellow liquid (30 g, 81% yield).

$^1$H-NMR (CDCl$_3$, 400 MHz) δ 7.30-7.28 (m, 4H), 7.21-7.17 (m, 1H), 3.17-3.14 (m, 1H), 2.59-2.49 (q, 2H), 2.42 (s, 1H), 2.26-2.25 (d, J=4 Hz, 1H), 2.16-2.15 (m, 1H), 1.79-1.74 (m, 2H), 1.68-1.59 (m, 3H), 1.47-1.38 (m, 2H), 1.09 (t, 3H).

[M+H]$^+$=216.0; HPLC purity: 94.3%

Example 2: (+)- and (−)-(Exo-phenyl,endo-amino)-n-ethyl-3-phenylbicyclo[2.2.1]heptan-2-amine, (+)-PRX-002 and (−)-PRX-002 (Also Known as. N-ethyl-(3-phenyl-bicyclo[2.2.1]hept-2-yl)-amine)

Racemic PRX-001 (90 g in 200 mg batches) was resolved by chiral preparative HPLC on a Chiralpak AD column (250×50 mm) eluted with 0.1% diethylamine in isopropanol (43 mL/min) to afford the two enantiomers, (+)-PRX-002 (37 g), and (−)-PRX-002 (39 g).

PRX-002 (+ isomer): 1H-NMR (CDCl3, 400 MHz) δ 7.30-7.27 (m, 4H), 7.21-7.17 (m, 1H), 3.17-3.15 (m, 1H), 2.59 (q, 2H), 2.42 (s, 1H), 2.27-2.26 (d, J=4 Hz, 1H), 2.16-2.15 (dd, J=2 Hz & 5.6 Hz, 1H), 1.77-1.74 (m, 2H), 1.65-1.61 (m, 1H), 1.48-1.41 (m, 3H), 1.36-1.32 (m, 1H), 1.06 (t, 3H).

[M+H]$^+$=216.3;

HPLC Retention Time (min)=4.42, purity 97.7%

Chiral HPLC Retention Time (min) 12.63, purity 99.6%

[α]20 D: +52.76° (sample concentration: 0.16% in MeOH)

PRX-002 (− isomer): 1H-NMR (CDCl₃, 400 MHz) δ 7.30-7.27 (m, 4H), 7.21-7.17 (m, 1H), 3.17-3.15 (m, 1H), 2.59 (q, 2H), 2.42 (s, 1H), 2.27-2.26 (d, J=4 Hz, 1H), 2.16-2.15 (dd, J=2 Hz & 5.6 Hz, 1H), 1.77-1.74 (m, 2H), 1.65-1.61 (m, 1H), 1.48-1.41 (m, 3H), 1.36-1.32 (m, 1H), 1.06 (t, 3H).

[M+H]⁺=216.3

HPLC Ret. Time (min) 4.426, purity 95.5%

Chiral HPLC Ret. Time (min) 14.437, purity 97.3%

[α]20D: −49.70° (sample concentration: 0.17% in MeOH)

The HCl salt of (+)-PRX-002 (120 mg) was dissolved in warm methanol (0.1 mL) and water (0.2 mL), then allowed to cool to room temperature. A resulting rectangular crystal was analyzed by X-ray crystallography which indicated the absolute configuration indicated in Scheme 1 for (+)-fencamfamine. The structures presented herein are from the same compounds as initially tested in the examples, updated after X-ray crystallography was performed.

Example 3. PRX-P1-001

N-Succinyl-N-ethyl-3-phenylbicyclo[2.2.1]heptan-2-amine (Also Known as N-Ethyl-N-(3-phenyl-bicyclo[2.2.1]hept-2-yl)-succinamic Acid)

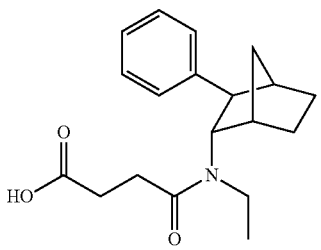 [SMILES: CCN(C(=O)CCC(=O)O)C1C2CCC(C2)C1c1ccccc1]

SCHEME 2: THE SYNTHESIS OF PRX-P1-001

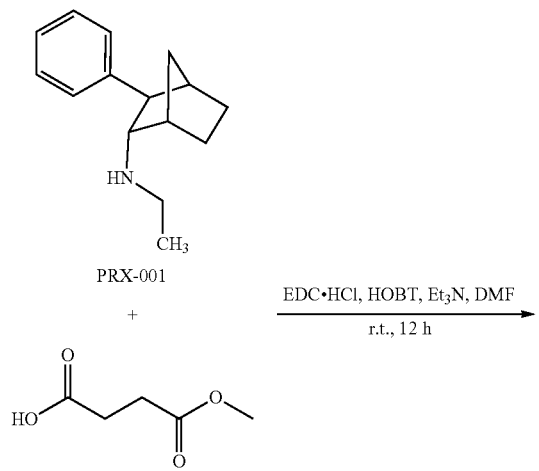

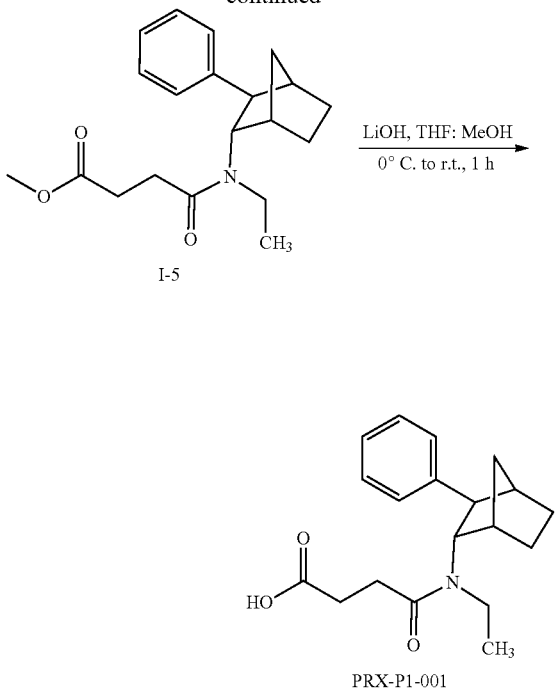

To a stirred solution of mono methyl succinate (0.92 g, 6.96 mmol) in DMF (10 mL, 10 volumes) was added EDC·HCl (1.33 g, 6.96 mmol), HOBT (0.94 g, 6.96 mmol) and triethylamine (1.29 mL, 9.28 mmol) at ambient temperature. After 10 min, N-ethyl-3-phenylbicyclo[2.2.1]heptan-2-amine (PRX-001) (1 g, 4.64 mmol) dissolved in DMF (2 mL, 2 volumes) was added dropwise and reaction mixture was further stirred for 12 h at ambient temperature. After the completion of reaction (TLC eluent: 70% EtOAc in petroleum ether), the reaction mixture was quenched with water (200 mL) and product was extracted with EtOAc (2×50 mL). The combined organic layer was washed with brine solution (50 mL), dried over anhydrous Na₂SO₄ and concentrated under reduced pressure. The residue thus obtained was purified by flash column chromatography with silica gel 60-120 mesh (12% EtOAc in petroleum ether) to obtain 1-5 (1.14 g, 75%).

To a stirred solution of 1-5 (0.85 g, 2.60 mmol) in a mixture of THF and MeOH (1:1, 20 mL) was added LiOH (0.32 g, 7.80 mmol) in water at 0° C. and reaction mixture was stirred for 1 hour. After the completion of reaction (70% EtOAc in petroleum ether), the reaction mixture was treated with 10% aqueous ammonium chloride solution (100 mL), extracted with EtOAc (2×50 mL). The combined organic layer was washed with brine (30 mL), dried over anhydrous Na₂SO₄ and concentrated under reduced pressure. The residue thus obtained was purified by flash column chromatography over silica gel 60-120 mesh using 2% of MeOH in dichloromethane to obtain (PRX-P1-001) as a sticky off white solid (0.57 g, 70%).

¹H-NMR (CDCl₃, 400 MHz) δ 7.31-7.19 (m, 5H), 4.74 (s, 1H), 4.15 (s, 1H), 3.99-3.96 (m, 1H), 3.63-3.55 (m, 1H), 3.39-3.37 (m, 1H), 3.18-3.13 (m, 1H), 2.90-2.42 (m, 4H), 1.84-1.67 (m, 4H), 1.54-1.50 (m, 2H), 1.37 (t, J=6.7 Hz, 3H).

[M−H]⁻=314.0

Example 4. General Synthetic Procedure for PRX-P1-005, PRX-P1-006, PRX-P1-012, and PRX-P1-013

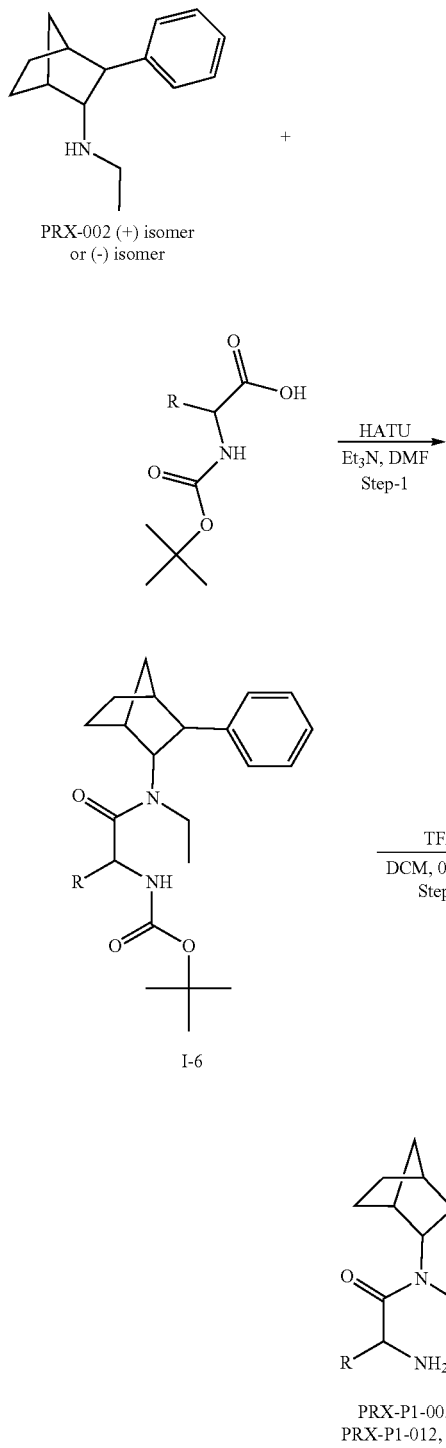

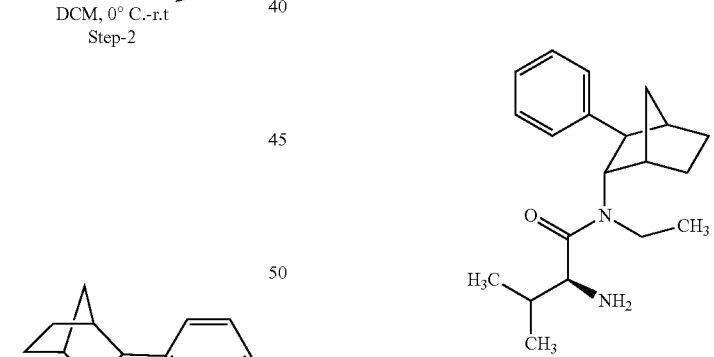

Step 1: To a solution of N-Boc protected amino acids (1.2 eq) in DMF (5 volumes) was added HATU (1.5 eq), Et₃N (2 eq) and stirred the reaction mixture for 20 min. Then, PRX-002 (+) isomer or (−) isomer (1 eq) in DMF (5 volumes) was added dropwise and the reaction was continued for 12 hour at ambient temperature. After the completion of reaction (TLC eluent: 40% EtOAc in petroleum ether), the reaction product was treated with ice cold water (20 volumes) and product was extracted with ethyl acetate (2×10 volumes). The combined organic layer was washed with 3% citric acid solution (2×10 volumes), saturated NaHCO₃ solution (2×10 volumes) and brine solution (1 volume). The obtained organic layer was dried over anhydrous sodium sulfate, concentrated under reduced pressure. The crude product thus obtained was purified by using flash column chromatography to obtain intermediate I-6.

Step 2: To a solution of I-6 (1 eq) in DCM (5 volumes) was added TFA (1 volume) dropwise at 0-5° C. and after complete addition, reaction mixture was stirred for 30 min at ambient temperature. After the completion of reaction (TLC eluent: 80% EtOAc in n-hexane), the solvent was concentrated under reduced pressure. The residue thus obtained was washed with n-hexane (2×20 volumes) for removal of impurities. Then it was dissolved in ethyl acetate (2×20 volumes), neutralized with saturated NaHCO₃ solution (20 volumes) and washed with brine solution (20 volumes). After separation, the organic layer was dried over anhydrous sodium sulfate and concentrated under reduced pressure to afford amino acid bonded prodrugs, including compounds PRX-P1-005, PRX-P1-006, PRX-P1-012, and PRX-P1-013.

Example 5. PRX-P1-006

N-Valyl-N-ethyl-3-phenylbicyclo[2.2.1]heptan-2-amine (Also Known as (S)-2-amino-N-ethyl-3-methyl-N-(3-phenylbicyclo[2.2.1]heptan-2-yl)butanamide)

Using the general procedure described in Example 4 above employing PRX-001 (±) isomers, (500 mg, 2.32 mmol) and (S)-2-(Boc-amino)-3-methylbutyric acid (504 mg, 2.32 mmol), provided the product (PRX-P1-006) (460 mg, 64% yield) as a brownish liquid. 1H-NMR (CDCl₃, 400 MHz) δ 7.33-7.18 (m, 5H), 4.80-4.78 (m, 1H), 4.51 (s, 1H), 4.14 (s, 1H), 3.61-3.31 (m, 1H), 3.09-3.08 (m, 1H), 2.97-2.91 (m, 1H), 2.50-2.41 (m, 2H), 3.00-2.90 (m, 2H), 2.71-2.66 (m, 1H), 2.44-2.28 (m, 2H), 1.66-1.61 (m, 2H), 1.42-1.36 (m, 1H), 1.26-1.19 (m, 6H), 1.01 (t, J=5.6 Hz, 3H)

$[M+H]^+$=315.4

Example 6. PRX-P1-005

N-Lysyl-(−)-N-ethyl-3-phenylbicyclo[2.2.1]heptan-2-amine (Also Known as (S)-2,6-diamino-N-ethyl-N-(3-phenylbicyclo[2.2.1]heptan-2-yl)hexanamide)

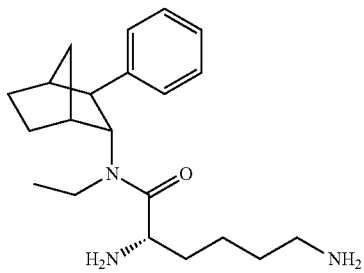 [SMILES: CCN(C(=O)[C@@H](N)CCCCN)C1C2CCC(C2)C1c1ccccc1]

Using the general procedure described in Example 4 above employing PRX-002 (−) isomer, (200 mg, 0.92 mmol) and (S)-2,6-bis-tert-butoxycarbonylamino-hexanoic acid (386 mg, 1.11 mmol), provided the product (PRX-P1-005) (160 mg, 160 mg % yield) as a pale yellow liquid.

$^1$H-NMR (DMSO, 400 MHz) δ 8.34 (s, 2H), 7.33-7.18 (m, 5H), 4.60 (s, 1H), 4.38 (s, 1H), 4.06 (s, 1H), 3.82-3.78 (m, 1H), 3.64-3.35 (m, 4H), 3.33-3.29 (m, 2H), 3.00-2.90 (m, 2H), 2.71-2.66 (m, 1H), 2.44-2.28 (m, 2H), 1.66-1.61 (m, 2H), 1.50-1.45 (m, 2H), 1.42-1.36 (m, 2H), 1.26-1.19 (m, 2H), 1.01 (t, J=5.6 Hz, 3H)

[M+H]$^+$=344.5

Example 7. PRX-P1-012

N-Glycyl-(−)-N-ethyl-3-phenylbicyclo[2.2.1]heptan-2-amine (Also Known as 2-Amino-N-ethyl-N-(3-phenyl-bicyclo [2.2.1]hept-2-yl)-acetamide)

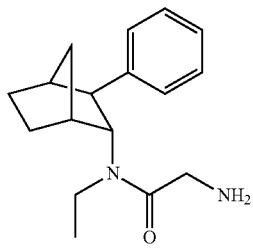 [SMILES: CCN(C(=O)CN)C1C2CCC(C2)C1c1ccccc1]

Using the general procedure described in Example 4 above employing PRX-002 (−) isomer, (500 mg, 2.32 mmol) and N-(tert-butoxycarbonyl)glycine (487 mg, 2.78 mmol), provided the product (PRX-P1-012) (420 mg, 68% yield) as a yellow liquid.

$^1$H-NMR (CDCl$_3$, 400 MHz) δ 7.38-7.25 (m, 4H), 7.23-7.11 (m, 1H), 4.58-4.57 (m, 1H), 4.42-4.40 (m, 1H), 3.32-3.21 (m, 1H), 2.93-2.92 (m, 1H), 2.32-2.31 (m, 1H), 1.66-1.57 (m, 5H), 1.48-1.40 (m, 2H), 1.23-1.18 (m, 2H), 1.00 (t, J=5.6 Hz, 3H)

[M+H]$^+$=273.3

Example 8. PRX-P1-013

N-Phenylalanyl-(−)-N-ethyl-3-phenylbicyclo[2.2.1]heptan-2-amine (Also Known as (S)-2-Amino-N-ethyl-3-phenyl-N-(3-phenyl-bicyclo [2.2.1]hept-2-yl)-propionamide)

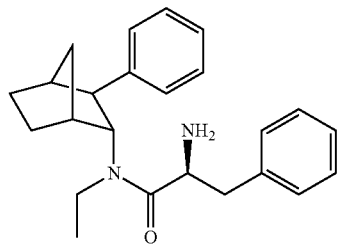 [SMILES: CCN(C(=O)[C@@H](N)Cc1ccccc1)C1C2CCC(C2)C1c1ccccc1]

Using the general procedure described in Example 4 above employing PRX-002 (−) isomer, (0.7 g, 3.25 mmol) and N-(tert-butoxycarbonyl)-L-phenylalanine (1 g, 3.90 mmol), provided the product (PRX-P1-013), (0.73 g, 62% yield as a yellow liquid. 1H-NMR (CDCl$_3$, 400 MHz) δ 7.26-6.99 (m, 10H), 4.80-4.78 (m, 1H), 4.67-4.56 (m, 1H), 4.05-4.00 (m, 1H), 3.61-3.11 (m, 2H), 3.09-2.80 (m, 5H), 2.50-2.41 (m, 2H), 1.66-1.61 (m, 1H), 1.42-1.36 (m, 1H), 1.26-1.19 (m, 1H), 1.01 (t, J=5.6 Hz, 3H)

[M+H]$^+$=363.1

Example 9. PRX-P2-001

N-Ethoxycarbonyl-N-ethyl-3-phenylbicyclo[2.2.1]heptan-2-amine (Also Known as Ethyl N-ethyl-3-phenylbicyclo[2.2.1]heptan-2-yl)carbamate)

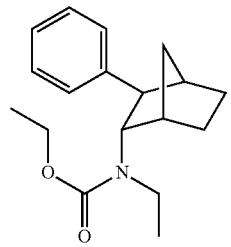 [SMILES: CCOC(=O)N(CC)C1C2CCC(C2)C1c1ccccc1]

To a solution of PRX-001 (200 mg, 0.93 mmol) in DCM (2 mL, 10 volumes) was added Et$_3$N (0.25 mL, 1.86 mmol) and reaction mixture was cooled to 0° C. After 5 minutes stirring, ethyl chloroformate (0.1 mL, 1.11 mmol) was added dropwise and then the reaction mixture was stirred at ambient temperature for 16 hours. After the completion of reaction (TLC eluent: 60% EtOAc in petroleum ether), the reaction mixture was concentrated to dryness and then dissolved in ethyl acetate (50 mL), washed with water (2×20 mL) and brine solution (20 mL). The organic layer was dried over anhydrous sodium sulfate, concentrated under reduced pressure. The crude product obtained was purified by flash column chromatography with silica (60-120) mesh using 10-12% EtOAc in hexane as eluent to obtain the product (PRX-P2-001) as pale yellow liquid (106 mg, 40%).

1H-NMR (CDCl$_3$, 400 MHz) δ 7.33-7.27 (m, 4H), 7.22-7.17 (m, 1H), 4.39-4.37 (m, 1H), 4.19-4.09 (m, 2H), 3.69-3.56 (m, 1H), 3.25-3.17 (m, 1H), 2.86-2.85 (d, J=6 Hz, 1H), 2.60 (s, 1H), 2.44-2.43 (d, J=3.2 Hz, 1H), 1.77-1.63 (m, 2H), 1.54-1.43 (m, 3H) 1.29-1.23 (m, 4H), 1.10 (t, J=7.2 Hz, 3H)
[M+H]⁺=288.4

Example 10. General Synthetic Procedure for PRX-P3-002 and PRX-P3-004

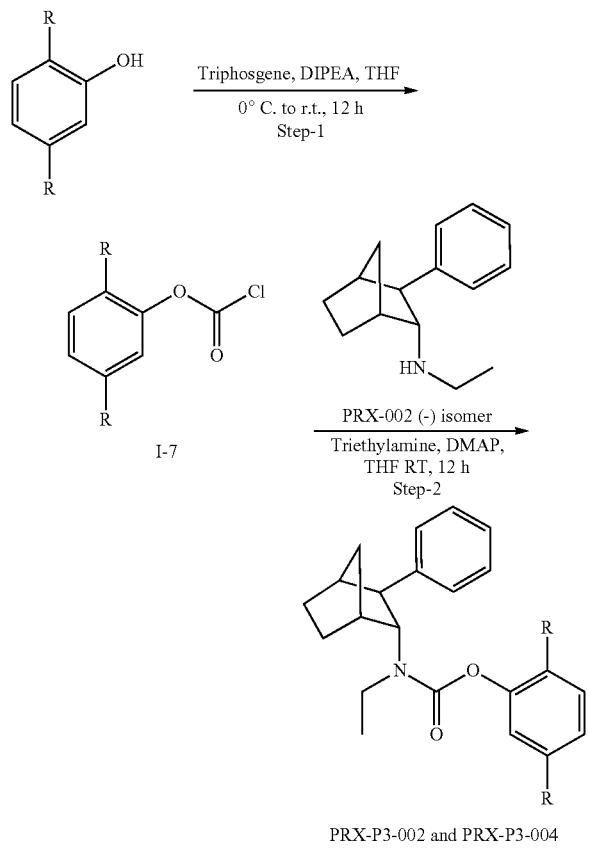

SCHEME 4. THE SYNTHESIS OF ARYL CARBAMATE LINKED PRODRUGS

PRX-P3-002 and PRX-P3-004

Step 1: To a stirred solution of triphosgene (0.5 eq) in THF (5 volumes) at 0° C., was added dropwise a solution of phenol derivative (1 eq) and DIPEA (1 eq) in THF (5 volumes) and the reaction mixture was kept at ambient temperature for 12 hours. After the completion of reaction (TLC eluent: 10% EtOAc in hexane), the reaction mixture was treated with water (20 volumes) and product was extracted with EtOAc (2×20 volumes). The combined organic layer were dried over anhydrous sodium sulfate, filtered and concentrated under reduced pressure to obtain crude intermediate I-7, which was carried forwarded for the next step.

Step 2: To a stirred solution of (−)-PRX-002 (1 eq) in dry THF (5 volumes), were added DMAP (0.1 eq) and Et₃N (2 eq). The mixture was stirred for 10 min at ambient temperature. Then a solution of I-7 (2 eq) in THF (5 volumes) was added dropwise and the reaction mixture was stirred for 12 hours at ambient temperature and monitored TLC (eluent: 5% EtOAc in hexane). Then, the reaction mixture was treated with water (20 volumes), and extracted with EtOAc (2×30 volumes). The organic layer was washed with brine (20 volumes), dried over anhydrous sodium sulfate and concentrated under reduced pressure. The residue thus obtained was purified by preparative HPLC method to afford aryl carbamate linked prodrug, including Compounds PRX-P3-002 and PRX-P3-004. For the present example, R denotes the atoms for the noted compounds PRX-P3-002 and PRX-P3-004.

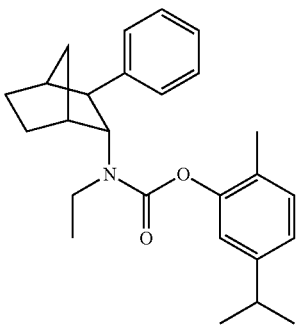 [SMILES: CCN(C(=O)Oc1cc(C(C)C)ccc1C)C1C2CCC(C2)C1c1ccccc1]

Example 11. (PRX-P3-002)

N-(5-Isopropyl-2-methylphenoxycarbonyl)-(−)-N-ethyl-3-phenylbicyclo[2.2.1]heptan-2-amine (Also Known as 5-isopropyl-2-methylphenyl N-ethyl-(3-phenylbicyclo[2.2.1]heptan-2-yl)carbamate)

Using the general procedure described in Example 10 above employing PRX-002 (−) isomer, (250 mg, 1.17 mmol) and carvacrol (400 mg, 2.66 mmol), provided the product (PRX-P3-002) (337 mg, 75% yield) as a colorless liquid.

¹H-NMR (CDCl₃, 400 MHz) δ 7.34-7.30 (m, 4H), 7.24-7.21 (m, 1H), 7.13-7.11 (d, J=8 Hz, 1H), 6.99-6.96 (m, 1H), 6.91 (s, 1H), 4.49 (s, 1H), 3.76-3.71 (m, 1H), 3.40-3.35 (m, 1H), 2.99 (s, 1H), 2.90-2.84 (m, 1H), 2.74 (s, 1H), 2.48 (s, 1H), 2.14 (s, 3H), 1.81-1.70 (m, 3H), 1.60-1.52 (m, 2H), 1.31-1.19 (m, 10H).
[M+H]⁺=392.2

Example 12. PRX-P3-004

N-(2-Isopropyl-5-methylphenoxycarbonyl)-(−)-N-ethyl-3-phenylbicyclo[2.2.1]heptan-2-amine (Also Known as 2-Isopropyl-5-methylphenyl N-ethyl-(3-phenylbicyclo[2.2.1]heptan-2-yl)carbamate)

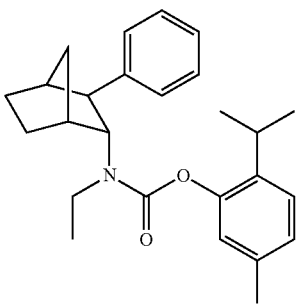 [SMILES: CCN(C(=O)Oc1cc(C)ccc1C(C)C)C1C2CCC(C2)C1c1ccccc1]

Using the general procedure described in Example 10 above employing PRX-002 (−) isomer, (250 mg, 1.17 mmol)

and thymol (400 mg, 2.66 mmol), provided the product (PRX-P3-004) (351 mg, 78% yield) as a transparent liquid.

$^1$H NMR (CDCl$_3$, 400 MHz) δ 7.34-7.33 (m, 4H), 7.23-7.22 (m, 1H), 7.17 (d, J=7.6 Hz, 1H), 6.99 (d, J=7.6 Hz, 1H), 6.87 (s, 1H), 4.49 (s, 1H), 3.75-3.70 (m, 1H), 3.38 (s, 2H), 3.00 (s, 2H), 2.71 (s, 1H), 2.49 (s, 1H), 2.31 (s, 3H), 1.81-1.70 (m, 3H), 1.56-1.55 (m, 1H), 1.31-1.17 (m, 10H). [M+H]$^+$=392.2

Example 13. General Synthetic Procedure for PRX-P4-002, PRX-P4-005, and PRX-P4-004

SCHEME 4.1. THE SYNTHESIS OF ACYLOXYMETHOXYCARBONYL (ALSO KNOWN AS ACYLOXY METHYL ESTER LINKED) PRODRUGS

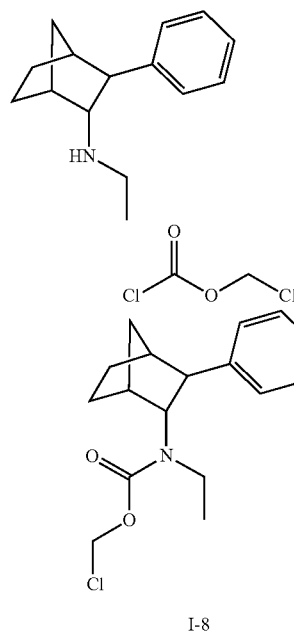

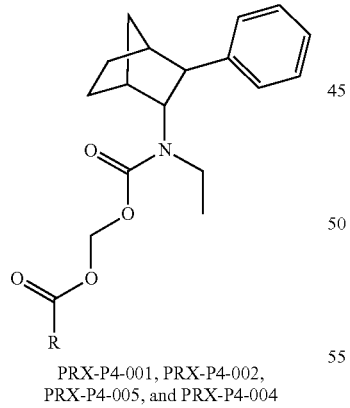

PRX-P4-001, PRX-P4-002, PRX-P4-005, and PRX-P4-004

Step 1: To a solution of N-ethyl-3-phenylbicyclo[2.2.1]heptan-2-amine (PRX-002) (1 eq) in dichloromethane (10 volumes) under argon atmosphere, was added triethylamine (2 eq) dropwise at ambient temperature and the mixture was stirred for 5 min. Then, chloromethyl chloroformate (1.5 eq) was introduced dropwise at 0-5° C. and the reaction mixture was further stirred at ambient temperature for 30 min. After the completion of reaction (TLC eluent: 20% EtOAc in petroleum ether), the reaction mixture was quenched in water (20 volumes), extracted with dichloromethane (2×20 volumes). The combined organic layer was washed with water (2×20 volumes), brine (20×1 volumes) solution, filtered, dried over anhydrous sodium sulfate and concentrated under reduced pressure to obtain N-(Chloromethoxycarbonyl)-N-ethyl-3-phenylbicyclo[2.2.1]heptan-2-amine (1-8) as a thick brown liquid, which was used in the next step without further purification.

Step 2: To a solution of N-(Chloromethoxycarbonyl)-N-ethyl-3-phenylbicyclo[2.2.1]heptan-2-amine (Also Known as ethyl-(3-phenyl-bicyclo[2.2.1]hept-2-yl)-carbamic acid chloromethyl ester) (1-8) (1 eq) in DMF (10 volumes) was added dry Cs$_2$CO$_3$ (2 eq), acid (R—COOH) (2 eq), and KI (0.2 eq) at ambient temperature. The reaction mixture was heated to 100-105° C. and stirred for 4 h. After completion of reaction (TLC eluent: 10% EtOAc in n-hexane), the reaction mixture was quenched in water (20 volumes), extracted with ethyl acetate (2×20 volumes). Combined organic layer was washed with water (2×10 volumes), brine solution (10 volumes), filtered, dried over anhydrous sodium sulfate and concentrated under reduced pressure. The crude residue obtained was purified by flash column chromatography or preparative HPLC to yield acyloxymethoxycarbonyl pro-drugs of PRX-002, including PRX-P4-002, PRX-P4-005, and PRX-P4-004. For the present example, R denotes the atoms for the noted compounds PRX-P4-002, PRX-P4-005, and PRX-P4-004.

Example 14. PRX-P4-001

N-(Acetoxymethoxycarbonyl)-(−)-N-ethyl-3-phenyl-bicyclo[2.2.1]heptan-2-amine (Also Known as ((N-ethyl-(3-phenylbicyclo[2.2.1]heptan-2-yl)carbamoyl)oxy)methyl acetate)

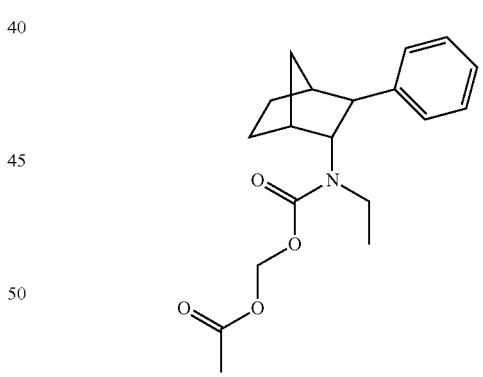

Using the general procedure described in Example 14 above employing PRX-002 (−) isomer, (200 mg, 0.92 mmol) and sodium acetate (160 mg, 1.9493 mmol), provided the product (PRX-P4-001) (132 mg, 44% yield) as a colorless liquid.

$^1$H-NMR (CDCl$_3$, 400 MHz) δ 7.31-7.27 (m, 4H), 7.22-7.21 (m, 1H), 5.80 (dd, J=5.6 & 11.6 Hz, 1H), 4.39-4.37 (m, 1H), 3.59 (brs, 1H), 3.27-3.18 (m, 1H), 2.89 (d, J=5.2 Hz, 1H), 2.61 (s, 1H), 2.43 (d, J=3.2 Hz, 1H), 2.12 (s, 3H), 1.75-1.70 (m, 2H), 1.61-1.59 (m, 1H), 1.55-1.45 (m, 3H), 1.28-1.25 (m, 1H), 1.10 (t, J=6.8 Hz, 3H)

[M+Na]$^+$=354.20

Example 15. PRX-P4-002

N-(Decanoyloxymethoxycarbonyl)-(−)-N-ethyl-3-phenylbicyclo[2.2.1]heptan-2-amine (also known as (N-ethyl-(3-phenylbicyclo[2.2.1]heptan-2-yl)carbamoyl)oxy)methyl decanoate (− isomer))

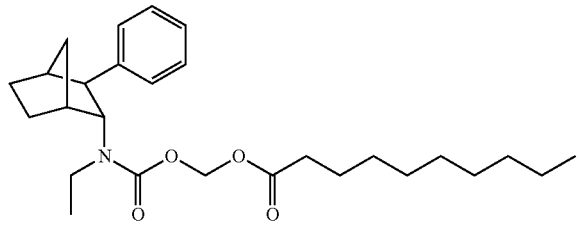 [SMILES: CCCCCCCCCC(=O)OCOC(=O)N(CC)C1C2CCC(C2)C1c1ccccc1]

Using the general procedure described in Example 14 above employing PRX-002 (−) isomer, (1.5 g, 6.96 mmol) and Decanoic acid (1.76 g, 10.23 mmol), provided the product (PRX-P4-002) (1.23 g, 40% yield) as a thick transparent liquid.

$^1$H-NMR (CDCl$_3$, 400 MHz) δ 7.33-7.27 (m, 4H), 7.22-7.18 (m, 1H), 5.87 (dd, J=5.6 & 10.8 Hz, 1H), 4.38-4.35 (m, 1H), 3.59 (brs, 1H), 3.27-3.17 (m, 1H), 2.89-2.88 (d, J=5.2 Hz, 1H), 2.61 (s, 1H), 2.43 (d, J=3.2 Hz, 1H), 2.37-2.32 (m, 2H), 1.78-1.71 (m, 2H), 1.70-1.58 (m, 3H), 1.57-1.42 (m, 1H), 1.29-1.25 (m, 15H), 1.09 (t, J=6.8 Hz, 3H), 0.90 (t, J=6.4 Hz, 3H).

[M+Na]$^+$=466.30

Example 16. Compound 15 (PRX-P4-003)

N-(Octadecanoyloxymethoxycarbonyl)-(−)-N-ethyl-3-phenylbicyclo[2.2.1]heptan-2-amine (Also Known as ((N-Ethyl-(3-phenylbicyclo[2.2.1]heptan-2-yl)carbamoyl)oxy)methyl octadecanoate)

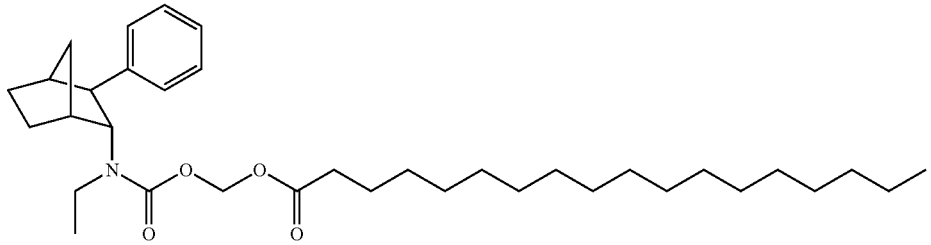 [SMILES: CCCCCCCCCCCCCCCCCC(=O)OCOC(=O)N(CC)C1C2CCC(C2)C1c1ccccc1]

Using the general procedure described in Example 14 above employing PRX-002 (−) isomer, (5 g, 23.21 mmol) and octadecanoic acid (9.7 g, 34.11 mmol), provided the product (PRX-P4-003) (4.9 g, 38% yield) as a colorless liquid.

$^1$H-NMR (CDCl$_3$, 400 MHz) δ 7.31-7.27 (m, 4H), 7.22-7.18 (m, 1H), 5.80 (dd, J=5.6 & 10.8 Hz, 1H), 4.38-4.36 (m, 1H), 3.59 (brs, 1H), 3.26-3.18 (m, 1H), 2.90 (d, J=5.6 Hz, 1H), 2.61 (s, 1H), 2.43 (d, J=3.6 Hz, 1H), 2.36-2.32 (m, 2H), 1.75-1.71 (m, 2H), 1.63-1.50 (m, 5H), 1.30-1.25 (m, 30H), 1.09 (t, J=6.8 Hz, 3H), 0.90 (t, J=6.4 Hz, 3H)

[M+Na]$^+$=578.4

Example 17. PRX-P4-004

N—((Z)-Octadec-9-enoyloxymethoxycarbonyl)-(−)-N-ethyl-3-phenylbicyclo[2.2.1]heptan-2-amine (Also Known as (Z)-Octadec-9-enoic acid [N-ethyl-(3-phenyl-bicyclo[2.2.1]hept-2-yl)-carbamoyloxy]-methyl ester)

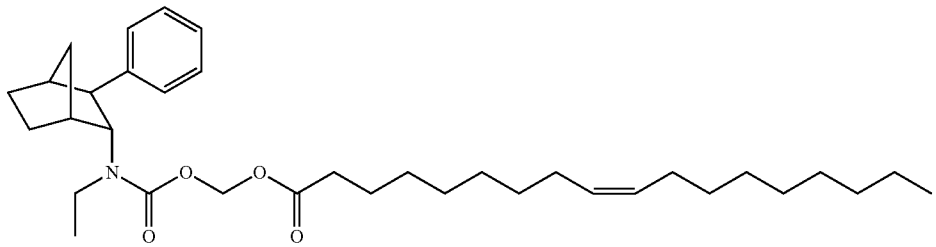 [SMILES: CCCCCCCC/C=C\CCCCCCCC(=O)OCOC(=O)N(CC)C1C2CCC(C2)C1c1ccccc1]

Using the general procedure described in Example 14 above employing PRX-002 (−) isomer, (1 g, 4.64 mmol) and oleic acid (2.56 g, 9.09 mmol), provided the product (PRX-P4-004) (0.91 g, 30% yield) as a colorless liquid.

$^1$H-NMR (CDCl$_3$, 400 MHz) δ 7.33-7.27 (m, 4H), 7.22-7.18 (m, 1H), 5.80 (dd, J=5.6 & 10.8 Hz, 2H), 5.39-5.30 (m, 2H), 4.38-4.37 (m, 1H), 3.59 (brs, 1H), 3.26-3.17 (m, 1H), 2.90 (d, J=5.6 Hz, 1H), 2.61 (s, 1H), 2.43 (d, J=3.6 Hz, 1H), 2.34 (t, J=7.6 Hz, 2H), 2.01-1.98 (m, 3H), 1.78-1.74 (m, 2H), 1.63-1.51 (m, 4H), 1.28-1.25 (m, 23H), 1.09 (t, J=6.8 Hz, 3H), 0.90 (t, J=6.8 Hz, 3H)

[M+H]$^+$=554.4

Example 18. General Synthetic Procedure for PRX-P5-001 to PRX-P5-011

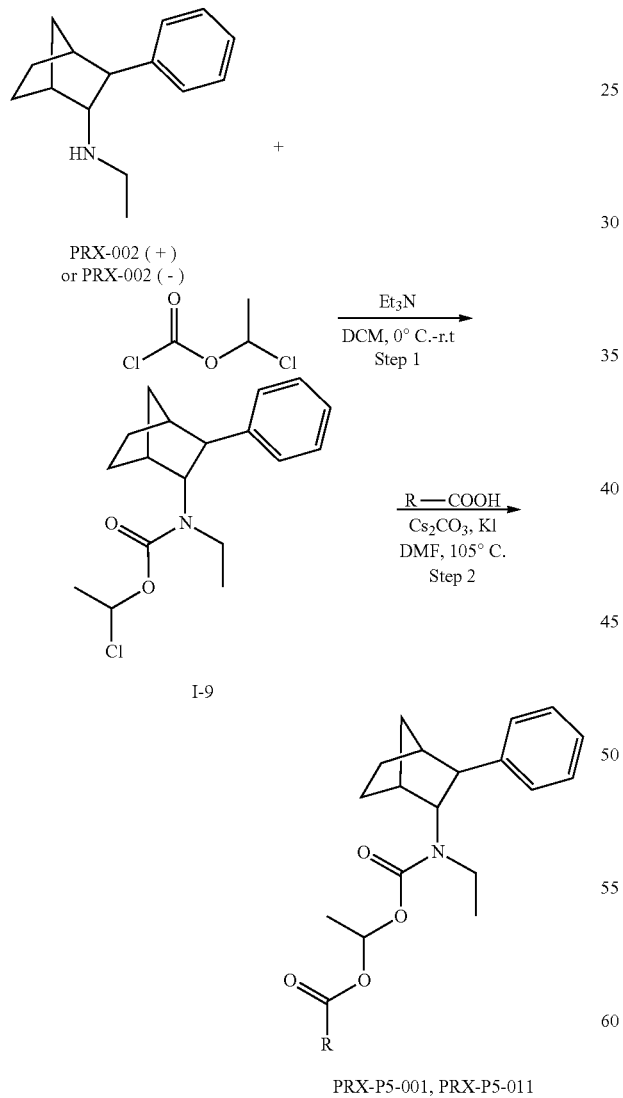

Step 1: To a solution of N-ethyl-3-phenylbicyclo[2.2.1]heptan-2-amine, PRX-002 (+) isomer or (−) isomer, (1 eq) in DCM (10 volumes) under argon atmosphere, was added triethylamine (2 eq) dropwise at ambient temperature. After stirring for 5 minutes, 1-chloroethyl chloroformate (2) (1.5 eq) was added dropwise at 0-5° C. and the reaction mixture was further stirred at ambient temperature for 30 min. After the completion of reaction (TLC eluent: 20% EtOAc in petroleum ether) the reaction mixture was quenched in water (20 volumes), extracted with DCM (2×20 volumes). The combined organic layer was washed with water and brine, dried over anhydrous sodium sulfate and concentrated under reduced pressure to obtain N-(1-Chloroethoxycarbonyl)-N-ethyl-3-phenylbicyclo[2.2.1]heptan-2-amine (1-9) as a thick brown liquid, which was carried forwarded for the next step without purification.

Step 2: To a solution of intermediate 1-9 (1 eq) in DMF (10 volumes) was added dry Cs$_2$CO$_3$ (2 eq), a fatty acid (R—COOH) (2 eq), and KI (0.2 eq) at ambient temperature and the reaction mixture was heated at 100-105° C. and stirred for 4 hours. After completion of reaction (TLC eluent: 10% EtOAc in n-Hexane), the reaction mixture was quenched in water (20 volumes), extracted with ethyl acetate (2×20 volumes). Combined organic layer was washed with water (2×10 volumes) and brine solution (10 volumes), further dried over anhydrous sodium sulfate and concentrated under reduced pressure. The crude residue obtained was purified by either flash column chromatography/preparative HPLC to yield 1-Acyloxyethoxycarbonyl prodrugs, including Compounds PRX-P5-001 to PRX-P5-011.

Example 19. PRX-P5-001)

N-(1-Acetoxyethoxycarbonyl)-(−)-N-ethyl-3-phenyl-bicyclo[2.2.1]heptan-2-amine (Also Known as Acetic Acid 1-[N-ethyl-(3-phenyl-bicyclo[2.2.1]hept-2-yl)-carbamoyloxy]-ethyl ester)

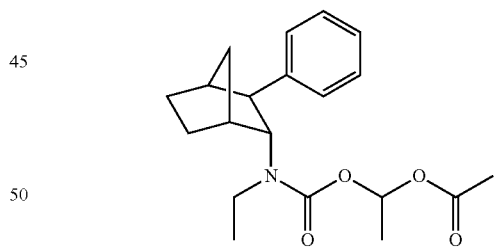

Using the general procedure described in Example 18 above employing PRX-002 (−) isomer, (200 mg, 0.92 mmol) and sodium acetate (152 mg, 1.86 mmol), provided a the product (PRX-P5-001) (89 mg, 28% yield) as a pale yellow liquid.

$^1$H-NMR (CDCl$_3$, 400 MHz) δ7.33-7.27 (m, 4H), 7.23-7.19 (m, 1H), 6.87 (q, 1H), 4.35-4.33 (m, 1H), 3.59-3.56 (m, 1H), 3.25-3.18 (m, 1H), 2.88-2.87 (d, J=5.6 Hz, 1H), 2.62 (s, 1H), 2.44-2.42 (m, 1H), 2.07 (s, 3H), 1.75-1.69 (m, 2H), 1.61-1.55 (m, 7H), 1.10 (t, J=7.2 Hz, 3H).

[M+Na]$^+$=368.2

Example 20. PRX-P5-002

N-(1-Decanoyloxyethoxycarbonyl)-(−)-N-ethyl-3-phenylbicyclo[2.2.1]heptan-2-amine (also known as Decanoic acid 1-[N-ethyl-(3-phenyl-bicyclo[2.2.1]hept-2-yl)-carbamoyloxy]-ethyl ester)

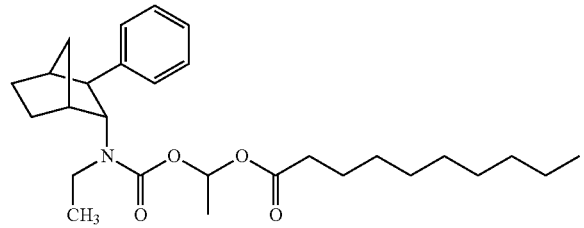 [SMILES: CCCCCCCCCC(=O)OC(C)OC(=O)N(CC)C1C2CCC(C2)C1c1ccccc1]

Using the general procedure described in Example 18 above employing PRX-002 (−) isomer, (300 mg, 1.39 mmol) and decanoic acid (482 mg, 2.80 mmol), provided the product (PRX-P5-002) (242 mg, 38% yield) as a pale yellow liquid.

$^1$H-NMR (CDCl$_3$, 400 MHz) δ 7.33-7.27 (m, 4H), 7.22-7.18 (m, 1H), 6.87-6.83 (q, J=5.2 Hz, 1H), 4.35-4.32 (m, 1H), 3.58-3.54 (m, 1H), 3.25-3.18 (m, 1H), 2.89-2.88 (d, J=6 Hz, 1H), 2.61 (s, 1H), 2.44-2.43 (m, 1H), 2.32-2.27 (m, 2H), 1.75-1.68 (m, 2H), 1.64-1.59 (m, 4H), 1.56-1.42 (m, 5H), 1.34-1.26 (m, 10H), 1.10 (t, J=6.8 Hz, 3H), 0.90 (m, 5H)

[M+Na]$^+$=480.3

Example 21. PRX-P5-003

N-(1-Butanoyloxyethoxycarbonyl)-(−)-N-ethyl-3-phenylbicyclo[2.2.1]heptan-2-amine (also known as Butyric acid 1-[N-ethyl-(3-phenyl-bicyclo[2.2.1]hept-2-yl)-carbamoyloxy]-ethyl ester)

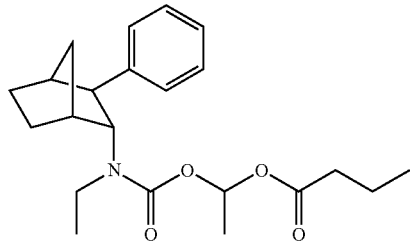 [SMILES: CCCC(=O)OC(C)OC(=O)N(CC)C1C2CCC(C2)C1c1ccccc1]

Using the general procedure described in Example 18 above employing PRX-002 (−) isomer, (330 mg, 1.55 mmol) and butanoic acid (274 mg, 3.10 mmol), provided the product (PRX-P5-003) (240 mg, 42% yield) as a yellow liquid.

$^1$H-NMR (CDCl$_3$, 400 MHz) δ7.35-7.27 (m, 4H), 7.24-7.18 (m, 1H), 6.88 (q, 1H), 4.35 (s, 1H), 3.67-3.40 (m, 1H), 3.39-3.06 (m, 1H), 2.89 (d, J=6 Hz, 1H), 2.61 (s, 1H), 2.44-2.43 (m, 1H), 2.32-2.27 (m, 2H), 1.75-1.47 (m, 9H), 1.34-1.24 (m, 2H), 1.10 (t, J=6.8 Hz, 3H), 0.90 (t, 3H)

[M+Na]$^+$=396.4

Example 22. PRX-P5-004

N-(1-Octanoyloxyethoxycarbonyl)-(−)-N-ethyl-3-phenylbicyclo[2.2.1]heptan-2-amine (also known as Octanoic A1-[N-ethyl-(3-phenyl-bicyclo[2.2.1]hept-2-yl)-carbamoyloxy]-ethyl ester)

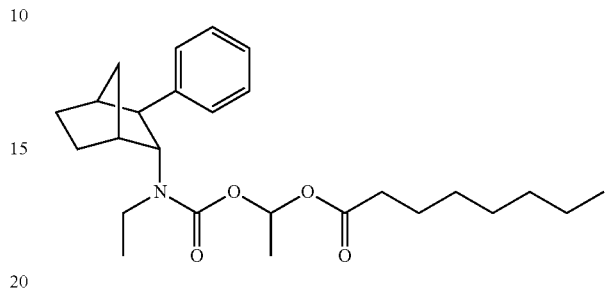

Using the general procedure described in Example 18 above employing PRX-002 (−) isomer, (330 mg, 1.55 mmol) and octanoic acid (447 mg, 3.10 mmol), provided the product (PRX-P5-004) (184 mg, 28% yield) as a yellow liquid.

$^1$H-NMR (CDCl$_3$, 400 MHz) δ 7.33-7.27 (m, 4H), 7.22-7.18 (m, 1H), 6.87-6.83 (q, J=5.6 Hz, 1H), 4.35 (d, J=5.6 Hz, 1H), 3.57-3.56 (m, 1H), 3.24-3.17 (m, 1H), 2.89 (d, J=8 Hz, 1H), 2.61 (s, 1H), 2.44-2.43 (m, 1H), 2.32-2.27 (m, 2H), 1.75-1.68 (m, 4H), 1.53-1.45 (m, 4H), 1.28-1.26 (m, 11H), 1.09 (t, J=6.8 Hz, 3H), 0.89 (t, 3H)

[M+Na]$^+$=452.60

Example 23. PRX-P5-005

N-(1-Dodecanoyloxyethoxycarbonyl)-(−)-N-ethyl-3-phenylbicyclo[2.2.1]heptan-2-amine (Also Known as Dodecanoic Acid 1-[N-ethyl-(3-phenyl-bicyclo[2.2.1]hept-2-yl)-carbamoyloxy]-ethyl ester)

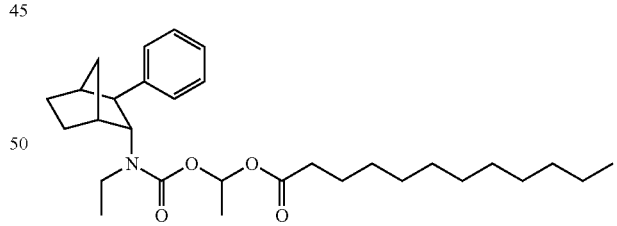

Using the general procedure described in Example 18 above employing PRX-002 (−) isomer, (330 mg, 1.55 mmol) and dodecanoic acid (622 mg, 3.10 mmol), provided the product (PRX-P5-005) (300 mg, 40% yield) as a yellow liquid.

$^1$H-NMR (CDCl$_3$, 400 MHz) δ 7.33-7.27 (m, 4H), 7.22-7.20 (m, 1H), 6.87 (q, J=5.6 Hz, 1H), 4.35-4.33 (m, 1H), 3.23-3.21 (m, 1H), 2.89 (d, J=6 Hz, 1H), 2.61 (s, 1H), 2.44-2.43 (m, 1H), 2.32-2.27 (m, 2H), 1.87-1.78 (m, 2H), 1.67-1.55 (m, 8H), 1.54-1.52 (m, 5H), 1.35-1.30 (m, 10H), 1.29 (t, 3H), 0.90-0.89 (m, 6H)

[M+Na]$^+$=508.6

Example 24. PRX-P5-006

N-(1-Octadecanoyloxyethoxycarbonyl)-(−)-N-ethyl-3-phenylbicyclo[2.2.1]heptan-2-amine (Also Known as Octadecanoic Acid 1-[N-ethyl-(3-phenyl-bicyclo[2.2.1]hept-2-yl)-carbamoyloxy]-ethyl ester)

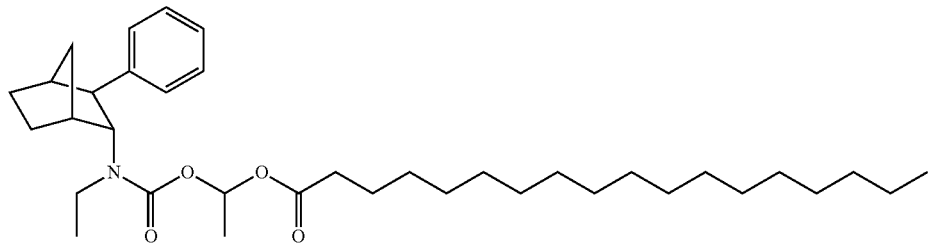 [SMILES: CCCCCCCCCCCCCCCCCC(=O)OC(C)OC(=O)N(CC)C1C2CCC(C2)C1c1ccccc1]

Using the general procedure described in Example 18 above employing PRX-002 (−) isomer, (5 g, 23.22 mmol) and octadecanoic acid (13.27 g, 46.68 mmol), provided the product (PRX-P5-006) (5.82 g, 44% yield) as a pale yellow liquid.

$^1$H-NMR (CDCl$_3$, 400 MHz) δ 7.33-7.27 (m, 4H), 7.22-7.18 (m, 1H), 6.87 (q, J=5.6 Hz, 1H), 4.35 (d, J=6 Hz, 1H), 3.57 (d, J=5.2 Hz, 1H), 3.26-3.18 (m, 1H), 2.89 (d, J=6 Hz, 1H), 2.61 (s, 1H), 2.44 (S, 1H), 2.33-2.27 (m, 2H), 1.76-1.68 (m, 2H), 1.64-1.56 (m, 4H), 1.54-1.47 (m, 5H), 1.42-1.26 (m, 23H), 1.13-1.06 (m, 5H), 0.90-0.84 (m, 6H)

[M+Na]$^+$=592.70

Example 25. PRX-P5-007

N-(1-(2,2-Dimethylpropionyloxy)ethoxycarbonyl)-(−)-N-ethyl-3-phenylbicyclo[2.2.1]heptan-2-amine (Also Known as 2,2-Dimethyl-propionic acid 1-[N-ethyl-(3-phenyl-bicyclo [2.2.1]hept-2-yl)-carbamoyloxy]-ethyl ester)

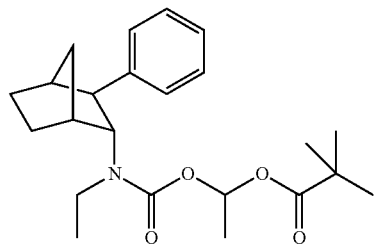 [SMILES: CCN(C(=O)OC(C)OC(=O)C(C)(C)C)C1C2CCC(C2)C1c1ccccc1]

Using the general procedure described in Example 18 above employing PRX-002 (−) isomer, (330 mg, 1.55 mmol) and pivalic acid (317 mg, 3.11 mmol), provided the product (PRX-P5-007) (236 mg, 40% yield) as a yellow liquid.

$^1$H-NMR (CDCl$_3$, 400 MHz) δ 7.32-7.27 (m, 4H), 7.22-7.17 (m, 1H), 6.87 (q, J=5.2 Hz, 1H), 4.35-4.31 (m, 1H), 3.61-3.54 (m, 1H), 3.25-3.16 (m, 1H), 2.90 (d, J=8.0 Hz, 1H), 2.60 (s, 1H), 2.47-2.46 (d, J=3.2 Hz, 1H), 1.78-1.60 (m, 3H), 1.55-1.44 (m, 4H), 1.26-1.24 (m, 2H), 1.20-1.18 (s, 9H), 1.10-1.06 (m, 3H)

[M+Na]$^+$=410.2

Example 26. PRX-P5-008

N-(1-(Z)-Octadec-9-enoyloxy)ethoxycarbonyl)-(−)-N-ethyl-3-phenylbicyclo[2.2.1]heptan-2-amine (Also Known as (Z)-Octadec-9-enoic acid 1-[N-ethyl-(3-phenyl-bicyclo[2.2.1]hept-2-yl)-carbamoyloxy]-ethyl ester)

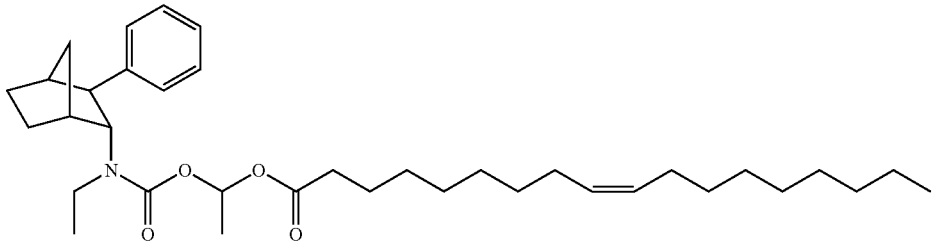 [SMILES: CCCCCCCC/C=C\CCCCCCCC(=O)OC(C)OC(=O)N(CC)C1C2CCC(C2)C1c1ccccc1]

Using the general procedure described in Example 18 above employing PRX-002 (−) isomer, (0.6 g, 2.79 mmol) and oleic acid (1.58 g, 5.60 mmol), provided the product (PRX-P5-008) (0.55 g, 35% yield) as a yellow liquid.

$^1$H-NMR (CDCl$_3$, 400 MHz) δ 7.33-7.27 (m, 4H), 7.22-7.18 (m, 1H), 6.87 (q, J=5.6 Hz, 1H), 5.36-5.33 (m, 2H), 4.35-4.32 (m, 1H), 3.59-3.55 (m, 1H), 3.24-3.18 (m, 1H), 2.89-2.88 (d, J=3.6 Hz, 1H), 2.61 (s, 1H), 2.44-2.43 (m, 1H), 2.32-2.27 (m, 2H), 2.01-1.98 (m, 4H), 1.76-1.68 (m, 2H), 1.61-1.57 (m, 3H), 1.54-1.51 (m, 2H), 1.29-1.24 (m, 24H), 1.09 (s, J=6.8 Hz, 3H), 0.90 (t, J=6.8 Hz, 3H)

[M+Na]$^+$=590.3

Example 27. PRX-P5-009

N-(1-Tetradecanoyloxyethoxycarbonyl)-(−)-N-ethyl-3-phenylbicyclo[2.2.1]heptan-2-amine (Also Known as Tetradecanoic Acid 1-[N-ethyl-(3-phenyl-bicyclo [2.2.1]hept-2-yl)-carbamoyloxy]-ethyl ester)

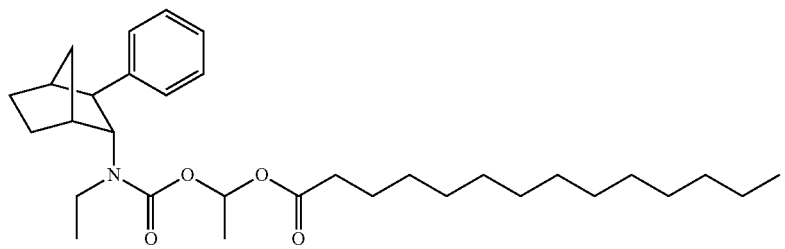 [SMILES: CCCCCCCCCCCCCC(=O)OC(C)OC(=O)N(CC)C1C2CCC(C2)C1c1ccccc1]

Using the general procedure described in Example 18 above employing PRX-002 (−) isomer, (330 mg, 1.55 mmol) and tetradecanoic acid (690 mg, 3.06 mmol), provided the product (PRX-P5-009) (310 mg, 40% yield) as a yellow liquid.

$^1$H-NMR (CDCl$_3$, 400 MHz) δ 7.32-7.27 (m, 4H), 7.22-7.18 (m, 1H), 6.87 (q, J=5.2 Hz, 1H), 4.35-4.32 (m, 1H), 3.59-3.56 (m, 1H), 3.24-3.18 (m, 1H), 2.89 (d, J=6 Hz, 1H), 2.61 (s, 1H), 2.44 (d, J=4 Hz, 1H), 2.32-2.25 (m, 2H), 1.75-1.60 (m, 2H), 1.55-1.47 (m, 4H), 1.34-1.25 (m, 25H), 1.10 (t, J=7.2 Hz, 3H), 0.90 (t, J=6.8 Hz, 3H)

[M+Na]$^+$=536.3

Example 28. PRX-P5-010

N-(1-Hexradecanoyloxyethoxycarbonyl)-(−)-N-ethyl-3-phenylbicyclo[2.2.1]heptan-2-amine (Also Known as Hexadecanoic Acid 1-[N-ethyl-(3-phenyl-bicyclo[2.2.1]hept-2-yl)-carbamoyloxy]-ethyl ester)

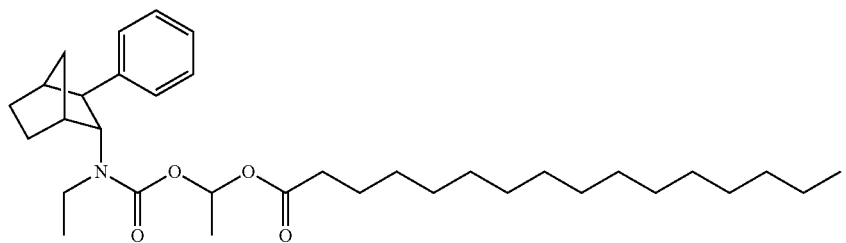 [SMILES: CCCCCCCCCCCCCCCC(=O)OC(C)OC(=O)N(CC)C1C2CCC(C2)C1c1ccccc1]

Using the general procedure described in Example 18 above employing PRX-002 (−) isomer, (0.6 g, 2.79 mmol) and hexadecanoic acid (1.43 g, 5.60 mmol), provided the product (PRX-P5-010) (0.6 g, 40% yield) as a yellow liquid.

$^1$H-NMR (CDCl$_3$, 400 MHz) δ 7.33-7.27 (m, 4H), 7.22-7.18 (m, 1H), 6.87 (q, J=5.2 Hz, 1H), 4.35-4.32 (m, 1H), 3.59-3.56 (m, 1H), 3.28-3.16 (m, 1H), 2.89-2.87 (d, J=6 Hz, 1H), 2.61 (s, 1H), 2.44 (d, J=4.4 Hz, 1H), 2.34-2.28 (m, 2H), 1.75-1.68 (m, 2H), 1.64-1.58 (m, 1H), 1.54-1.47 (m, 4H), 1.34-1.26 (m, 28H), 1.09 (t, J=6.8 Hz, 3H), 0.90 (t, J=6.8 Hz, 3H)

[M+Na]$^+$=564.3

Example 29. PRX-P5-011

N-(1-Octadecanoyloxyethoxycarbonyl)-(+)-N-ethyl-3-phenylbicyclo[2.2.1]heptan-2-amine (Also Known as Octadecanoic Acid 1-[N-ethyl-(3-phenyl-bicyclo[2.2.1]hept-2-yl)-carbamoyloxy]-ethyl ester)

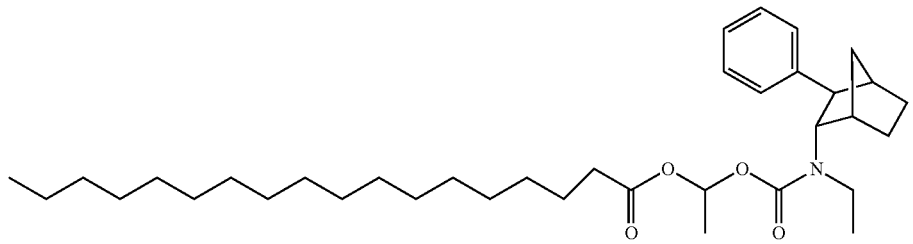 [SMILES: CCCCCCCCCCCCCCCCCC(=O)OC(C)OC(=O)N(CC)C1C2CCC(C2)C1c1ccccc1]

Using the general procedure described in Example 18 above employing PRX-002 (+) isomer, (5 g, 23.22 mmol) and octadecanoic acid (13.27 g, 46.68 mmol), provided the product (PRX-P5-011) (5.82 g, 44% yield) as a pale yellow liquid.

$^1$H-NMR (CDCl$_3$, 400 MHz) δ 7.33-7.28 (m, 4H), 7.22-7.18 (m, 1H), 6.87 (q, J=5.6 Hz, 1H), 4.35 (d, J=5.6 Hz, 1H), 3.59 (t, J=6.8 Hz, 1H), 3.24-3.18 (m, 1H), 2.89 (d, J=6.4 Hz, 1H), 2.61 (s, 1H), 2.44-2.43 (m, 1H), 2.32-2.27 (m, 2H), 1.75-1.68 (m, 2H), 1.64-1.58 (m, 2H), 1.54-1.51 (m, 1H), 1.50-1.47 (m, 3H), 1.32-1.25 (m, 31H), 1.09 (t, J=6.8 Hz, 3H), 0.90 (t, J=6.8 Hz, 3H)

[M+Na]$^+$=592.30

Example 30. General Synthetic Procedure for PRX-P6-001 to PRX-P6-007

Scheme 4.3. The synthesis of dipeptide linked prodrugs

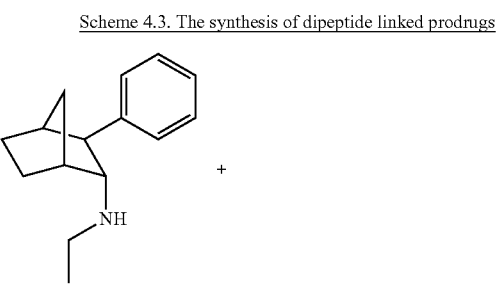

PRX-002 or PRX-001

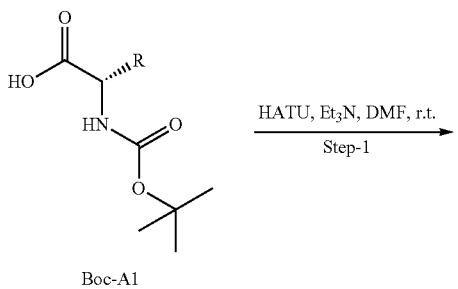

Boc-A1

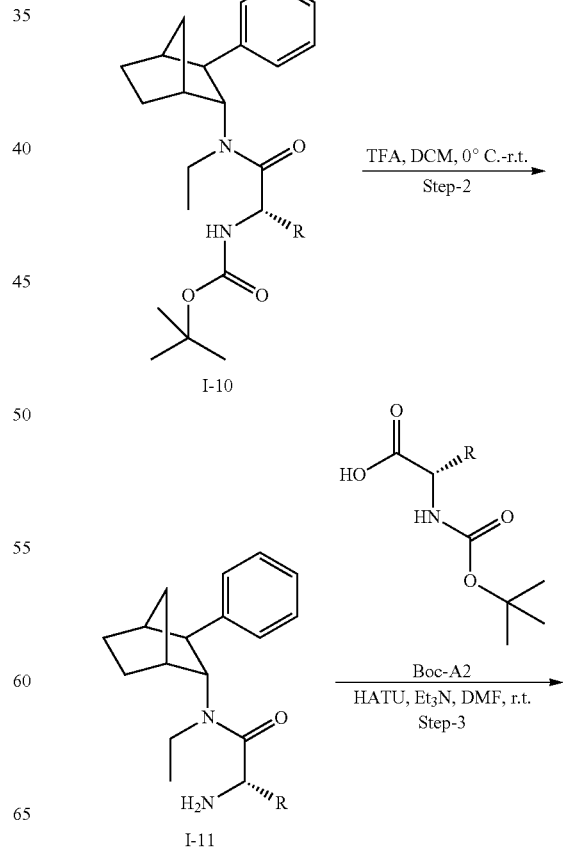

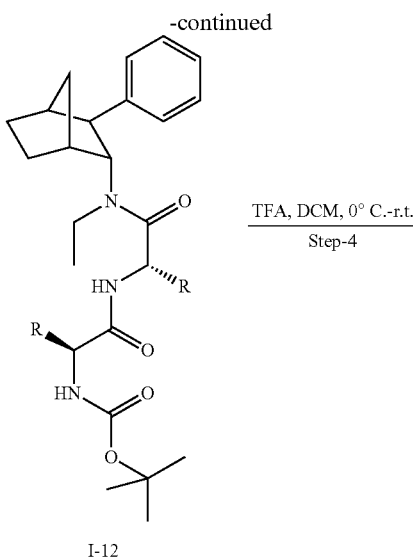

I-12

TFA, DCM, 0° C.-r.t.
Step-4

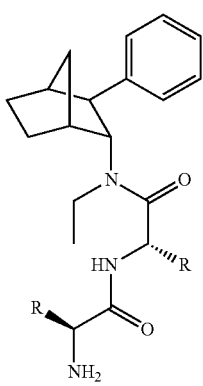

PRX-P6-001 to PRX-P6-011

Step 1: To a solution of Boc-A1 (1.2 eq) in DMF (5 volumes) was added HATU (1.5 eq), Et₃N (2 eq) and the reaction was stirred for 20 min. Then, a solution of PRX-002 (1eq) in DMF (5 volumes) was introduced dropwise and the reaction mixture was stirred at ambient temperature for 12 hours. After the completion of reaction (TLC eluent: 40% EtOAc in petroleum ether), the reaction was quenched with ice cold water (20 volumes) and extracted with ethyl acetate (2×10 volumes). The combined organic layer was washed with 3% citric acid solution (2×10 volumes), saturated NaHCO₃ solution (2×10 volumes) and brine solution (20 volumes). The combined organic layer was dried over anhydrous sodium sulfate, concentrated under reduced pressure. The crude product thus obtained was purified using flash column chromatography to yield the intermediate I-10.

Step 2: To a solution of intermediate I-10 (1 eq) in DCM (5 volumes) was added TFA (15 volumes) dropwise at 0-5° C. and the mixture was stirred for 30 min at ambient temperature. After the completion of reaction (TLC eluent: 80% EtOAc in petroleum ether), the reaction mixture was concentrated under reduced pressure to remove TFA. The residue thus obtained was washed with hexane to give thick and brownish liquid, which was dissolved in ethyl acetate (2×20 volumes) and then washed with saturated aq. NaHCO₃ solution (20 volumes) and brine (20 volumes). The combined EtOAc organic layer was dried over anhydrous sodium sulfate and concentrated under reduced pressure to give intermediate I-11 as a sticky brownish semi solid mass.

Step 3: To a solution of intermediate Boc-A₂ (1.2 eq) in DMF (5 volumes) was added HATU (1.5 eq), Et₃N (2 eq) and the mixture was stirred for 20 min. Then, a solution of I-11 (1 eq) in DMF (5 volumes) was added dropwise and the reaction was kept under stirring for 12 hours at ambient temperature. After the completion of reaction (TLC eluent: 40% EtOAc in petroleum ether), the reaction was quenched with ice cold water (20 volumes), and extracted with ethyl acetate (2×10 volumes). The combined organic layer was washed with 3% aq. citric acid solution (2×10 volumes), saturated NaHCO₃ solution (2×10 volumes) and brine solution (20 volumes), over anhydrous sodium sulfate and concentrated under reduced pressure. The crude product thus obtained was purified using flash column chromatography to yield intermediate I-12.

Step 4: To a solution of intermediate I-12 (1 eq) in DCM (5 volumes) was added TFA (15 volumes) dropwise at 0-5° C. and the mixture was stirred for 30 min at ambient temperature. After the completion of reaction (TLC eluent: 80% EtOAc in petroleum ether), the reaction mixture was concentrated under reduced pressure for the removal of TFA and then the residue was washed with hexane to remove impurities. The thick liquid brownish residue thus obtained was dissolved in ethyl acetate (2×20 volumes), neutralized using saturated aq. NaHCO₃ solution (20 volumes) and washed with brine solution (20 volumes). The combined organic layer was dried over anhydrous sodium sulfate and concentrated under reduced pressure to give dipeptide linked prodrugs, including PRX-P6-001 to PRX-P6-007 as a sticky gummy brownish mass. For the present example, R denotes the atoms for the noted compounds PRX-P6-001 to PRX-P6-007.

Example 31. PRX-P6-001

N-(Glycyl-glycyl)-(−)-N-ethyl-3-phenylbicyclo[2.2.1]heptan-2-amine (Also Known as 2-(2-Aminoacetamido)-N-ethyl-N-(3-phenylbicyclo[2.2.1]heptan-2-yl)acetamide)

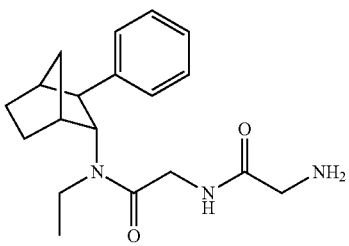 [SMILES: CCN(C(=O)CNC(=O)CN)C1C2CCC(C2)C1c1ccccc1]

Using the general procedure described in Example 30 above employing PRX-002 (−) isomer, (500 mg) and Boc-glycine (820 mg), provided the product (PRX-P6-001) (450 mg, 60% yield) as a off white solid.

¹H-NMR (CDCl₃, 400 MHz) δ 8.03 (s, 1H), 7.30-7.21 (m, 5H), 4.71 (s, 1H), 4.23-3.97 (m, 3H), 3.49-3.19 (m, 2H), 2.90 (s, 1H), 2.58-2.41 (m, 2H), 1.81 (m, 4H), 1.54-1.50 (m, 3H), 1.26 (s, J=5.6 Hz, 3H)

[M+H]⁺=330.50

Example 32. PRX-P6-002

N-(Valyl-D-valyl)-(−)-N-ethyl-3-phenylbicyclo[2.2.1]heptan-2-amine (Also Known as (S)-2-Amino-N—{(R)-1-[ethyl-(3-phenyl-bicyclo[2.2.1]hept-2-yl)-carbamoyl]-2-methyl-propyl}-3-methyl-butyramide)

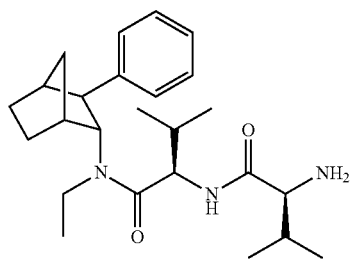 [SMILES: CCN(C(=O)[C@H](NC(=O)[C@@H](N)C(C)C)C(C)C)C1C2CCC(C2)C1c1ccccc1]

Using the general procedure described in Example 30 above employing PRX-002 (−) isomer, (500 mg), Boc-D-Valine (269 mg) and Boc-L-Valine (353 mg), provided the product (PRX-P6-002) (337 mg, 35% yield) as an off white solid.

$^1$H NMR (CDCl$_3$, 400 MHz) δ 7.54-7.48 (m, 2H), 7.32-7.27 (m, 5H), 7.25-7.18 (m, 1H), 4.85-4.77 (m, 3H), 4.31-4.28 (t, J=4.4 Hz, 1H), 4.06-4.01 (q, J=6.8 Hz, 1H), 3.70-3.64 (m, 1H), 3.43-3.37 (m, 1H), 3.13-3.09 (m, 1H), 2.72 (s, 1H), 1.95-1.92 (J=10.8 Hz, 1H), 1.60-1.47 (m, 2H), 1.25-1.22 (dd, J=1.2 Hz & 10.4 Hz, 2H), 1.19-1.12 (m, 2H), 1.01 (s, 3H), 0.82 (d, 6H), 0.72 (d, J=6.8 Hz, 6H)
[M+H]$^+$=414.2

Example 33. PRX-P6-003

N-(Glycyl-Alanyl)-(−)-N-ethyl-3-phenylbicyclo[2.2.1]heptan-2-amine (Also Known as (S)-2-(2-Amino-acetylamino)-N-ethyl-N-(3-phenyl-bicyclo[2.2.1]hept-2-yl)-propionamide)

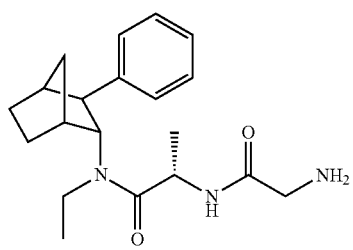 [SMILES: CCN(C(=O)[C@H](C)NC(=O)CN)C1C2CCC(C2)C1c1ccccc1]

Using the general procedure described in Example 30 above employing PRX-002 (−) isomer, (500 mg), Boc-L-alanine (269 mg) and Boc-glycine (292 mg), provided the product (PRX-P6-003) (344 mg, 44% yield) as a pale yellow liquid.

$^1$H-NMR (CDCl$_3$, 400 MHz) δ7.92 (t, 2H), 7.70 (d, J=5.8 Hz, 1H), 7.34-7.27 (m, 3H), 7.24-7.18 (m, 2H), 4.97-4.89 (m, 1H), 4.48 (s, 1H), 4.30 (s, 1H), 4.12-4.11 (m, 1H), 4.04-3.99 (m, 1H), 3.80-3.65 (m, 1H), 3.59-3.57 (m, 1H), 3.43-3.39 (m, 1H), 3.36-3.35 (m, 2H), 3.30-3.21 (m, 1H), 3.03-3.01 (d, J=6 Hz, 1H), 2.73 (s, 1H), 2.57-2.42 (m, 2H), 1.30 (d, J=5.8 Hz, 3H), 1.03 (s, J=5.6 Hz, 3H)
[M+H]$^+$ 344.47, found 344.1

Example 34. PRX-P6-004

N-(Valyl-valyl)-(−)-N-ethyl-3-phenylbicyclo[2.2.1]heptan-2-amine (Also Known as (S)-2-Amino-N—{(S)-1-[N-ethyl-(3-phenyl-bicyclo[2.2.1]hept-2-yl)-carbamoyl]-2-methyl-propyl}-3-methyl-butyramide)

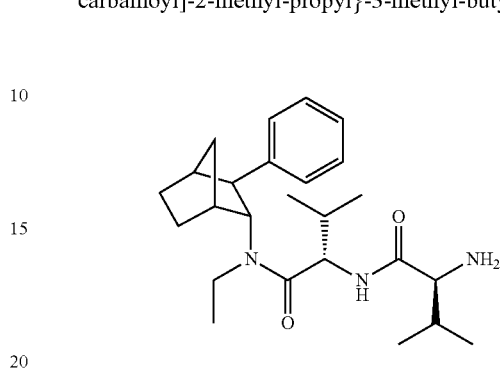

Using the general procedure described in Example 30 above employing, PRX-002 (−) isomer, (500 mg) and Boc-L-Valine (987 mg), provided the product (PRX-P6-004) (386 mg, 40% yield) as a off white solid.

$^1$H NMR (CDCl$_3$, 400 MHz) δ 7.90-7.83 (m, 1H), 7.34-7.27 (m, 4H), 7.22-7.19 (m, 1H), 4.85-4.77 (m, 3H), 4.31-4.28 (t, J=4.4 Hz, 1H), 4.06 (q, J=6.8 Hz, 1H), 3.70-3.64 (m, 1H), 3.43-3.37 (m, 1H), 3.13-3.09 (m, 1H), 2.72 (s, 1H), 1.95 (d, J=10.8 Hz, 1H), 1.60-1.47 (m, 2H), 1.25 (dd, J=1.2 Hz & 10.4 Hz, 2H), 1.19-1.12 (m, 2H), 1.01 (s, 3H), 0.82 (d, 6H), 0.72 (d, J=6.8 Hz, 6H)

[M+H]$^+$=414.2

Example 35. PRX-P6-005

N-(Phenylalanyl-phenylalanyl)-(−)-N-ethyl-3-phenylbicyclo[2.2.1]heptan-2-amine (also known as (S)-2-Amino-N—{(S)-1-[N-ethyl-(3-phenyl-bicyclo[2.2.1]hept-2-yl)-carbamoyl]-2-phenyl-ethyl}-3-phenyl-propionamide)

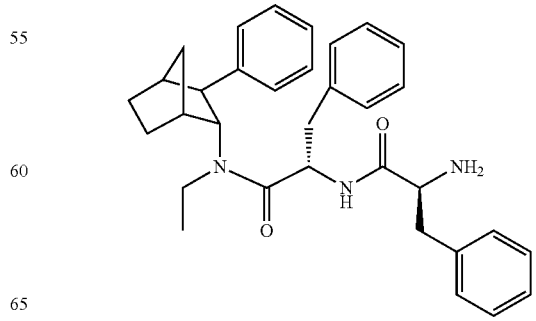

Using the general procedure described in Example 30 above employing PRX-002 (−) isomer, (0.7 g) and Boc-L-Phenyl alanine (1.643 g), provided the product (PRX-P6-005) (0.594 g, 36% yield) as a yellow liquid.

$^1$H-NMR (CDCl$_3$, 400 MHz) δ7.90-7.83 (m, 3H), 7.33-7.27 (m, 4H), 7.24-7.10 (m, 11H), 5.17-5.00 (m, 1H), 4.76-4.37 (m, 1H), 3.74-3.68 (m, 1H), 3.61-3.55 (m, 1H), 3.20-3.10 (m, 2H), 3.08-2.98 (m, 2H), 2.90-2.78 (m, 2H), 2.74-2.50 (m, 2H), 2.45-2.30 (m, 1H), 1.56-1.42 (m, 2H), 1.32-1.18-1.16 (m, 2H), 1.15 (s, J=5.7 Hz, 3H), 0.85-0.77 (m, 1H)

[M+H]$^+$=510.3

Example 36. PRX-P6-006

N-(Alanyl-glycyl)-(−)-N-ethyl-3-phenylbicyclo[2.2.1]heptan-2-amine (Also Known as (S)-2-Amino-N—{[N-ethyl-(3-phenyl-bicyclo [2.2.1]hept-2-yl)-carbamoyl]-methyl}-propionamide)

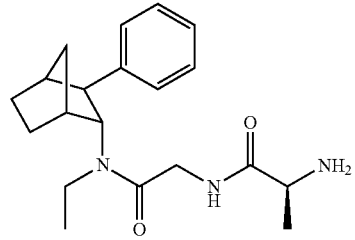 [SMILES: CCN(C(=O)CNC(=O)[C@H](C)N)C1C2CCC(C2)C1c1ccccc1]

Using the general procedure described in Example 30 above employing PRX-002 (−) isomer, (500 mg), Boc-L-Alanine (283 mg) and Boc-glycine (488 mg), provided the product (PRX-P6-006) (305 mg, 38% yield) as a yellow liquid.

$^1$H NMR (CDCl$_3$, 400 MHz) δ 8.07-8.05 (m, 1H), 7.33-7.29 (m, 3H), 7.27-7.21 (m, 3H), 4.71 (s, 1H), 4.20-3.91 (m, 4H), 3.66 (s, 1H), 3.35 (s, 1H), 3.20 (d, J=7.2 Hz, 1H), 2.91 (s, 1H), 2.81-2.75 (m, 1H), 2.57-2.42 (m, 1H), 2.22-2.01 (m, 2H), 1.82-1.64 (m, 2H), 1.39-1.30 (m, 1H), 1.28-1.10 (m, 6H)

[M+H]$^+$=344.2

Example 37. PRX-P6-011

N-(Valyl-valyl)-(+)-N-ethyl-3-phenylbicyclo[2.2.1]heptan-2-amine (Also Known as (S)-2-Amino-N—{(S)-1-[N-ethyl-(3-phenyl-bicyclo[2.2.1]hept-2-yl)-carbamoyl]-2-methyl-propyl}-3-methyl-butyramide)

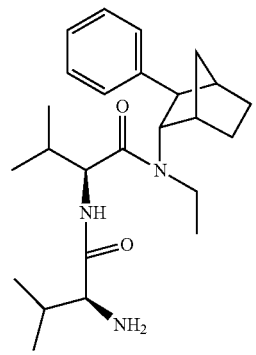 [SMILES: CCN(C(=O)[C@@H](NC(=O)[C@@H](N)C(C)C)C(C)C)C1C2CCC(C2)C1c1ccccc1]

Using the general procedure described in Example 30 above employing PRX-002 (+) isomer, (4 g) and Boc-L-Valine (7.9 g), provided the product, (PRX-P6-011) (3 g, 39% yield) as a colorless semisolid.

$^1$H-NMR (CDCl$_3$, 400 MHz) δ 7.90-7.83 (m, 1H), 7.34-7.27 (m, 4H), 7.22-7.19 (m, 1H), 4.85-4.77 (m, 3H), 4.31-4.28 (t, J=4.4 Hz, 1H), 4.06 (q, J=6.8 Hz, 1H), 3.70-3.64 (m, 1H), 3.43-3.37 (m, 1H), 3.13-3.09 (m, 1H), 2.72 (s, 1H), 1.95 (d, J=10.8 Hz, 1H), 1.60-1.47 (m, 2H), 1.25 (dd, J=1.2 Hz & 10.4 Hz, 2H), 1.19-1.12 (m, 2H), 1.01 (s, 3H), 0.82 (d, 6H), 0.72 (d, J=6.8 Hz, 6H)

[M+H]$^+$=414.2

Example 38. PRX-P6-007

N—(N6-Lysyl-lysyl)-(−)-N-ethyl-3-phenylbicyclo[2.2.1]heptan-2-amine (Also Known as (S)-2,6-Diamino-hexanoic acid {(S)-5-amino-5-[ethyl-(3-phenyl-bicyclo[2.2.1]hept-2-yl)-carbamoyl]-pentyl}-amide)

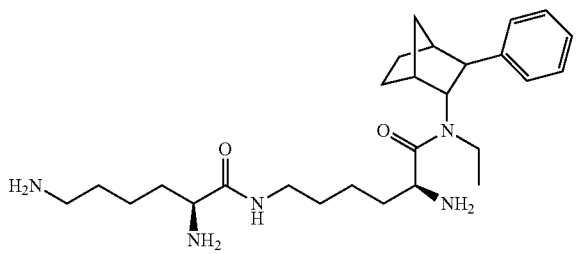 [SMILES: CCN(C(=O)[C@@H](N)CCCCNC(=O)[C@@H](N)CCCCN)C1C2CCC(C2)C1c1ccccc1]

SCHEME 5. THE SYNTHESIS OF PRX-P6-007
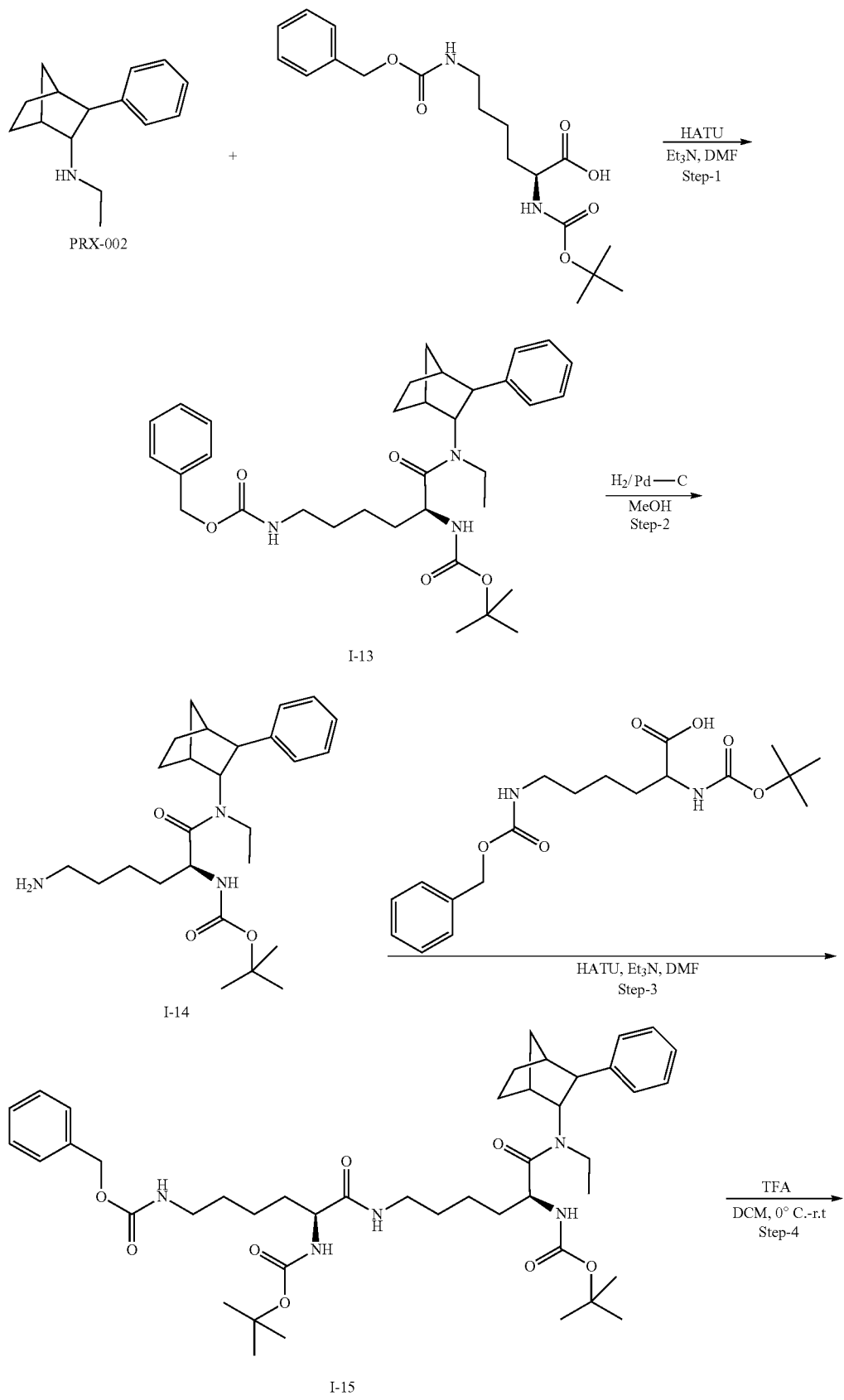

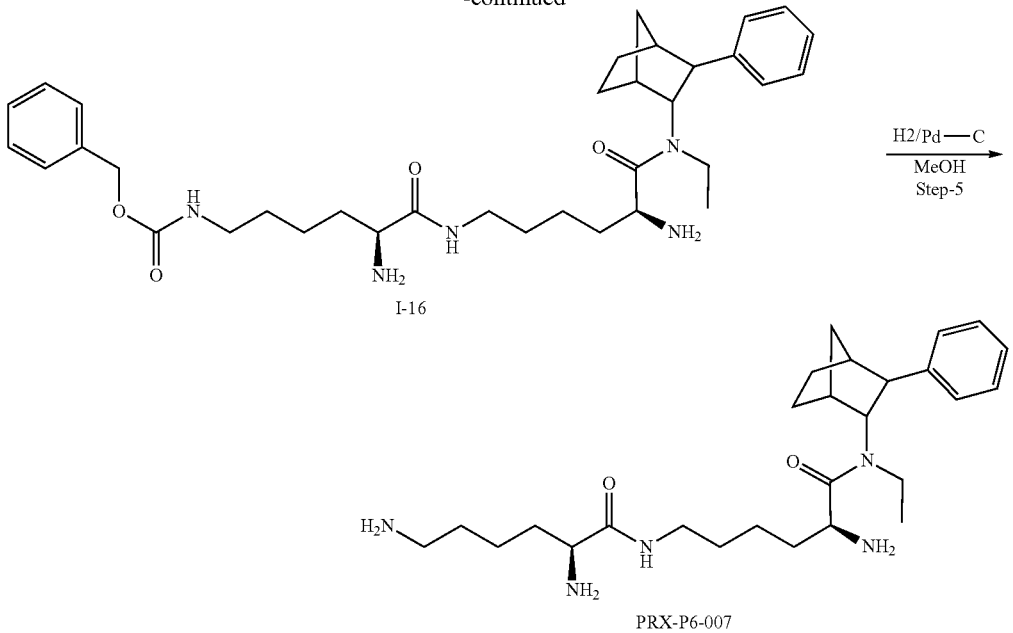

I-16

PRX-P6-007

Step 1: To a solution of Boc-Lys(Z)—OH (1.27 g) in DMF (7 mL) was added HATU (1.6 g), Et$_3$N (0.65 mL). After 20 minute stirring, PRX-002 (−) isomer (0.6 g) in DMF (3 mL) was added dropwise and the reaction mixture was stirred for 12 hours at ambient temperature. After the completion of reaction (TLC eluent: 40% EtOAc in petroleum ether), the reaction was quenched with ice cold water (150 mL) and extracted with ethyl acetate (2×70 mL). The combined organic layer was washed with 3% citric acid solution (2×50 mL), saturated NaHCO$_3$ solution (2×50 mL) and brine (50 mL), dried over anhydrous sodium sulfate and concentrated under reduced pressure. The crude product thus obtained was purified using flash column chromatography to afford intermediate 1-13.

Step 2: To a solution of 1-13 (1.3 g) in methanol (50 mL) was added 10% Pd/C (1.3 g, 100% w/w) and the mixture was kept under H$_2$ (60 psi) for 8 h in Parr-shaker. After the completion of reaction (TLC eluent: 10% MeOH in DCM), the reaction mixture was filtered through Celite bed and the filtrate was concentrated under reduced pressure to yield intermediate I-14 as a thick pale yellow liquid.

Step 3: To a solution of Boc-Lys(Z)—OH (0.87 g) in DMF (7 mL) was added HATU (1.09 g), Et$_3$N (0.6 mL). After stirring for 20 minutes, a solution of I-14 (0.85 g) in DMF (3 mL) was added dropwise and the reaction mixture was stirred for 12 hours at ambient temperature. After the completion of reaction (TLC eluent: 40% EtOAc in petroleum ether), the reaction was quenched with ice cold water (150 mL) and extracted with ethyl acetate (2×70 mL). The combined organic layer was washed with 3% citric acid solution (2×50 mL), saturated NaHCO$_3$ solution (2×50 mL) and brine solution (50 mL). The combined organic layer was dried over anhydrous sodium sulfate and concentrated under reduced pressure. The crude product thus obtained was purified using flash column chromatography to give intermediate I-15.

Step 4: To a solution of 1-15 (1.5 g) in DCM (15 mL) was added TFA (20 mL) dropwise at 0-5° C. and the reaction mixture was stirred for 30 min at ambient temperature. After the completion of reaction (TLC eluent: 10% MeOH in DCM), the reaction mixture was concentrated under reduced pressure for the removal of TFA. The residue thus obtained was washed with hexane for removal of impurities and yielding thick liquid brownish mass, which was further dissolved in ethyl acetate (50 mL), neutralized using saturated aq. NaHCO$_3$ (30 mL) solution and washed with brine solution (30 mL). The ethyl acetate layer was dried over anhydrous sodium sulfate and concentrated under reduced pressure to afford intermediate I-16 as a sticky gummy brownish mass.

Step 5: To a solution of I-16 (0.78 g) in methanol (50 mL) was added 10% Pd/C (0.78 g, 100% w/w) and the mixture was kept under H$_2$ pressure of 60 psi. for 8 hours in Parr-shaker. After the completion of reaction (TLC eluent: 10% MeOH in DCM), the mixture was filtered through Celite and the filtrate was concentrated under reduced pressure. The crude product obtained was purified by using preparative HPLC to yield the product (PRX-P6-007) (0.4 g, 30% yield) as a thick pale yellow liquid.

$^1$H-NMR (DMSO-d$_6$, 400 MHz) δ 8.49 (s, 1H) 7.78-7.65 (m, 1H), 7.35-7.17 (m, 5H), 4.38-4.32 (m, 1H), 3.45-3.25 (m, 3H), 3.20-3.12 (m, 6H), 2.52-2.45 (m, 3H), 2.35-2.31 (m, 4H), 1.87-1.20 (m, 18H), 1.01 (s, 3H)

[M+H]$^+$=472.30

Example 39

Pharmacokinetic (PK) Profiles of Conjugates of N-ethyl-3-phenylbicyclo[2.2.1]heptan-2-amine We describe here PK results of prodrugs of PRX-002 (−) or (+) isomers. All doses of prodrugs were administered such that they were equivalent to 5 mg/kg of PRX-002 (−) or (+) for oral studies and 2 mg/kg PRX-002 (−) or (+) for intravenous studies in male Sprague-Dawley (MSD) rats. Higher doses of up to 10 or 15 mg/kg [again equivalent to PRX-002 (−)] were used in some studies (as specified)]. Formulation preparation, dose administration and time of sample collection was as follows.

Oral Formulation Preparation: Test item was weighed [5 mg equivalent dose of PRX-002 for prodrugs] and transferred to a graduated tube. Then 10 μL of Tween 80 was added and vortexed mixed until the test item was completely mixed. Small volume of 0.5% (w/v) carboxymethylcellulose in water solution was then added dropwise with continuous vortex mixing until a uniform suspension was obtained. The final volume was then made up to 10 mL with 0.5% (w/v) carboxymethylcellulose in water with final strength of 0.5 mg/mL. The obtained formulation was found to be uniform suspension. This formulation was freshly prepared before the administration to animals.

Oral Dose Administration: Adult male Sprague Dawley Rats aged 8-10 weeks were used for the study. Fasted animals were administered test item by oral route with a dose of 5 mg/kg body weight at dose volume of 10 mL/kg body weight. Under mild isoflurane anesthesia, blood specimens were collected by retro-orbital puncture method using capillary tubes into pre-labeled tubes containing anticoagulant ($K_2$EDTA-2 mg/mL blood) during the next 24 hours of post dose as mentioned in below table. For blood sampling at multiple time points, right and left eyes were used alternatively for blood collection. Collected blood specimens were centrifuged at 4000 rpm, 4° C. for 10 minutes and plasma were separated and stored at −80° C. until analysis.

Blood was collected as outlined in Table 39.1 (oral).

TABLE 39.1

| Group no. | Animal ID | Blood collection time points (h) | | | | | | | |
| --- | --- | --- | --- | --- | --- | --- | --- | --- | --- |
| | | 0.08 | 0.25 | 0.50 | 1.00 | 2.00 | 4.00 | 6.00 | 24.00 |
| G-X | R00X | X | X | X | X | X | X | X | X |
| | R00X | X | X | X | X | X | X | X | X |
| | R00X | X | X | X | X | X | X | X | X |

IV Formulation Preparation: Test item was weighed [(to be equivalent to 2 mg/kg of PRX 002 dose] and transferred to a graduated tube. Then 500 μL of PEG 400 (v/v) was added and vortex mixed thoroughly until the test item was completely dissolved. Then 1500 μL of Hydroxypropyl-β-cyclodextrin (HPβCD, 50% w/v) was added and vortex mixed thoroughly. The final volume was then made up to 5000 μL with sterile water for injection (SWFI, v/v) with final formulation strength of 0.4 mg/mL. The obtained formulation was found to be clear solution. This formulation was freshly prepared before the administration to animals.

IV Dose Administration: Adult male Sprague Dawley Rats aged 8-10 weeks were used for the study. Animals were administered the test item by Intravenous bolus route with a dose of 2 mg/kg body weight at dose volume of 5.0 mL/kg body weight. Under mild isoflurane anesthesia, blood specimens were collected by retro-orbital puncture method using capillary tubes into pre-labeled tubes containing anticoagulant ($K_2$EDTA-2 mg/mL blood) during the next 24 hours of post dose as mentioned in below table. For blood sampling at multiple time points, right and left eyes were used alternatively for blood collection. Collected blood specimens were centrifuged at 4000 rpm, 4° C. for 10 minutes and plasma were separated and stored at −80° C. until analysis.

Blood was collected as outlined in Table 39.2 (IV).

TABLE 39.2

| Group no. | Animal ID | Blood collection time points (h) | | | | | | | |
| --- | --- | --- | --- | --- | --- | --- | --- | --- | --- |
| | | 0.08 | 0.25 | 0.50 | 1.00 | 2.00 | 4.00 | 6.00 | 24.00 |
| G-x | R00x | X | X | X | X | X | X | X | X |
| | R00X | X | X | X | X | X | X | X | X |
| | R00X | X | X | X | X | X | X | X | X |

Higher Dose Oral Formulation and Dose Administration for PRX-P4-003 [10 mg/kg Dose Equivalent of PRX-002 (−)]

Formulation Preparation: Test item PRX-P4-003 was weighed and transferred to a graduated tube. Then 12.42 µL of Tween 80 was added and vortexed mixed until the test item was completely mixed. Small volume of 0.5% (w/v) Carboxymethylcellulose in water solution was then added dropwise with continuous vortex mixing until a uniform suspension was obtained. The final volume was then made up to 12.42 mL with 0.5% (w/v) Carboxymethylcellulose in water with final strength of 1.0 mgA/mL. The obtained formulation was found to be uniform suspension. This formulation was freshly prepared before the administration to animals.

Dose Administration: Adult male Sprague Dawley Rats aged 8-10 weeks were used for the study. Fasted animals were administered with a PRX-P4-003 by oral route with a dose of 10 mg/kg body weight at dose volume of 10 mL/kg body weight. Under mild isoflurane anesthesia, blood specimens were collected by retro-orbital puncture method using capillary tubes into pre-labeled tubes containing anticoagulant ($K_2$EDTA-2 mg/mL blood) during the next 24 hours of post dose as mentioned in below table. For blood sampling at multiple time points, right and left eyes were used alternatively for blood collection. Collected blood specimens were centrifuged at 4000 rpm, 4° C. for 10 minutes and plasma were separated and stored at −80° C. until analysis.

Higher Dose IV Formulations and Administration for PRX-P4-003 [10 mg/kg Dose Equivalent of PRX-002 (−)]

Formulation Preparation [PRX-P4-003 dose equivalent of 10 mg/kg PRX-002 (−)]: Test item PRX-P4-003 was weighed and transferred to a graduated tube. Then 600 µL of PEG 400 (v/v) was added and vortex mixed thoroughly until the test item was completely dissolved. Then 1.800 mL of Hydroxypropyl-β-cyclodextrin (HPβCD, 50% w/v) was added and vortex mixed thoroughly. The final volume was then made up to 3.600 mL with sterile water for injection (SWFI, v/v) with final formulation strength of 5.16 mgA/mL. The obtained formulation was found to be colloidal solution. This formulation was freshly prepared before the administration to animals.

Dose Administration: Adult male Sprague Dawley Rats aged 8-10 weeks were used for the study. Animals were administered with a PRX-P4-003 by Intravenous bolus route with a dose of 10 mg/kg body weight at dose volume of 5 mL/kg body weight. Under mild isoflurane anesthesia, blood specimens were collected by retro-orbital puncture method using capillary tubes into pre-labeled tubes containing anticoagulant ($K_2$EDTA-2 mg/mL blood) during the next 24 hours of post dose as mentioned in below table. For blood sampling at multiple time points, right and left eyes were used alternatively for blood collection. Collected blood specimens were centrifuged at 4000 rpm, 4° C. for 10 minutes and plasma were separated and stored at −80° C. until analysis.

Higher Dose Oral Formulation and Dose Administration for PRX-P5-006 [15 mg/kg Dose Equivalent of PRX-002 (−)]

Formulation Preparation: Test item PRX-P5-006 was weighed and transferred to a graduated tube. Then 10 µL of Tween 80 was added and vortexed mixed until the test item was completely mixed. Small volume of 0.5% (w/v) Carboxymethylcellulose in water solution was then added dropwise with continuous vortex mixing until a uniform suspension was obtained. The final volume was then made up to 10 mL with 0.5% (w/v) Carboxymethylcellulose in water with final strength of 3.97 mg/mL. The obtained formulation was found to be uniform suspension. This formulation was freshly prepared before the administration to animals.

Dose Administration: Adult male Sprague Dawley Rats aged 8-10 weeks were used for the study. Fasted animals were administered with a PRX-P5-006 by oral route with a dose of 15 mg/kg body weight at dose volume of 10 mL/kg body weight. Under mild isoflurane anesthesia, blood specimens were collected by retro-orbital puncture method using capillary tubes into pre-labeled tubes containing anticoagulant ($K_2$EDTA-2 mg/mL blood) during the next 24 hours of post dose as mentioned in below table. For blood sampling at multiple time points, right and left eyes were used alternatively for blood collection. Collected blood specimens were centrifuged at 4000 rpm, 4° C. for 10 minutes and plasma were separated and stored at −80° C. until analysis.

Higher Dose IV Formulation and Dose Administration for PRX-P5-006 [15 mg/kg Dose Equivalent of PRX-002 (−)]

Formulation Preparation: Test item PRX-P5-006 was weighed and transferred to a graduated tube. Then 500 µL of DMSO (v/v) was added vortex mixed thoroughly until the test item was completely dissolved. Then 4000 µL of Hydroxypropyl-β-cyclodextrin (HPβCD, 50% w/v) was added and vortex mixed thoroughly. Then 2500 µL of PEG 400 (v/v) was added and vortex mixed thoroughly. The final volume was then made up to 10000 µL with sterile water for injection (SWFI, v/v) with final formulation strength of 3.97 mg/mL. The obtained formulation was found to be clear solution. This formulation was freshly prepared before the administration to animals.

Dose Administration: Adult male Sprague Dawley Rats aged 8-10 weeks were used for the study. Animals were administered with a PRX-P5-006 by Intravenous bolus route with a dose of 15 mg/kg body weight at dose volume of 10 mL/kg body weight. Under mild isoflurane anesthesia, blood specimens were collected by retro-orbital puncture method using capillary tubes into pre-labeled tubes containing anticoagulant ($K_2$EDTA-2 mg/mL blood) during the next 24 hours of post dose as mentioned in below table. For blood sampling at multiple time points, right and left eyes were used alternatively for blood collection. Collected blood specimens were centrifuged at 4000 rpm, 4° C. for 10 minutes and plasma were separated and stored at −80° C. until analysis.

Table 39.3 depicts a set of comparative data of single dose oral and intravenous PK Study of PRX-P4-003. Additional data in this regard is presented in FIG. 1.

TABLE 39.3

Single Dose Oral and Intravenous PK Study of PRX-P4-003 in Male Sprague Dawley Rats

| PK Parameters | Oral | Intravenous |
|---|---|---|
| | Mean Plasma PK Parameters of PRX-P4-003 | |
| Dose (mg/kg) | 5.00 | 2.00 |
| $C_{max}$ (ng/mL) | 0.0 ± 0.0 | 171.963 ± 62.6030 |
| $T_{max}$ (hr) | 0.0 ± 0.0 | 0.080 ± 0.0000 |
| $AUC_{last}$ (hr*ng/mL) | 0.0 ± 0.0 | 132.573 ± 32.5110 |
| $AUC_{inf}$ (hr*ng/mL) | 0.0 ± 0.0 | 215.708 ± 83.3890 |
| $AUC_{\% extrap}$ (%) | 0.0 ± 0.0 | 32.475 ± 83.3890 |
| Vss (L/kg) | 0.0 ± 0.0 | 41.984 ± 19.8767 |
| CL (mL/min/kg) | 0.0 ± 0.0 | 171.947 ± 69.3217 |
| $T_{1/2}$ (hr) | 0.0 ± 0.0 | 3.348 ± 2.1780 |
| $MRT_{last}$ (hr) | 0.0 ± 0.0 | 1.836 ± 0.7130 |

Figure 2:
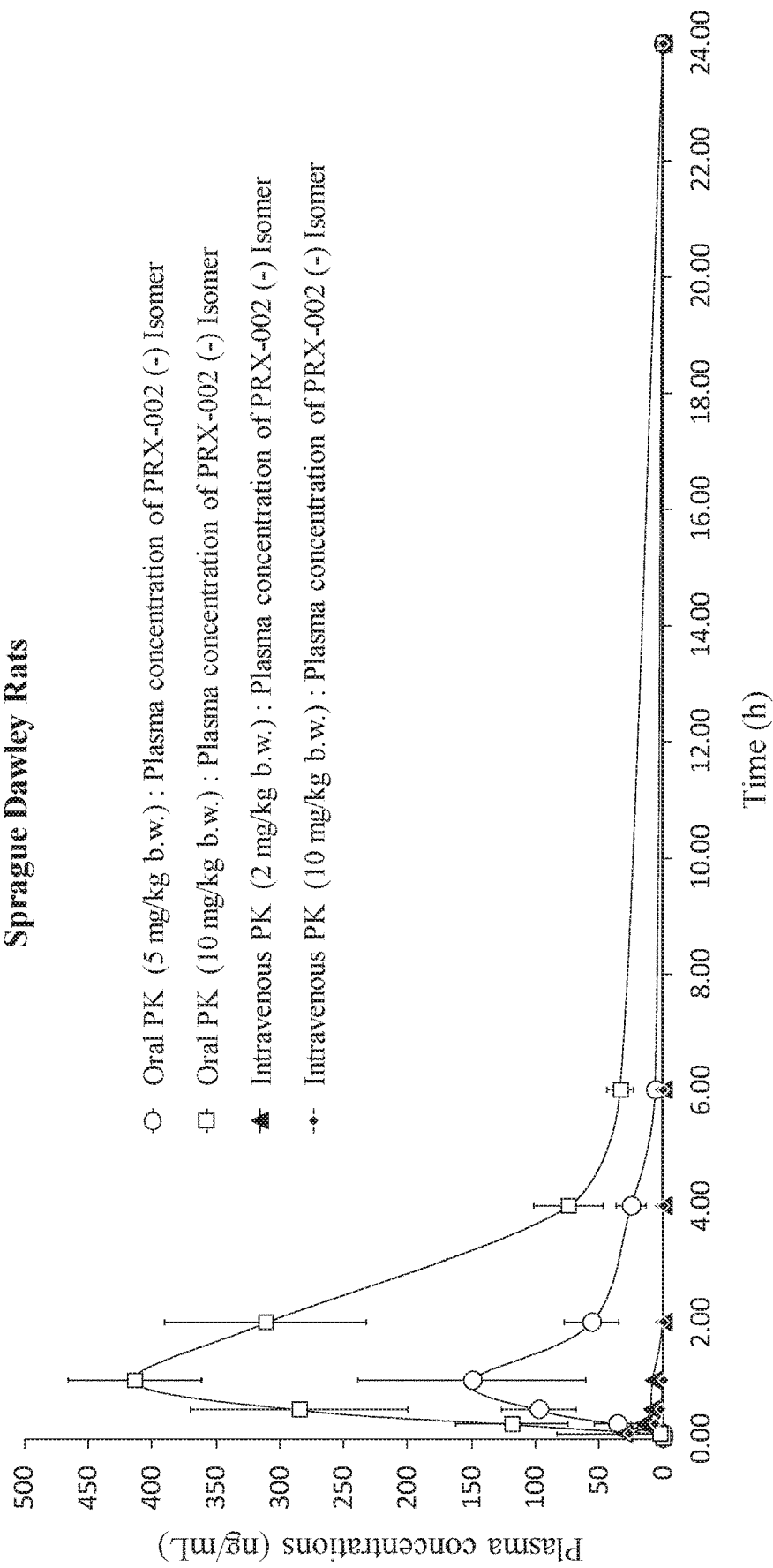
FIG. 2 is a graph depicting oral and IV pharmacokinetics for PRX-P4-003 in male Sprague Dawley rats.

FIG. 2 is a graph depicting oral and IV pharmacokinetics for PRX-P4-003 in male Sprague Dawley rats. The graph depicts the results for the resulting plasma concentration of PRX-002(−) isomer via oral or IV administration. As can be seen, while oral administration results in a desired plasma concentration for the active/parent drug (here, PRX-002(−) isomer), IV administration results in minimal amounts of any of the PRX-P4-003 being converted from the pro-drug form to the active form. The results are outlined above in Table 39.4 and 39.5.

TABLE 39.4

COMPARATIVE DATA: SINGLE DOSE ORAL AND INTRAVENOUS
PK STUDY OF PRX-P4-003 IN MALE SPRAGUE DAWLEY RATS.

| | Mean Plasma PK Parameters of PRX-002 (−) Isomer | | | |
|---|---|---|---|---|
| | A | B | C | D |
| Dose (mg/kg) | 5.00 (oral) | 10.00 (oral) | 2.00 (IV) | 10.00 (IV) |
| $C_{max}$ (ng/mL) | 156.7030 ± 85.32600 | 425.0400 ± 40.46000 | 30.807 ± 10.0830 | NC |
| $T_{max}$ (hr) | 0.8330 ± 0.28900 | 1.3330 ± 0.57700 | 0.080 ± 0.0000 | NC |
| $AUC_{last}$ (hr*ng/mL) | 296.8610 ± 51.2400 | 1092.8470 ± 169.08500 | 14.254 ± 3.8510 | NC |
| $AUC_{inf}$ (hr*ng/mL) | 308.8410 ± 58.24000 | 1158.6130 ± 137.93700 | 22.098 ± 7.0600 | NC |
| $AUC_{\% \; extrap}$ (%) | 3.6430 ± 2.29800 | 5.9310 ± 3.20800 | 34.822 ± 6.9490 | NC |
| Vss (L/kg) | — | | 86.814 ± 23.2576 | NC |
| CL (mL/min/kg) | — | | 1606.391 ± 464.8270 | NC |
| $T_{1/2}$ (hr) | 1.8080 ± 0.30700 | 1.9220 ± 0.09300 | 0.682 ± 0.2440 | NC |
| $MRT_{last}$ (hr) | 1.2770 ± 0.25600 | 1.2890 ± 0.29000 | 0.340 ± 0.0190 | NC |

A: Oral PK (5 mg/kg)
B: Oral PK (10 mg/kg)
C: Intravenous PK (2 mg/kg)
D: Intravenous PK (10 mg/kg)
*NC: Not Calculated. PRX-002 (−) Isomer IV 10 mg/kg PK data analysis was not carried out because limited exposure in plasma concentration profile

TABLE 39.5

Concentration time profile of PRX-002 (−)
after oral and IV dose of PRX-P4-003
Single Dose Oral and Intravenous Pharmacokinetics
Study of PRX-P4-003 in Male Sprague Dawley Rats

| Oral PK | | | Intravenous PK | | | |
|---|---|---|---|---|---|---|
| Plasma concentration of PRX-002 (−) Isomer (ng/mL) | | | | | | |
| Time (h) | Mean | SD | Time (h) | Mean | ± | SD |
| 0.00 | 0.00 | ± 0.00 | 0.00 | — | ± | — |
| 0.08 | 0.00 | ± 0.00 | 0.08 | 30.81 | ± | 10.08 |
| 0.25 | 35.89 | ± 18.38 | 0.25 | 15.63 | ± | 3.90 |
| 0.50 | 97.56 | ± 29.02 | 0.50 | 9.14 | ± | 3.39 |
| 1.00 | 149.74 | ± 89.23 | 1.00 | 7.82 | ± | 0.92 |
| 2.00 | 56.12 | ± 21.49 | 2.00 | 0.00 | ± | 0.00 |
| 4.00 | 25.08 | ± 11.71 | 4.00 | 0.00 | ± | 0.00 |
| 6.00 | 6.10 | ± 3.79 | 6.00 | 0.00 | ± | 0.00 |
| 24.00 | 0.00 | ± 0.00 | 24.00 | 0.00 | ± | 0.00 |

Figure 3:
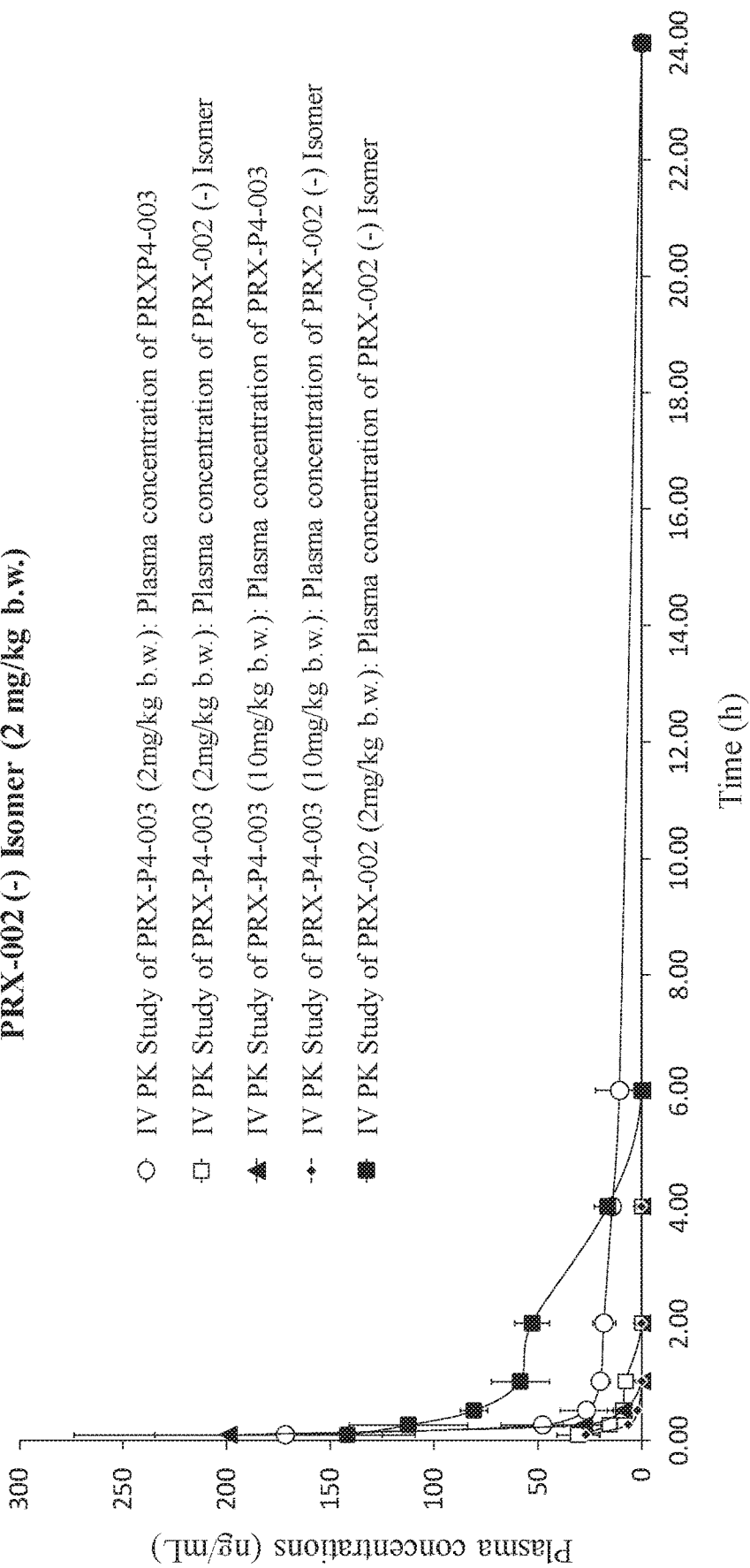
FIG. 3 depicts the results of the comparative data regarding IV PK studies of PRX-P4-003 (2 and 10 mg/kg b.w.) PRX-002(−) isomer (2 mg/kg b.w.).

FIG. 3 depicts the results of the comparative data regarding IV PK studies of PRX-P4-003 (2 and 10 mg/kg b.w.) PRX-002(−) isomer (2 mg/kg b.w) As can be observed very limited amount of parent PRX-002 (−) is generated when the prodrug PRX-P4-003 is administered IV even at higher dose of 10 mg/kg. Additional data is summarized in Tables 39.6-39.7.

TABLE 39.6

Comparative Data: Intravenous PK Study of PRX-P4-003 (2 and 10 mg/kg b.w.)
and PRX-002 (−) Isomer (2 mg/kg b.w.) in Male Sprague Dawley Rats

| | IV PK Study of PRX-P4-003 (2 mg/kg b.w.) | | | | IV PK Study of PRX-P4-003 (10 mg/kg b.w.) | | | | | | IV PK Study of PRX-002 (−) Isomer (2 mg/kg b.w.) | | |
|---|---|---|---|---|---|---|---|---|---|---|---|---|---|
| | Plasma concentration of PRX-P4-003 | | Plasma concentration of PRX-002 (−) Isomer | | Plasma concentration of PRX-P4-003 | | | Plasma concentration of PRX-002 (−) Isomer | | | Plasma concentration of PRX-002 (−) Isomer | | |
| Time (h) | Mean | SD | Mean | SD | Mean | ± | SD | Mean | ± | SD | Mean | ± | SD |
| 0.08 | 171.96 ± 62.60 | | 30.81 ± 10.08 | | 199.64 | ± | 74.37 | 27.06 | ± | 6.80 | 142.01 | ± | 1.21 |
| 0.25 | 47.94 ± 20.26 | | 15.63 ± 3.90 | | 27.98 | ± | 10.03 | 6.59 | ± | 0.69 | 112.59 | ± | 28.48 |
| 0.50 | 26.73 ± 12.51 | | 9.14 ± 3.39 | | 8.96 | ± | 7.80 | 2.02 | ± | 1.79 | 81.21 | ± | 6.58 |
| 1.00 | 20.03 ± 4.68 | | 7.82 ± 0.92 | | 0.00 | ± | 0.00 | 0.00 | ± | 0.00 | 58.82 | ± | 14.08 |
| 2.00 | 18.29 ± 5.46 | | 0.00 ± 0.00 | | 0.00 | ± | 0.00 | 0.00 | ± | 0.00 | 53.05 | ± | 8.64 |
| 4.00 | 14.23 ± 3.98 | | 0.00 ± 0.00 | | 0.00 | ± | 0.00 | 0.00 | ± | 0.00 | 16.55 | ± | 6.41 |
| 6.00 | 10.72 ± 11.52 | | 0.00 ± 0.00 | | 0.00 | ± | 0.00 | 0.00 | ± | 0.00 | 0.00 | ± | 0.00 |
| 24.00 | 0.00 ± 0.00 | | 0.00 ± 0.00 | | 0.00 | ± | 0.00 | 0.00 | ± | 0.00 | 0.00 | ± | 0.00 |

TABLE 39.7

Comparative Data: Intravenous PK Study of PRX-P4-003 (2 and 10 mg/kg b.w.)
and PRX-002(−) Isomer (2 mg/kg b.w.) in Male Sprague Dawley Rats

| Mean Plasma PK Parameters | IV PK Study of PRX-P4-003 (2 mg/kg b.w.) | | IV PK Study of PRX-P4-003 (10 mg/kg b.w.) | | IV PK Study of PRX-002 (−) Isomer (1 mg/kg b.w.) |
|---|---|---|---|---|---|
| | Mean PK Parameters of PRX-P4-003 | Mean PK Parameters of PRX-002 (−) Isomer | Mean PK Parameters of PRX-P4-003 | Mean PK Parameters of PRX-002 (−) Isomer | Mean PK Parameters of PRX-002 (−) Isomer |
| Dose (mg/kg b.w.) | 2 | 2 | 10 | 10 | 2 |
| $C^{max}$ (ng/ml) | 171.963 ± 62.6030 | 30.807 ± 10.0830 | NC | NC | 142.973 ± 1.7520 |
| $T^{max}$ (hr) | 0.080 ± 0.0000 | 0.080 ± 0.0000 | NC | NC | 0.137 ± 0.0980 |
| $AUC^{last}$ (hr * ng/ml) | 132.573 ± 32.5110 | 14.254 ± 3.8510 | NC | NC | 218.525 ± 23.9320 |
| $AUC^{inf}$ (hr * ng/ml) | 215.708 ± 83.3890 | 22.098 ± 7.0600 | NC | NC | 256.001 ± 44.2920 |
| $AUC^{\%\ extrap}$ (%) | 32.475 ± 83.3890 | 34.822 ± 6.9490 | NC | NC | 14.056 ± 5.0710 |
| Vss (L/kg) | 41.984 ± 19.8767 | 86.814 ± 23.2576 | NC | NC | 15.726 ± 0.3391 |
| CL (mL/min/kg) | 171.947 ± 69.3217 | 1606.391 ± 464.8270 | NC | NC | 132.632 ± 21.0303 |
| $T^{1/2}$ (hr) | 3.348 ± 2.1780 | 0.682 ± 0.2440 | NC | NC | 1.512 ± 0.2230 |
| $MRT^{last}$ (hr) | 1.836 ± 0.7130 | 0.340 ± 0.0190 | NC | NC | 1.328 ± 0.1180 |

Figure 4:
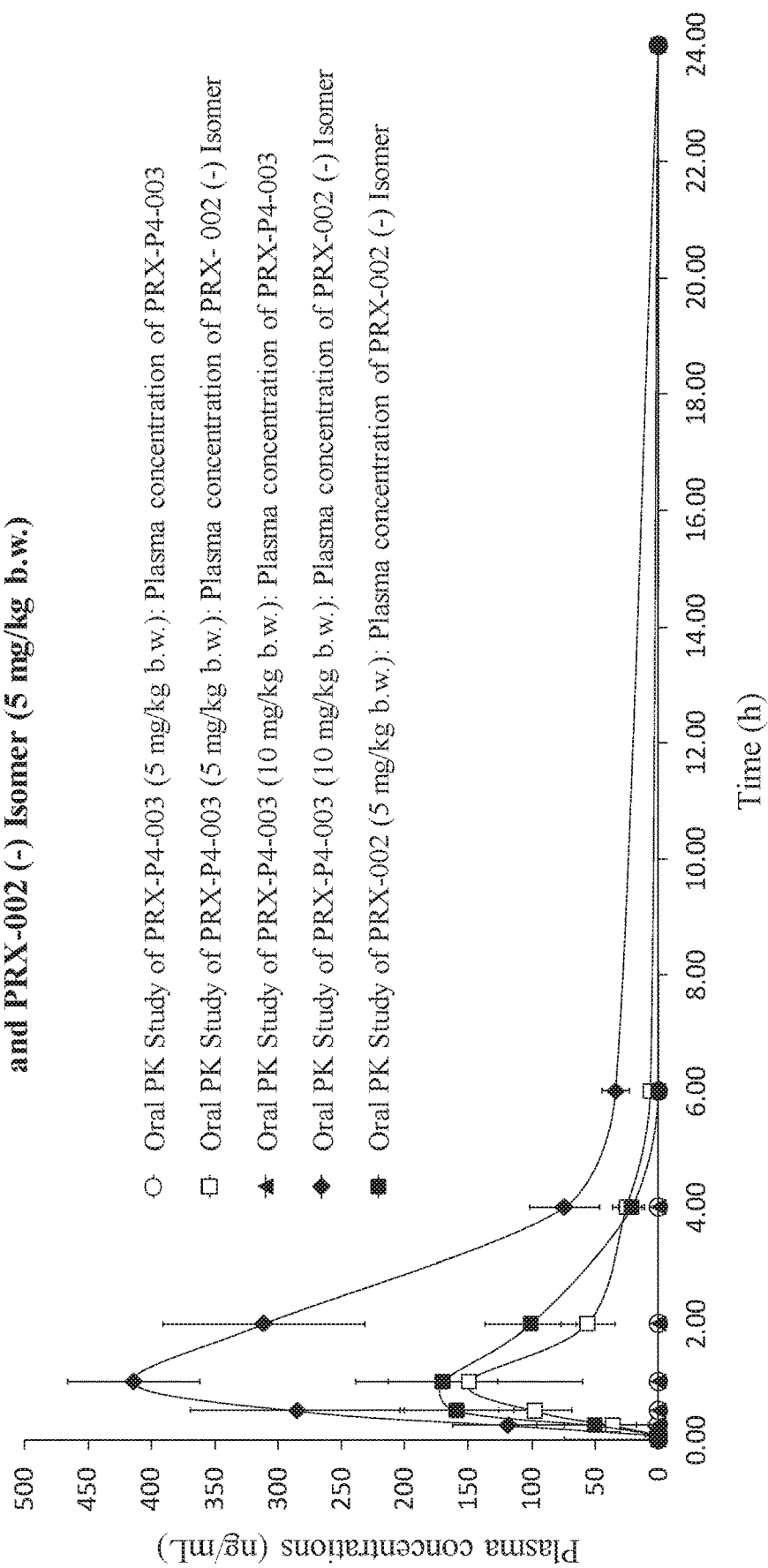
FIG. 4 is a graph comparing the oral PK study of PRX-P4-003 to PRX-002(−) isomer, in terms of the amount of resulting PRX-P4-003 or PRX-P4-002(−) isomer present in the plasma.

*NC: Not Calculated.
PRX-P4-003 IV 10 mg/kg PK data analysis was not carried out because limited exposure in plasma concentration profile FIG. 4 is a graph comparing the oral PK study of PRX-4-003 to PRX-002(−) isomer, in terms of the amount of resulting PRX-4-003 or PRX-P4-002(−) isomer present in the plasma. As can be seen from the results, almost none of the prodrug form of the drug (PRX-P4-003) is present in the plasma when administered orally. However, a desired amount of the active compound (PRX-002 (−) Isomer) does form in the plasma. Additional data is presented in Table 39.8-39.9

TABLE 39.8

ORAL PK STUDY OF PRX-P4-003 (5 AND 10 MG/KG) AND PRX-002(−) (5 MG/KG)IN MALE SPRAGUE DAWLEYRATS. MEAN PK PARAMETERS OF PRX-P4-003 AND PRX-002 (−) ISOMER

| | Oral PK Study of PRX-P4-003 (5 mg/kg) | | Oral PK Study of PRX-P4-003 (10 mg/kg) | | Oral PK Study of PRX-002 (−) Isomer (5 mg/kg) |
|---|---|---|---|---|---|
| | A | B | C | D | E |
| Dose (mg/kg) | 5.0 | 5.0 | 10.0 | 10.00 | 5.0 |
| $C_{max}$ (ng/mL) | 0.0 | 156.7030 ± 85.32600 | 0.0 | 425.0400 ± 40.46000 | 176.260 ± 47.4850 |
| $T_{max}$ (hr) | 0.0 | 0.8330 ± 0.28900 | 0.0 | 1.3330 ± 0.57700 | 0.833 ± 0.2890 |
| $AUC_{last}$ (hr*ng/mL) | 0.0 | 296.8610 ± 51.2400 | 0.0 | 1092.8470 ± 169.08500 | 370.968 ± 99.4740 |
| $AUC_{inf}$ (hr*ng/mL) | 0.0 | 308.8410 ± 58.24000 | 0.0 | 1158.6130 ± 137.93700 | 427.201 ± 122.1840 |
| $AUC_{\%\ extrap}$(%) | 0.0 | 3.6430 ± 2.29800 | 0.0 | 5.9310 ± 3.20800 | 12.904 ± 1.8410 |
| $T_{1/2}$ (hr) | 0.0 | 1.8080 ± 0.30700 | 0.0 | 1.9220 ± 0.09300 | 1.864 ± 0.132 |
| $MRT_{last}$ (hr) | 0.0 | 1.2770 ± 0.25600 | 0.0 | 1.2890 ± 0.29000 | 1.474 ± 0.1040 |

A: Mean PK Parameters of PRX-P4-003
B: Mean PK Parameters of PRX-002 (−) Isomer
C: Mean PK Parameters of PRX-P4-003
D: Mean PK Parameters of PRX-002 (−) Isomer
E: Mean PK Parameters of PRX-002 (−) Isomer

TABLE 39.9

Comparative Data: Oral PK Study of PRX-P4-003 (5 and 10 mg/kg b.w.) and PRX-002 (−) Isomer (5 mg/kg b.w.) in Male Sprague Dawley Rats

| | Oral PK Study of PRX-P4-003 (5 mg/kg b.w.) | | | | Oral PK Study of PRX-P4-003 (10 mg/kg b.w.) | | | | Oral PK Study of PRX-002 (−) Isomer (5 mg/kg b.w.) | | |
|---|---|---|---|---|---|---|---|---|---|---|---|
| | Plasma concentration of PRX-P4-003 | | Plasma concentration of PRX-002 (−) Isomer | | Plasma concentration of PRX-P4-003 | | Plasma concentration of PRX-002 (−) Isomer | | Plasma concentration of PRX-002 (−) Isomer | | |
| Time h) | Mean | SD | Mean | SD | Mean | ± SD | Mean | ± SD | Mean | ± | SD |
| 0.00 | 0.00 ± | 0.00 | 0.00 ± | 0.00 | 0.00 ± | 0.00 | 0.00 ± | 0.00 | 0.00 | ± | 0.00 |
| 0.08 | 0.00 ± | 0.00 | 0.00 ± | 0.00 | 0.00 ± | 0.00 | 2.52 ± | 4.37 | 0.00 | ± | 0.00 |
| 0.25 | 0.00 ± | 0.00 | 35.89 ± | 18.38 | 0.00 ± | 0.00 | 118.79 ± | 44.28 | 50.20 | ± | 45.98 |

TABLE 39.9-continued

Comparative Data: Oral PK Study of PRX-P4-003 (5 and 10 mg/kg b.w.) and PRX-002 (−) Isomer (5 mg/kg b.w.) in Male Sprague Dawley Rats

| | Oral PK Study of PRX-P4-003 (5 mg/kg b.w.) | | | | Oral PK Study of PRX-P4-003 (10 mg/kg b.w.) | | | | Oral PK Study of PRX-002 (−) Isomer (5 mg/kg b.w.) | |
|---|---|---|---|---|---|---|---|---|---|---|
| | Plasma concentration of PRX-P4-003 | | Plasma concentration of PRX-002 (−) Isomer | | Plasma concentration of PRX-P4-003 | | Plasma concentration of PRX-002 (−) Isomer | | Plasma concentration of PRX-002 (−) Isomer | |
| Time h) | Mean | SD | Mean | SD | Mean ± SD | | Mean ± SD | | Mean ± SD | |
| 0.50 | 0.00 ± 0.00 | | 97.56 ± 29.02 | | 0.00 ± 0.00 | | 285.18 ± 84.86 | | 159.35 ± 44.89 | |
| 1.00 | 0.00 ± 0.00 | | 149.74 ± 89.23 | | 0.00 ± 0.00 | | 414.87 ± 52.27 | | 170.35 ± 43.09 | |
| 2.00 | 0.00 ± 0.00 | | 56.12 ± 21.49 | | 0.00 ± 0.00 | | 312.47 ± 78.99 | | 101.07 ± 36.25 | |
| 4.00 | 0.00 ± 0.00 | | 25.08 ± 11.71 | | 0.00 ± 0.00 | | 74.52 ± 27.56 | | 21.30 ± 10.18 | |
| 6.00 | 0.00 ± 0.00 | | 6.10 ± 3.79 | | 0.00 ± 0.00 | | 33.82 ± 10.45 | | 0.00 ± 0.00 | |
| 24.00 | 0.00 ± 0.00 | | 0.00 ± 0.00 | | 0.00 ± 0.00 | | 0.00 ± 0.00 | | 0.00 ± 0.00 | |

Figure 5A:
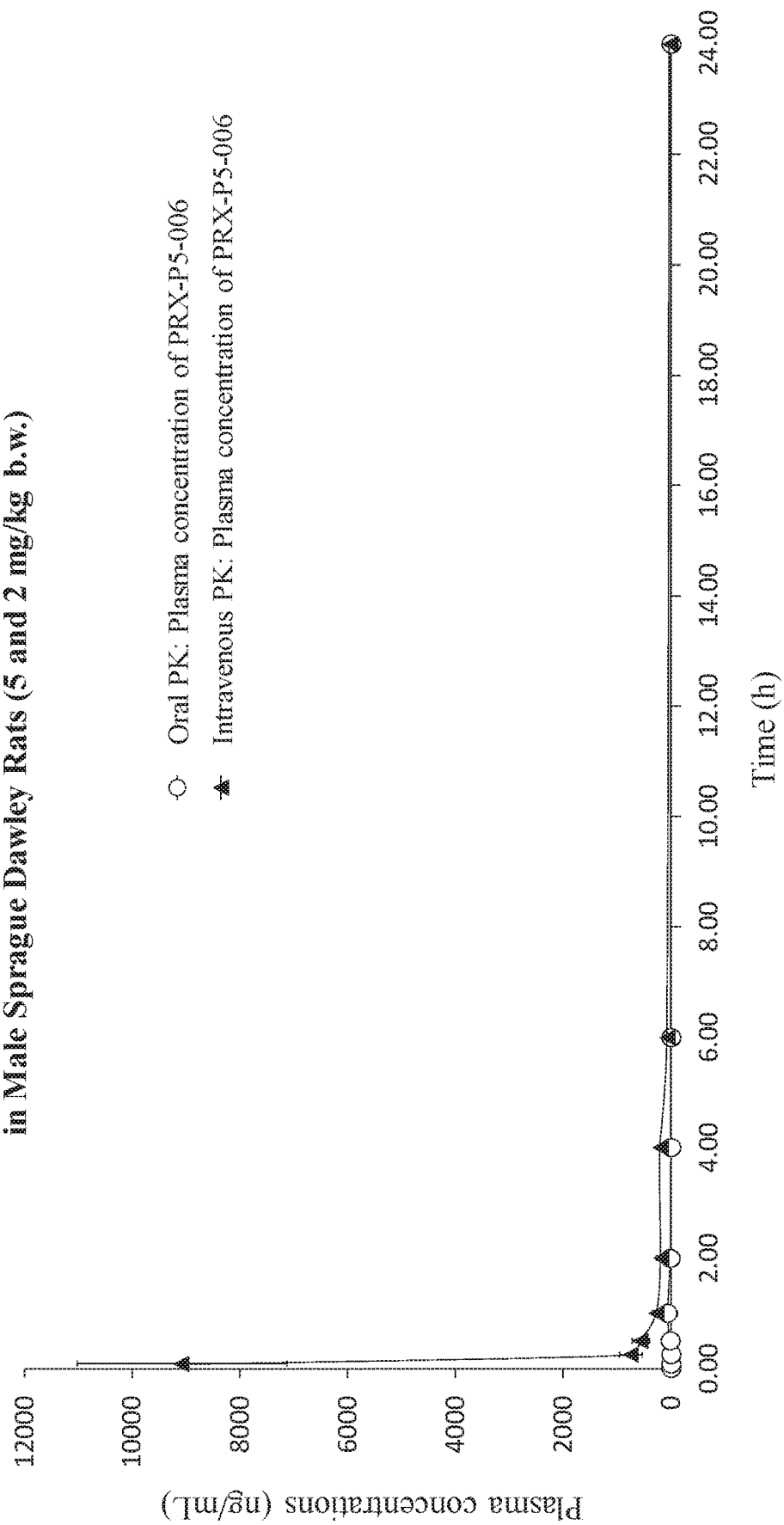
FIGS. 5A and 5B show comparative Data: Single Dose Oral and Intravenous PK Study of PRX-P5-006.
Figure 5B:
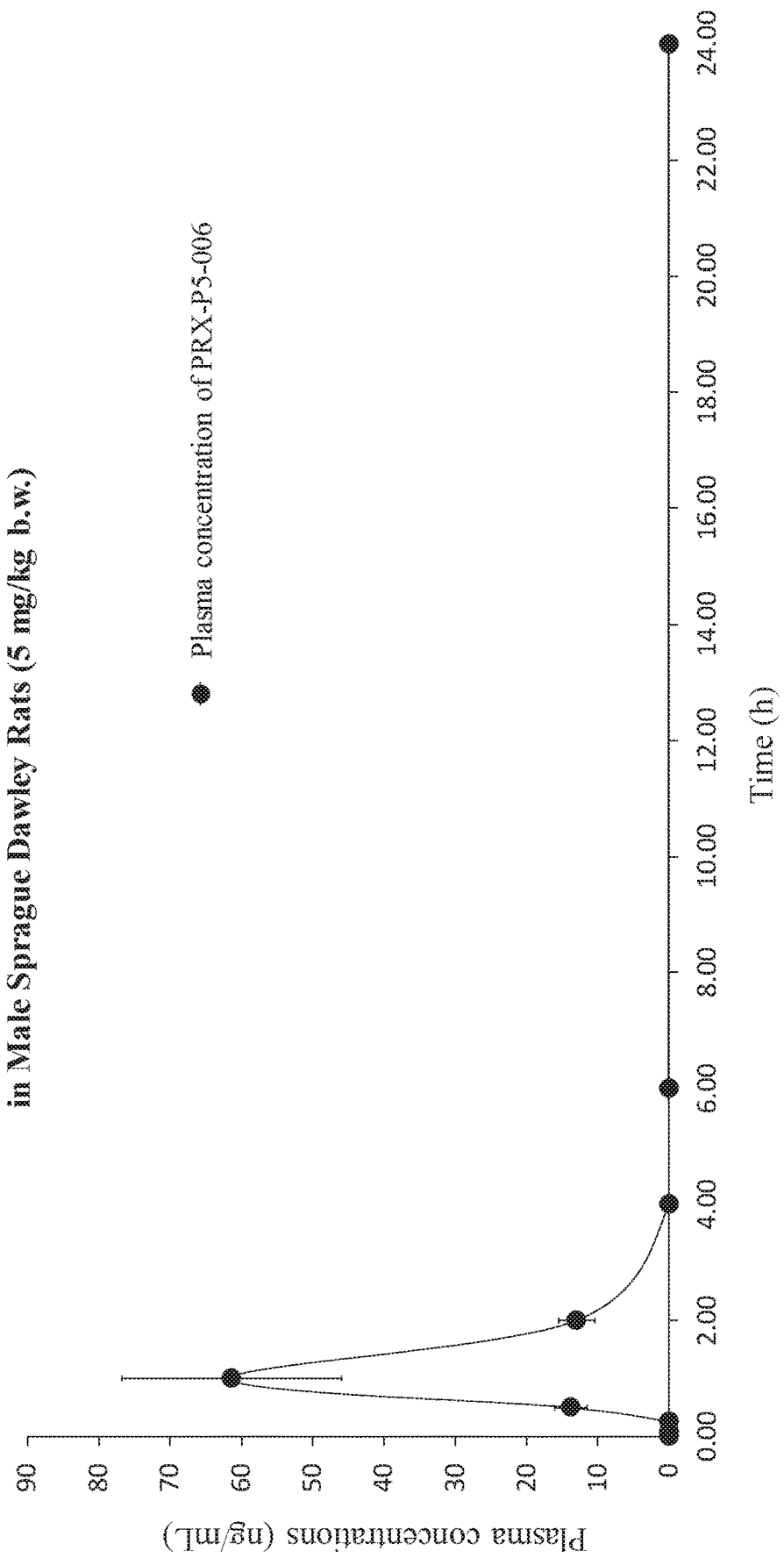

FIGS. 5A and 5B shows comparative Data: Single Dose Oral and Intravenous PK Study of PRX-P5-006. Much higher level of intact PRX-P5-006 was observed when prodrug was administered IV. The data is shown in Table 39.10. Additional data is shown in Tables 39.11-39.12

TABLE 39.10

Single Dose Oral and Intravenous PK Study of PRX-P5-006 in Male Sprague Dawley Rats-amount of prodrug remaining in plasma

| PK Parameters | Oral Mean Plasma PK Parameters of PRX-P5-006 | Intravenous |
|---|---|---|
| Dose (mg/kg) | 5.00 | 2.00 |
| $C_{max}$ (ng/mL) | 61.457 ± 15.4180 | 9097.783 ± 1947.6780 |
| $T_{max}$ (hr) | 1.000 ± 0.0000 | 0.08 ± 0.0000 |
| $AUC_{last}$ (hr*ng/mL) | 57.800 ± 10.1940 | 4267.485 ± 902.3590 |
| $AUC_{inf}$ (hr*ng/mL) | 114.633 ± 23.3260 | 4563.103 ± 894.4610 |
| $AUC_{\%\ extrap}$ (%) | 47.896 ± 15.3010 | 6.602 ± 4.0330 |
| Vss (L/kg) | — | 1.875 ± 1.4500 |
| CL (mL/min/kg) | — | 7.478 ± 1.3221 |
| $T_{1/2}$ (hr) | 2.907 ± 0.865 | 6.304 ± 3.7850 |
| $MRT_{last}$ (hr) | 1.070 ± 0.0250 | 2.313 ± 1.2350 |

TABLE 39.11

Single Dose Oral Pharmacokinetics Study of PRX-P5-006 in Male Sprague Dawley Rats (5 mg/kg b.w.)

| Animal No | $C_{max}$ (ng/mL) | $T_{max}$ (hr) | $AUC_{last}$ (hr*ng/mL) | $AUC_{inf}$ (hr*ng/mL) | $AUC_{\%\ extrap}$ | $MRT_{last}$ (hr) | $T_{1/2}$ (hr) |
|---|---|---|---|---|---|---|---|
| R001 | 43.87 | 1.00 | 46.56 | 122.60 | 62.02 | 1.10 | 3.50 |
| R002 | 72.65 | 1.00 | 66.44 | 132.93 | 50.02 | 1.07 | 3.31 |
| R003 | 67.85 | 1.00 | 60.40 | 88.37 | 31.64 | 1.05 | 1.91 |
| N | 3 | 3 | 3 | 3 | 3 | 3 | 3 |
| Mean | 61.457 | 1.000 | 57.800 | 114.633 | 47.896 | 1.070 | 2.907 |
| SD | 15.4180 | 0.0000 | 10.1940 | 23.3260 | 15.3010 | 0.0250 | 0.865 |

TABLE 39.12

Single Dose IV Pharmacokinetics Study of PRX-P5-006 in Male Sprague Dawley Rats (2 mg/kg b.w.)

| Animal No | $C_0$ (ng/ml) | $C_{max}$ (ng/mL) | $T_{max}$ (hr) | $AUC_{last}$ (hr*ng/mL) | $AUC_{inf}$ (hr*ng/mL) | $AUC_{\%\ extrap}$ | Vss (L/kg) | CL (mL/min/kg) | $MRT_{last}$ (hr) | $T_{1/2}$ (hr) |
|---|---|---|---|---|---|---|---|---|---|---|
| R001 | 36229.68 | 11226.34 | 0.08 | 5304.3 | 5592.69 | 5.16 | 1.56 | 5.96 | 2.7 | 7.54 |
| R002 | 32467.12 | 8662.3 | 0.08 | 3838.58 | 3977.39 | 3.49 | 0.61 | 8.38 | 0.93 | 2.06 |
| R003 | 21202.31 | 7404.71 | 0.08 | 3659.58 | 4119.23 | 11.16 | 3.46 | 8.09 | 3.31 | 9.32 |
| N | 3 | 3 | 3 | 3 | 3 | 3 | 3 | 3 | 3 | 3 |
| Mean | 29966.370 | 9097.783 | 0.08 | 4267.485 | 4563.103 | 6.602 | 1.875 | 7.478 | 2.313 | 6.304 |
| SD | 7819.5760 | 1947.6780 | 0.0000 | 902.3590 | 894.4610 | 4.0330 | 1.4500 | 1.3221 | 1.2350 | 3.7850 |

Figure 6A:
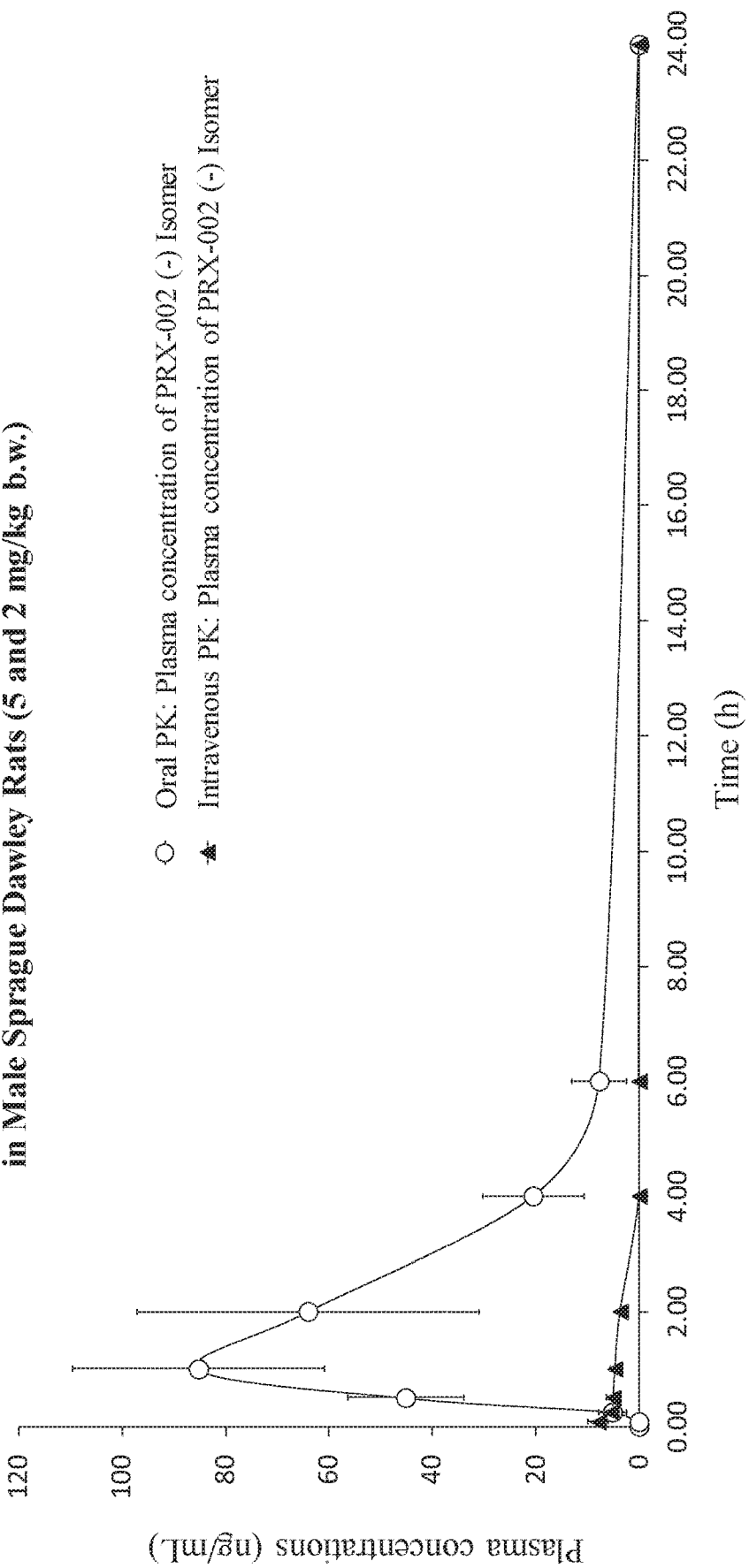
FIG. 6A is a graph depicting a comparison of oral and IV pharmacokinetics of PRX-P5-006 in Male Sprague Dawley rats.
Figure 6B:
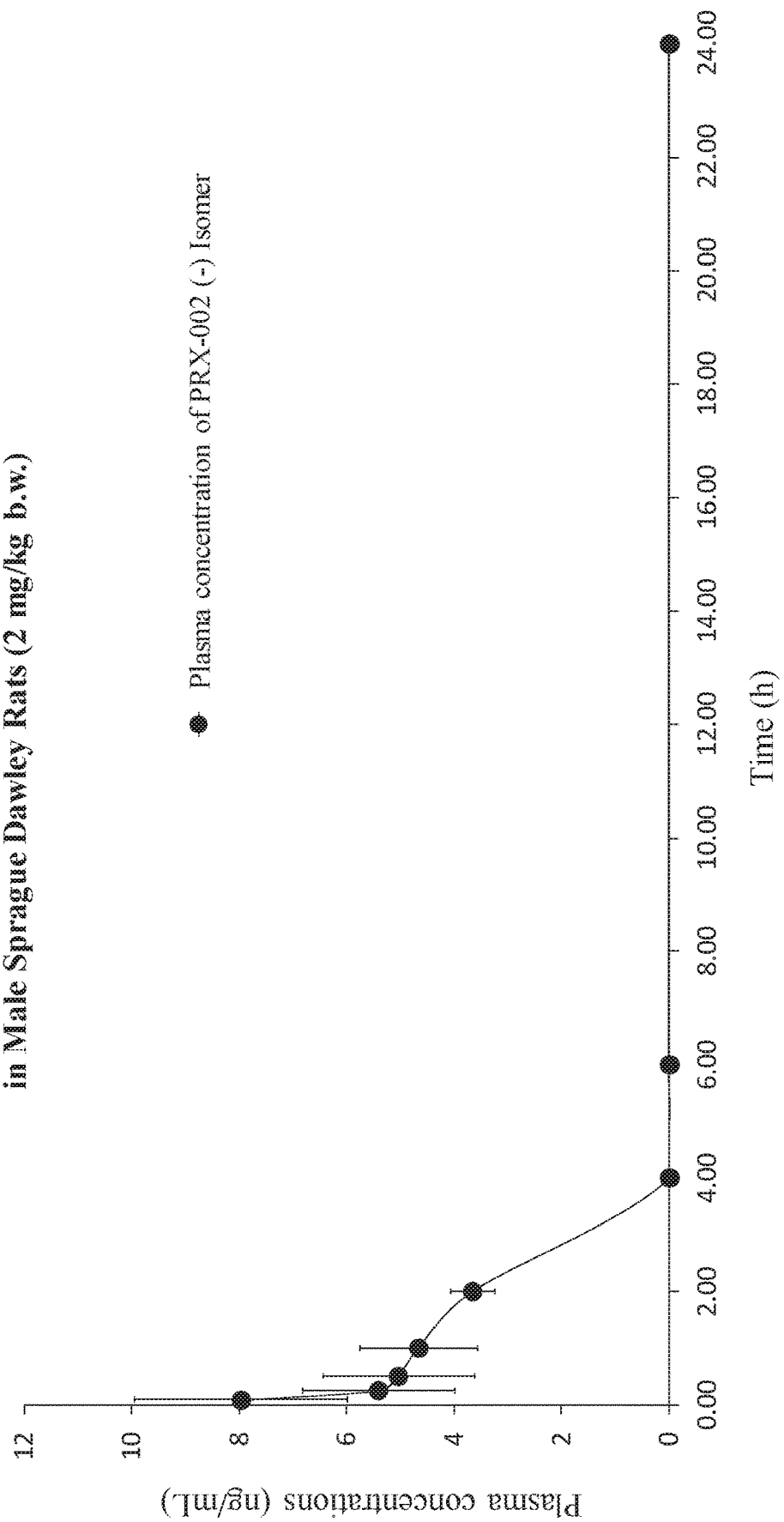
FIG. 6B shows an enlarged view of the IV pharmacokinetics for the amount of resulting active in the plasma depicted in FIG. 6A.

FIG. 6A is a graph depicting a comparison of oral and IV pharmacokinetics of PRX-P5-006 in Male Sprague Dwaley rats. FIG. 6B shows an enlarged view of the IV pharmacokinetics for the amount of resulting active in the plasma depicted in 6A. The graph depicts the amount of the active compound found in the plasma over time for the PRX-P5-006 compound. The data is shown in Table 39.13, below. Additional data is shown below in Tables 39.14-39.17.

TABLE 39.13

COMPARATIVE DATA: SINGLE DOSE ORAL AND INTRAVENOUS PK STUDY OF PRX-P5-006
Single Dose Oral and Intravenous PK Study of PRX-P5-006 in Male Sprague Dawley Rats

| PK Parameters | Oral | Intravenous |
|---|---|---|
| | Mean Plasma PK Parameters of PRX-002 | |
| Dose (mg/kg) | 5.00 | 2.00 |
| $C_{max}$ (ng/mL) | 85.297 ± 24.4150 | 7.980 ± 1.9800 |
| $T_{max}$ (hr) | 1.000 ± 0.0000 | 0.08 ± 0.0000 |
| $AUC_{last}$ (hr*ng/mL) | 226.99 ± 92.8790 | 9.750 ± 1.6650 |
| $AUC_{inf}$ (hr*ng/mL) | 241.836 ± 104.0180 | 21.703 ± 2.1980 |
| $AUC_{\% extrap}$ (%) | 5.645 ± 1.8560 | 54.877 ± 7.6450 |
| Vss (L/kg) | — | 304.212 ± 49.9758 |
| CL (mL/min/kg) | — | 1547.056 ± 165.4562 |
| $T_{1/2}$ (hr) | 1.290 ± 0.137 | 2.248 ± 0.2880 |
| $MRT_{last}$ (hr) | 2.061 ± 0.1540 | 0.874 ± 0.0360 |

TABLE 39.14

Single Dose Oral Pharmacokinetics Study of PRX-P5-006 in Male Sprague Dawley Rats (5 mg/kg b.w.)
Plasma concentration of PRX-002 (ng/mL)

| Group No. | Time (h) | R001 | R002 | R003 | Mean | SD |
|---|---|---|---|---|---|---|
| G-1 | 0.00 | 0.00 | 0.00 | 0.00 | 0.000 | 0.000 |
| | 0.08 | 0.00 | 0.00 | 0.00 | 0.000 | 0.000 |
| | 0.25 | 2.82 | 8.21 | 4.47 | 5.167 | 2.761 |
| | 0.50 | 32.44 | 49.39 | 53.68 | 45.169 | 11.230 |
| | 1.00 | 67.50 | 113.13 | 75.26 | 85.296 | 24.414 |
| | 2.00 | 55.44 | 100.65 | 36.19 | 64.096 | 33.089 |
| | 4.00 | 16.59 | 31.81 | 13.28 | 20.561 | 9.884 |
| | 6.00 | 4.82 | 13.82 | 4.56 | 7.735 | 5.269 |
| | 24.00 | 0.00 | 0.00 | 0.00 | 0.000 | 0.000 |

LLOQ—Lower Limit Of Quantification of PRX-002 in plasma-2.167 ng/mL

TABLE 39.15

Single Dose Oral Pharmacokinetics Study of PRX-P5-006 in Male Sprague Dawley Rats (5 mg/kg b.w.)

| Animal No | $C_{max}$ (ng/mL) | $T_{max}$ (hr) | $AUC_{last}$ (hr*ng/mL) | $AUC_{inf}$ (hr*ng/mL) | $AUC_{\% extrap}$ | $MRT_{last}$ (hr) | $T_{1/2}$ (hr) |
|---|---|---|---|---|---|---|---|
| R001 | 67.50 | 1.00 | 184.54 | 192.44 | 4.10 | 2.09 | 1.14 |
| R002 | 113.13 | 1.00 | 333.51 | 361.35 | 7.70 | 2.20 | 1.40 |
| R003 | 75.26 | 1.00 | 162.92 | 171.72 | 5.13 | 1.90 | 1.34 |
| N | 3 | 3 | 3 | 3 | 3 | 3 | 3 |
| Mean | 85.297 | 1.000 | 226.99 | 241.836 | 5.645 | 2.061 | 1.29 |
| SD | 24.4150 | 0.0000 | 92.8790 | 104.0180 | 1.8560 | 0.1540 | 0.137 |

TABLE 39.16

(PLASMA CONCENTRATION OF ACTIVE)
Single Dose Intravenous Pharmacokinetics Study of PRX-P5-006 in Male Sprague Dawley Rats (2 mg/kg b.w.)
Plasma concentration of PRX-002 (ng/mL)

| Group No. | Time (h) | R004 | R005 | R006 | Mean | SD |
|---|---|---|---|---|---|---|
| G-2 | 0.08 | 9.53 | 5.75 | 8.66 | 7.981 | 1.979 |
| | 0.25 | 7.02 | 4.32 | 4.92 | 5.419 | 1.415 |
| | 0.50 | 6.49 | 4.99 | 3.66 | 5.047 | 1.412 |
| | 1.00 | 5.60 | 4.93 | 3.47 | 4.666 | 1.092 |
| | 2.00 | 3.82 | 3.20 | 4.00 | 3.673 | 0.417 |
| | 4.00 | 0.00 | 0.00 | 0.00 | 0.000 | 0.000 |
| | 6.00 | 0.00 | 0.00 | 0.00 | 0.000 | 0.000 |
| | 24.00 | 0.00 | 0.00 | 0.00 | 0.000 | 0.000 |

LLOQ—Lower Limit Of Quantification of PRX-002 in plasma- 2.167 ng/mL

TABLE 39.17

(PLASMA CONCENTRATION OF ACTIVE)
Single Dose IV Pharmacokinetics Study of
PRX-P5-006 in Male Sprague Dawley Rats (2 mg/kg b.w.)

| Animal No | $C_0$ (ng/ml) | $C_{max}$ (ng/mL) | $T_{max}$ (hr) | $AUC_{last}$ (hr*ng/mL) | $AUC_{inf}$ (hr*ng/mL) | $AUC_{\%\,extrap}$ | Vss (L/kg) | CL (mL/min/kg) | $MRT_{last}$ (hr) | $T_{1/2}$ (hr) |
|---|---|---|---|---|---|---|---|---|---|---|
| R001 | 11.00 | 9.53 | 0.08 | 11.65 | 22.61 | 48.47 | 246.74 | 1474.36 | 0.83 | 1.99 |
| R002 | 6.58 | 5.75 | 0.08 | 9.06 | 19.20 | 52.82 | 328.45 | 1736.41 | 0.90 | 2.20 |
| R003 | 11.30 | 8.66 | 0.08 | 8.54 | 23.30 | 63.34 | 337.45 | 1430.39 | 0.89 | 2.56 |
| N | 3 | 3 | 3 | 3 | 3 | 3 | 3 | 3 | 3 | 3 |
| Mean | 9.627 | 7.980 | 0.080 | 9.750 | 21.703 | 54.877 | 304.212 | 1547.056 | 0.874 | 2.248 |
| SD | 2.6450 | 1.9800 | 0.0000 | 1.6650 | 2.1980 | 7.6450 | 49.9758 | 165.4562 | 0.0360 | 0.2880 |

Figure 7A:
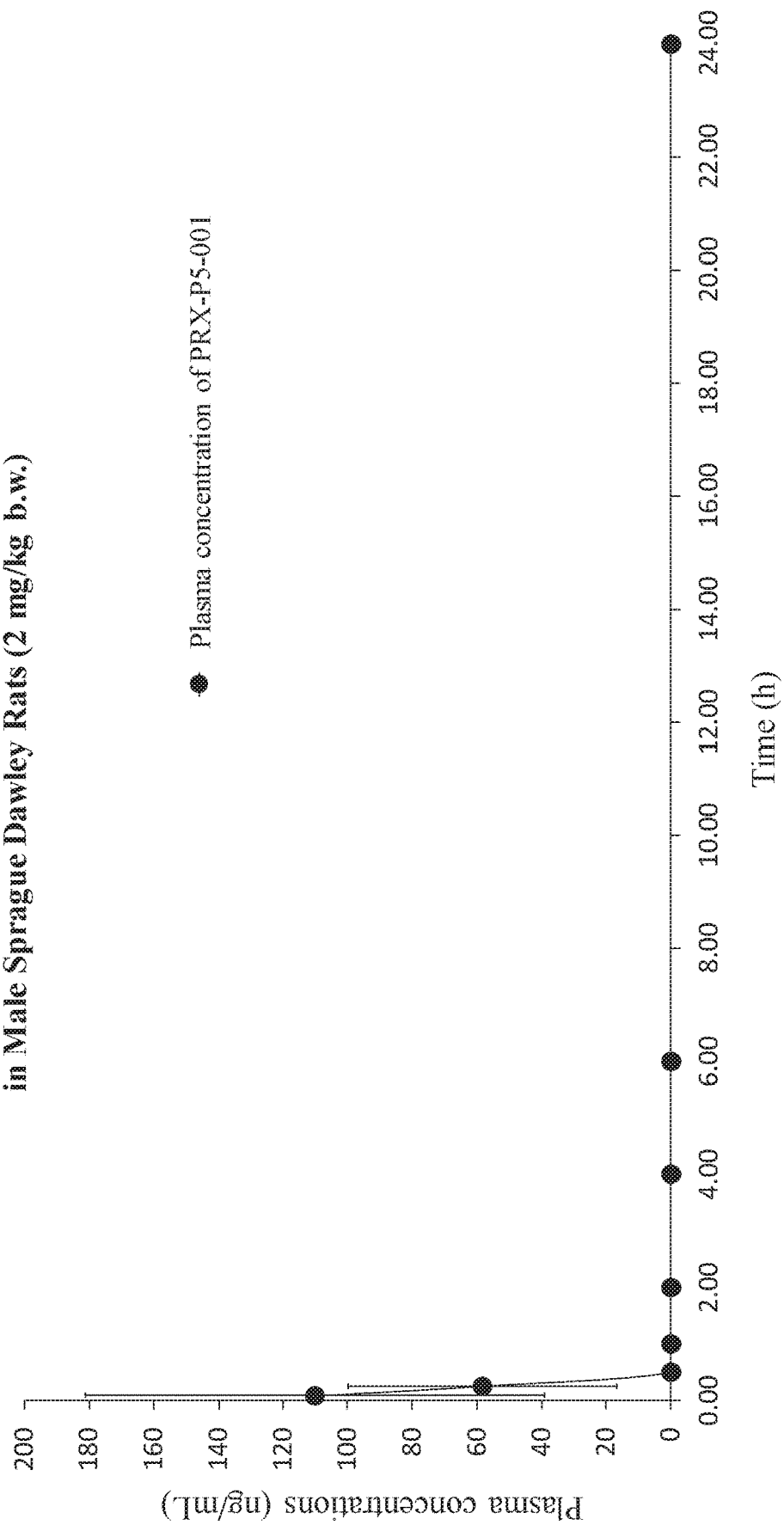
FIGS. 7A and 7B show graph depicting the IV pharmacokinetics for PRX-P5-011 in male Sprague Dawley rats.
Figure 7B:
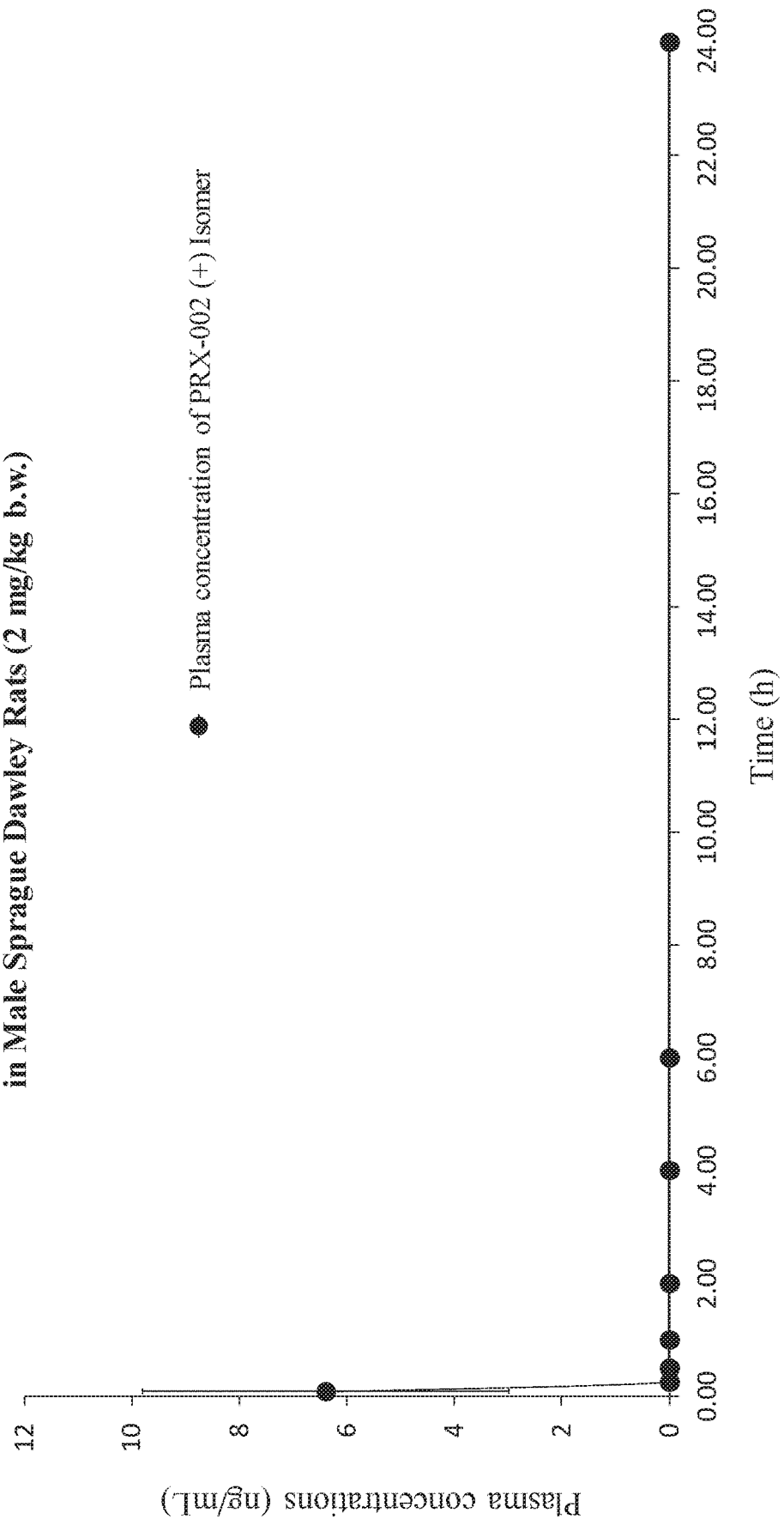

FIGS. 7A and 7B show graph depicting the IV pharmacokinetics for PRX-P5-011 in male Sprague Dawley rats. Even though the only difference between PRX-P5-011 and PRX-P5-006 is that the former has positive isomer PRX-002 (+) while the latter has PRX-002 (−) the oral plasma profile is remarkably different. The active compound PRX-002 (+) was not detected in plasma after oral administration. The results are summarized above from table 39.18-39.21

TABLE 39.18

SINGLE DOSE ORAL PHARMACOKINETIC STUDY OF
PRX-P5-011PLASMA CONCENTRATIONS OF PRX-P5-011
IN MALE SPRAGUE DAWLEY RATS.
Plasma concentration of PRX-P5-011 (ng/mL)

| Time (h) | R010 | R011 | R012 | Mean | SD |
|---|---|---|---|---|---|
| 0.00 | 0.00 | 0.00 | 0.00 | 0.000 | 0.000 |
| 0.08 | 0.00 | 0.00 | 0.00 | 0.000 | 0.000 |
| 0.25 | 0.00 | 0.00 | 0.00 | 0.000 | 0.000 |
| 0.50 | 0.00 | 0.00 | 0.00 | 0.000 | 0.000 |
| 1.00 | 0.00 | 0.00 | 0.00 | 0.000 | 0.000 |
| 2.00 | 0.00 | 0.00 | 0.00 | 0.000 | 0.000 |
| 4.00 | 0.00 | 0.00 | 0.00 | 0.000 | 0.000 |
| 6.00 | 0.00 | 0.00 | 0.00 | 0.000 | 0.000 |
| 24.00 | 0.00 | 0.00 | 0.00 | 0.000 | 0.000 |

LLOQ—Lower Limit Of Quantification of PRX-P5-011 in plasma-3.373 ng/mL

TABLE 39.19

SINGLE DOSE ORAL PHARMACOKINETIC STUDY OF
PRX-P5-011 PLASMA CONCENTRATIONS OF PRX-002 (+)
ISOMER IN MALE SPRAGUE DAWLEY RATS.
Plasma concentration of PRX-002 (+) Isomer (ng/mL)

| Time (h) | R010 | R011 | R012 | Mean | SD |
|---|---|---|---|---|---|
| 0.00 | 0.00 | 0.00 | 0.00 | 0.000 | 0.000 |
| 0.08 | 0.00 | 0.00 | 0.00 | 0.000 | 0.000 |
| 0.25 | 0.00 | 0.00 | 0.00 | 0.000 | 0.000 |
| 0.50 | 0.00 | 0.00 | 0.00 | 0.000 | 0.000 |
| 1.00 | 0.00 | 0.00 | 0.00 | 0.000 | 0.000 |
| 2.00 | 0.00 | 0.00 | 0.00 | 0.000 | 0.000 |
| 4.00 | 0.00 | 0.00 | 0.00 | 0.000 | 0.000 |
| 6.00 | 0.00 | 0.00 | 0.00 | 0.000 | 0.000 |
| 24.00 | 0.00 | 0.00 | 0.00 | 0.000 | 0.000 |

LLOQ—Lower Limit Of Quantification of PRX-002 (+) Isomer in plasma-1.779 ng/mL

TABLE 39.20

Single Dose Intravenous Pharmacokinetics Study of
PRX-P5-011 in Male Sprague Dawley Rats (2 mg/kg b.w.)
Plasma concentration of PRX-P5-011 (ng/mL)

| Group No. | Time (h) | R013 | R014 | R015 | Mean | SD |
|---|---|---|---|---|---|---|
| G-2 | 0.08 | 114.77 | 37.09 | 179.14 | 110.332 | 71.132 |
|  | 0.25 | 56.47 | 17.98 | 101.04 | 58.497 | 41.563 |
|  | 0.50 | 0.00 | 0.00 | 0.00 | 0.000 | 0.000 |
|  | 1.00 | 0.00 | 0.00 | 0.00 | 0.000 | 0.000 |
|  | 2.00 | 0.00 | 0.00 | 0.00 | 0.000 | 0.000 |
|  | 4.00 | 0.00 | 0.00 | 0.00 | 0.000 | 0.000 |
|  | 6.00 | 0.00 | 0.00 | 0.00 | 0.000 | 0.000 |
|  | 24.00 | 0.00 | 0.00 | 0.00 | 0.000 | 0.000 |

LLOQ—Lower Limit Of Quantification of PRX-P5-011 in plasma-3.373 ng/mL

TABLE 39.21

SINGLE DOSE IV PHARMACOKINETIC STUDY
OF PRX-P5-011. PLASMA CONCENTRATIONS OF PRX-002 (+)
ISOMER IN MALE SPRAGUE DAWLEY RATS.
Single Dose Intravenous Pharmacokinetics Study of
PRX-P5-011 in Male Sprague Dawley Rats (2 mg/kg b.w.)
Plasma concentration of PRX-002 (+) Isomer (ng/mL)

| Group No. | Time (h) | R013 | R014 | R015 | Mean | SD |
|---|---|---|---|---|---|---|
| G-2 | 0.08 | 8.92 | 2.52 | 7.77 | 6.400 | 3.409 |
|  | 0.25 | 0.00 | 0.00 | 0.00 | 0.000 | 0.000 |
|  | 0.50 | 0.00 | 0.00 | 0.00 | 0.000 | 0.000 |
|  | 1.00 | 0.00 | 0.00 | 0.00 | 0.000 | 0.000 |
|  | 2.00 | 0.00 | 0.00 | 0.00 | 0.000 | 0.000 |
|  | 4.00 | 0.00 | 0.00 | 0.00 | 0.000 | 0.000 |
|  | 6.00 | 0.00 | 0.00 | 0.00 | 0.000 | 0.000 |
|  | 24.00 | 0.00 | 0.00 | 0.00 | 0.000 | 0.000 |

LLOQ—Lower Limit of Quanitfication of RPX-002 (+) Isomer in plasma-1.779 ng/mL

Figure 8A:
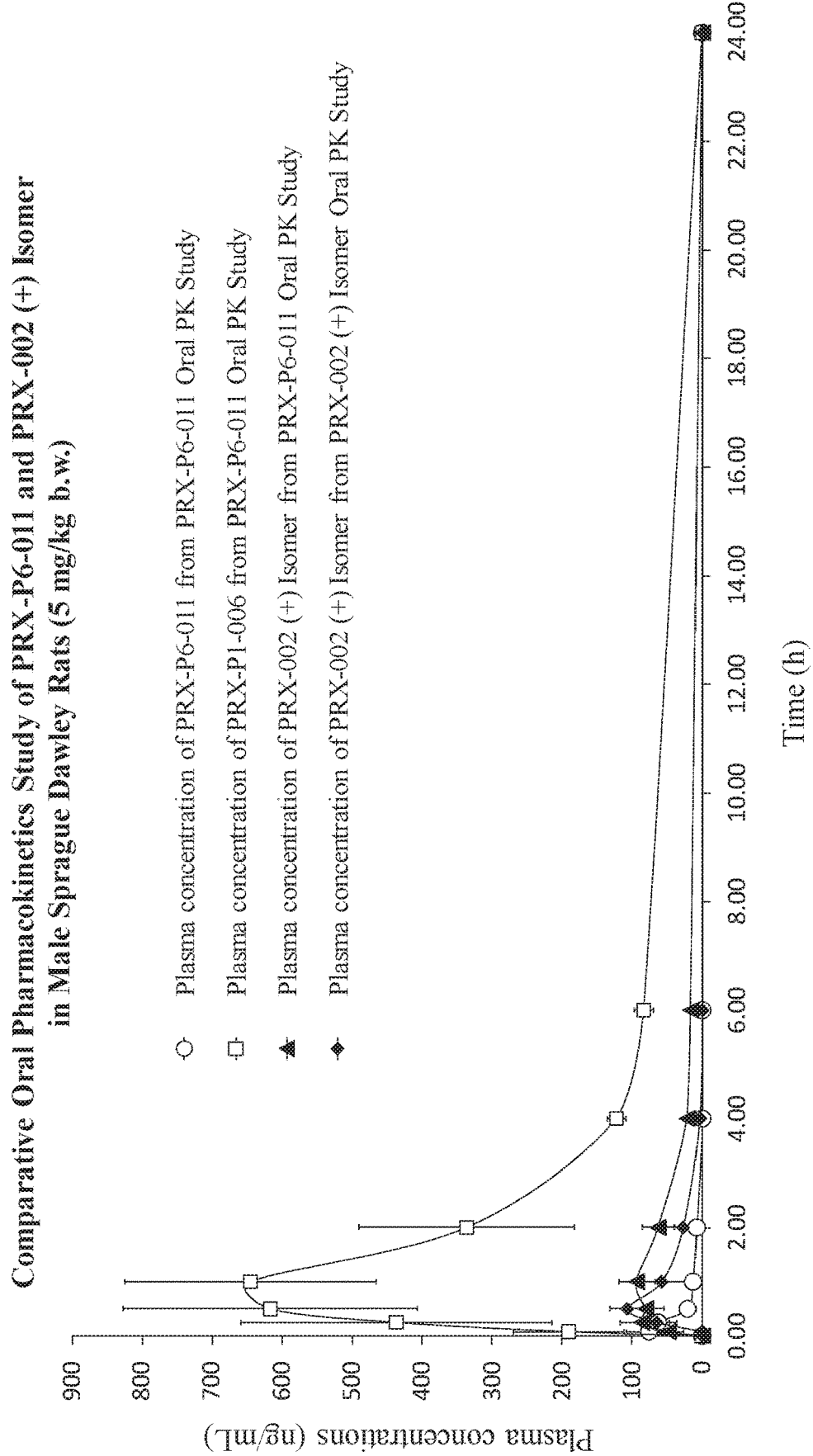
FIG. 8A is a graph depicting the IV pharmacokinietics of PRX-P6-011 in male Sprague Dawley rats.
Figure 8B:
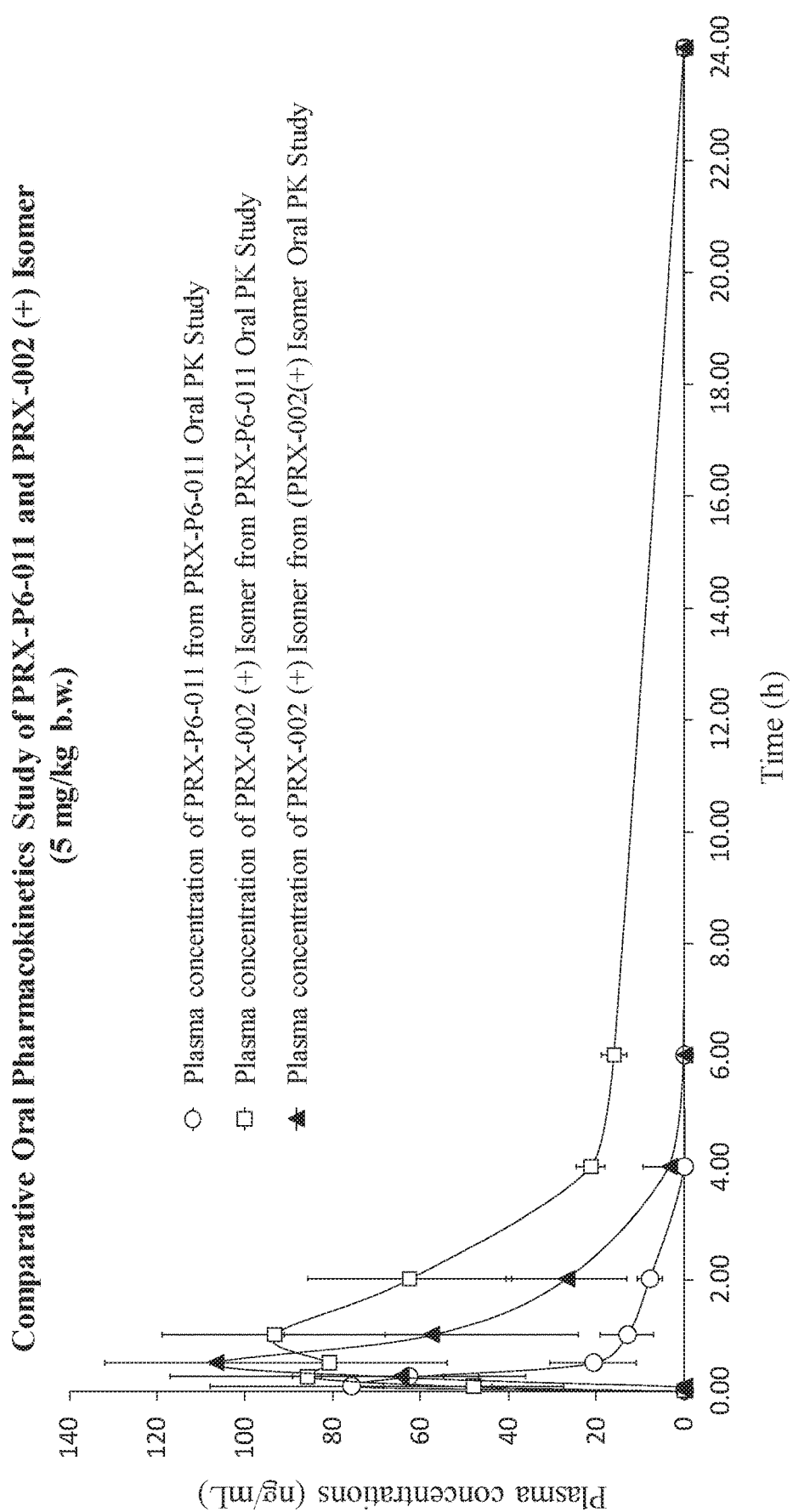
FIG. 8B is a more closely visualized graph (from 8A) consisting of PRX-P6-011, PRX-002 (+) [compared to the level of PRX-002 (−) after direct administration].

FIG. 8A is a graph depicting the IV pharmacokinietics of PRX-P6-011 in male Sprague Dawley rats. FIG. 8B is a more closely visualized graph (from 8A) consisting of PRX-P6-011, PRX-002 (+) [compared to the level of PRX-002 (−) after direct administration]. The results are summarized in tables 39.22-39.25.

Tables 39.22-39.25 provide comparative oral pharmacokinetics study results for PRX-P6-011 and PRX-002(+), including mean plasma PK parameters of PRX-P6-011, PRX-P1-006, PRX-002(+).

TABLE 39.22

| | Oral PK Study of PRX-P6-011 | | | Oral PK Study of PRX-002 (+) Isomer |
|---|---|---|---|---|
| | PRX-P6-011 | PRX-P1-006(monopeptide) | PRX-002(+) Isomer | PRX-002(+) Isomer |
| Dose (mg/kg) | 5.00 | 5.00 | 5.00 | 5.00 |
| $C_{max}$ (ng/mL) | 82.223 ± 30.8790 | 655.283 ± 193.0510 | 94.637 ± 26.1330 | 106.727 ± 25.432 |
| $T_{max}$ (hr) | 0.137 ± 0.0980 | 0.833 ± 0.2890 | 0.750 ± 0.4330 | 0.5 ± 0.0 |
| $AUC_{last}$ (hr*ng/mL) | 44.161 ± 17.0700 | 1664.557 ± 363.7590 | 277.359 ± 69.7760 | 127.924 ± 74.239 |
| $AUC_{inf}$ (hr*ng/mL) | 57.261 ± 21.2510 | 1914.634 ± 367.6390 | 336.298 ± 37.4560 | 151.444 ± 68.603 |
| $AUC_{\%\,extrap}$ (%) | 23.190 ± 3.6640 | 13.391 ± 2.6780 | 18.346 ± 13.2530 | 18.063 ± 11.646 |
| $T_{1/2}$ (hr) | 1.172 ± 0.2110 | 2.120 ± 0.3850 | 2.433 ± 1.0880 | 0.992 ± 0.228 |
| $MRT_{last}$ (hr) | 0.575 ± 0.0370 | 1.885 ± 0.2180 | 2.002 ± 0.2090 | 0.957 ± 0.269 |

TABLE 39.23

Single Dose Oral Pharmacokinetics Study of PRX-P6-011 in Male Sprague Dawley Rats (5 mg/kg b.w.)

| | Plasma concentrations of PRX-P6-011 (ng/mL) | | | Plasma concentrations of PRX-P1-006 (ng/mL) | | | Plasma concentrations of PRX-002 (+) Isomer (ng/mL) | | |
|---|---|---|---|---|---|---|---|---|---|
| Time (h) | Mean | ± | SD | Mean | ± | SD | Mean | ± | SD |
| 0.00 | 0.00 | ± | 0.00 | 0.00 | ± | 0.00 | 0.00 | ± | 0.00 |
| 0.08 | 75.92 | ± | 32.13 | 191.07 | ± | 79.19 | 48.07 | ± | 20.49 |
| 0.25 | 62.77 | ± | 26.46 | 437.17 | ± | 222.28 | 86.02 | ± | 31.17 |
| 0.50 | 20.78 | ± | 9.87 | 617.34 | ± | 209.88 | 80.97 | ± | 26.95 |
| 1.00 | 13.01 | ± | 6.06 | 645.99 | ± | 179.41 | 93.49 | ± | 25.37 |
| 2.00 | 7.87 | ± | 2.93 | 336.43 | ± | 153.72 | 62.66 | ± | 23.23 |
| 4.00 | 0.00 | ± | 0.00 | 122.45 | ± | 13.35 | 21.38 | ± | 3.32 |
| 6.00 | 0.00 | ± | 0.00 | 83.31 | ± | 13.47 | 16.05 | ± | 2.98 |
| 24.00 | 0.00 | ± | 0.00 | 0.00 | ± | 0.00 | 0.00 | ± | 0.00 |

35

TABLE 39.24

Single Dose Oral PK Study of PRX-002 (+isomer) at 5 mg/kg body weight in Male Sprague Dawley Rats

| Animal ID | $C_{max}$ (ng/mL) | $T_{max}$ (hr) | $AUC_{last}$ (hr*ng/mL) | $AUC_{inf}$ (hr*ng/mL) | $AUC_{\%\,extrap}$ | $MRT_{last}$ (hr) | $T_{1/2}$ (hr) |
|---|---|---|---|---|---|---|---|
| R0175 | 134.89 | 0.5 | 213.62 | 229.43 | 6.89 | 1.26 | 1.07 |
| R0176 | 85.44 | 0.5 | 87 | 124.51 | 30.13 | 0.86 | 1.17 |
| R0177 | 99.85 | 0.5 | 83.16 | 100.4 | 17.17 | 0.75 | 0.74 |
| N | 3 | 3 | 3 | 3 | 3 | 3 | 3 |
| Mean | 106.727 | 0.5 | 127.924 | 151.444 | 18.063 | 0.957 | 0.992 |
| SD | 25.432 | 0 | 74.239 | 68.603 | 11.646 | 0.269 | 0.228 |

TABLE 39.25

Single Dose Oral PK Study of PRX-002 (+isomer) at 5 mg/kg body weight in Male Sprague Dawley Rats Mean Plasma PK Parameters

| Parameters | PRX-002 (+isomer) |
|---|---|
| Dose (mg/kg b.w.) | 5.00 |
| $C_{max}$ (ng/mL) | 106.727 ± 25.432 |
| $T_{max}$ (hr) | 0.5 ± 0.0 |
| $AUC_{last}$ (hr*ng/mL) | 127.924 ± 74.239 |
| $AUC_{inf}$ (hr*ng/mL) | 151.444 ± 68.603 |
| $AUC_{\%\,extrap}$ (%) | 18.063 ± 11.646 |
| $T_{1/2}$ (hr) | 0.992 ± 0.228 |
| $MRT_{last}$ (hr) | 0.957 ± 0.269 |

Figure 9A:
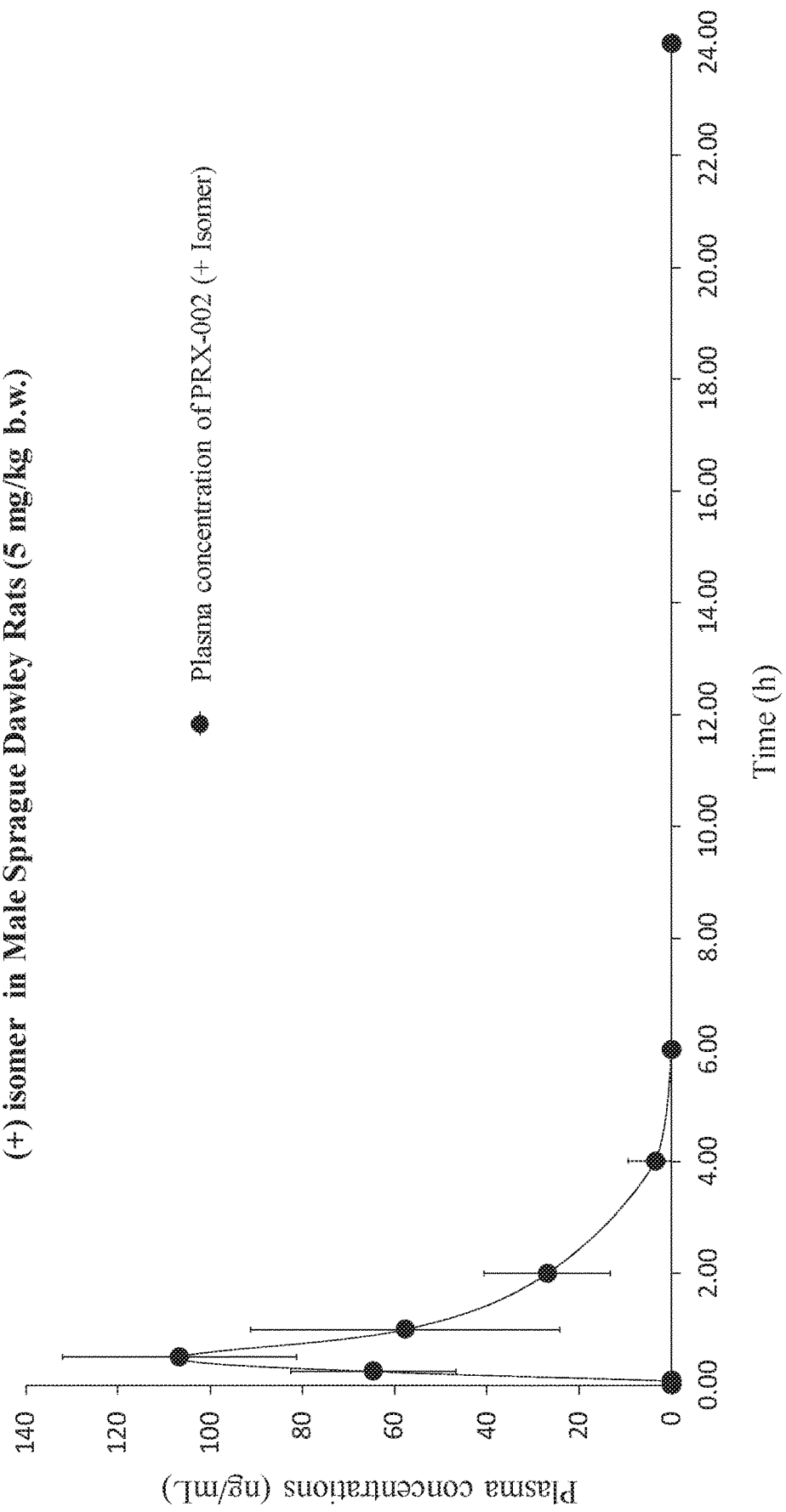
FIGS. 9A, 9B, and 9C show graph of PRX-002 (+) administered to the rats at a dose of 5 mg kg orally or 2 mg/kg intravenously.
Figure 9B:
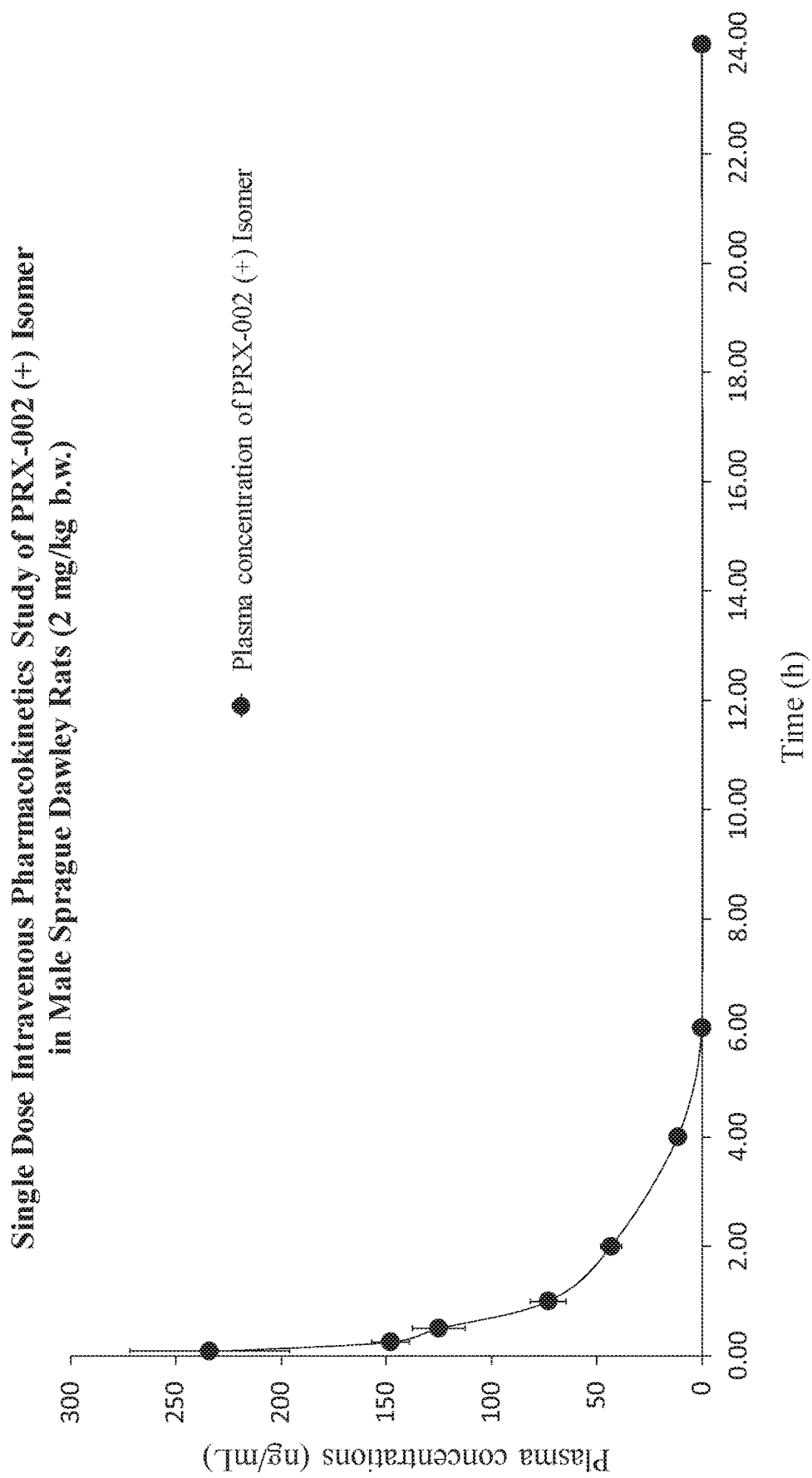
Figure 9C:
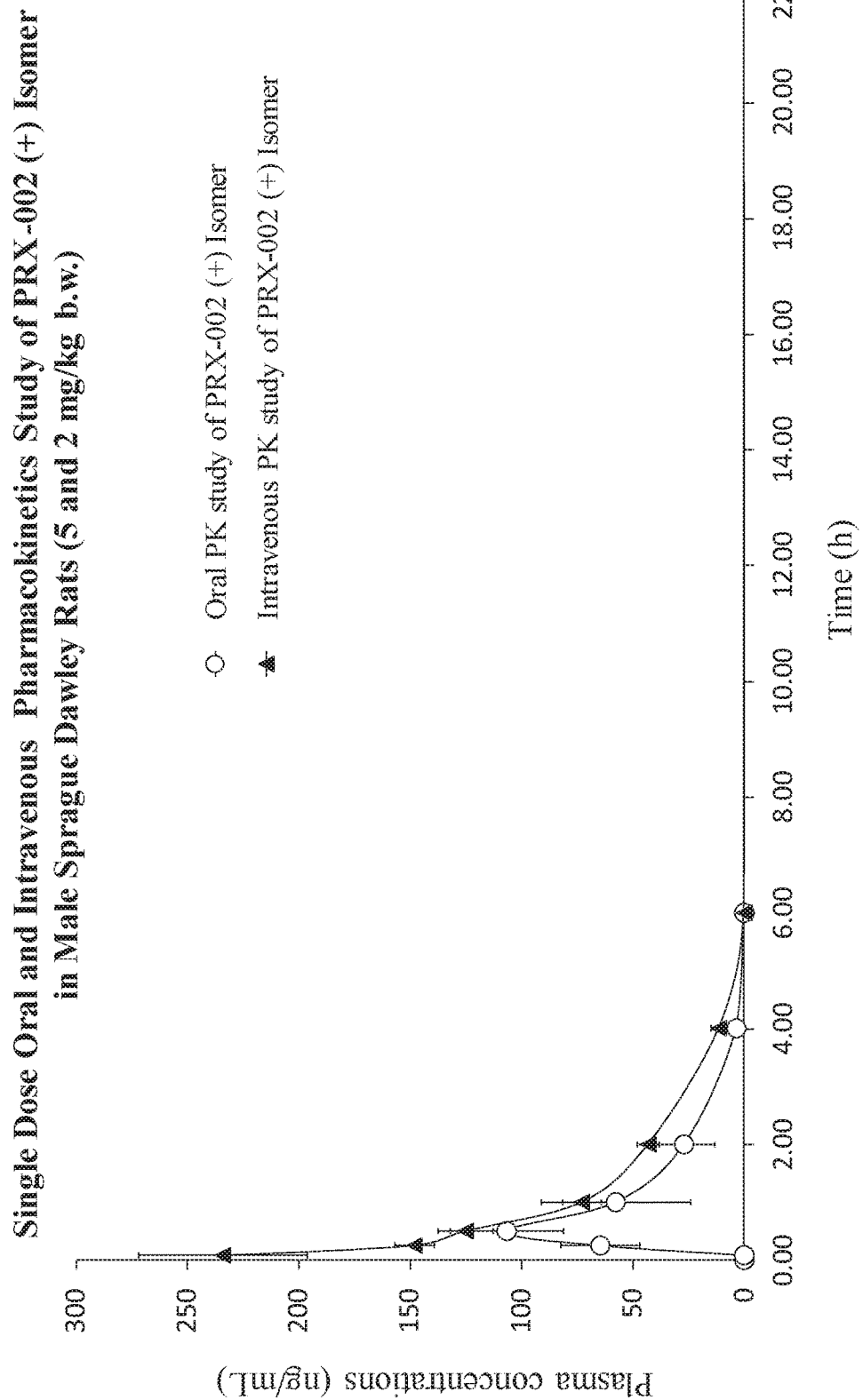

FIGS. 9 A, B, and C show graph of PRX-002 (+) administered to the rats at a dose of 5 mg kg orally or 2 mg/kg intravenously. Tables 39.26 and 39.27 show the detailed oral and IV PK parameters.

TABLE 39.26

Single Dose Oral PK Study of PRX-002 (+isomer) at 5 mg/kg body weight in Male Sprague Dawley Rats Mean Plasma PK Parameters

| Parameters | PRX-002 (+isomer) |
|---|---|
| Dose (mg/kg b.w.) | 5 |
| $C_{max}$ (ng/ml) | 106.727 ± 25.432 |
| $T_{max}$ (hr) | 0.5 ± 0.0 |
| $AUC_{last}$ (hr * ng/ml) | 127.924 ± 74.239 |

TABLE 39.26-continued

Single Dose Oral PK Study of PRX-002 (+isomer)
at 5 mg/kg body weight in Male Sprague Dawley Rats
Mean Plasma PK Parameters

| Parameters | PRX-002 (+isomer) |
|---|---|
| $AUC_{inf}$ (hr * ng/mL) | 151.444 ± 68.603 |
| $AUC_{\% extrap}$ (%) | 18.063 ± 11.646 |
| $T_{1/2}$ (hr) | 0.992 ± 0.228 |
| $MRT_{last}$ (hr) | 0.957 ± 0.269 |

TABLE 39.27

Single Dose Intravenous Pharmacokinetic
Study of PRX-002 (+isomer) at 2 mg/kg
body weight in Male Sprague Dawley Rats
Mean Plasma PK Parameters

| Parameters | PRX-002 (+isomer) |
|---|---|
| Route of administration | IV |
| Dose (mg/kg b.w.) | 2 |
| $C_{max}$ (ng/ml) | 234.12 ± 37.91 |
| $C_0$ (ng/ml) | 291.216 ± 61.772 |
| $T_{max}$ (hr) | 0.08 ± 0.0 |
| $AUC_{last}$ (hr * ng/ml) | 249.661 ± 15.19 |
| $AUC_{inf}$ (hr * ng/mL) | 267.82 ± 23.486 |
| $AUC_{extrap}$ (%) | 6.639 ± 2.427 |
| Vss (L/kg) | 10.07 ± 0.51 |
| CL (mL/min/kg) | 125.08 ± 10.58 |
| $T_{1/2}$ (h) | 1.082 ± 0.152 |
| $MRT_{last}$ (h) | 1.05 ± 0.071 |

Figure 10A:
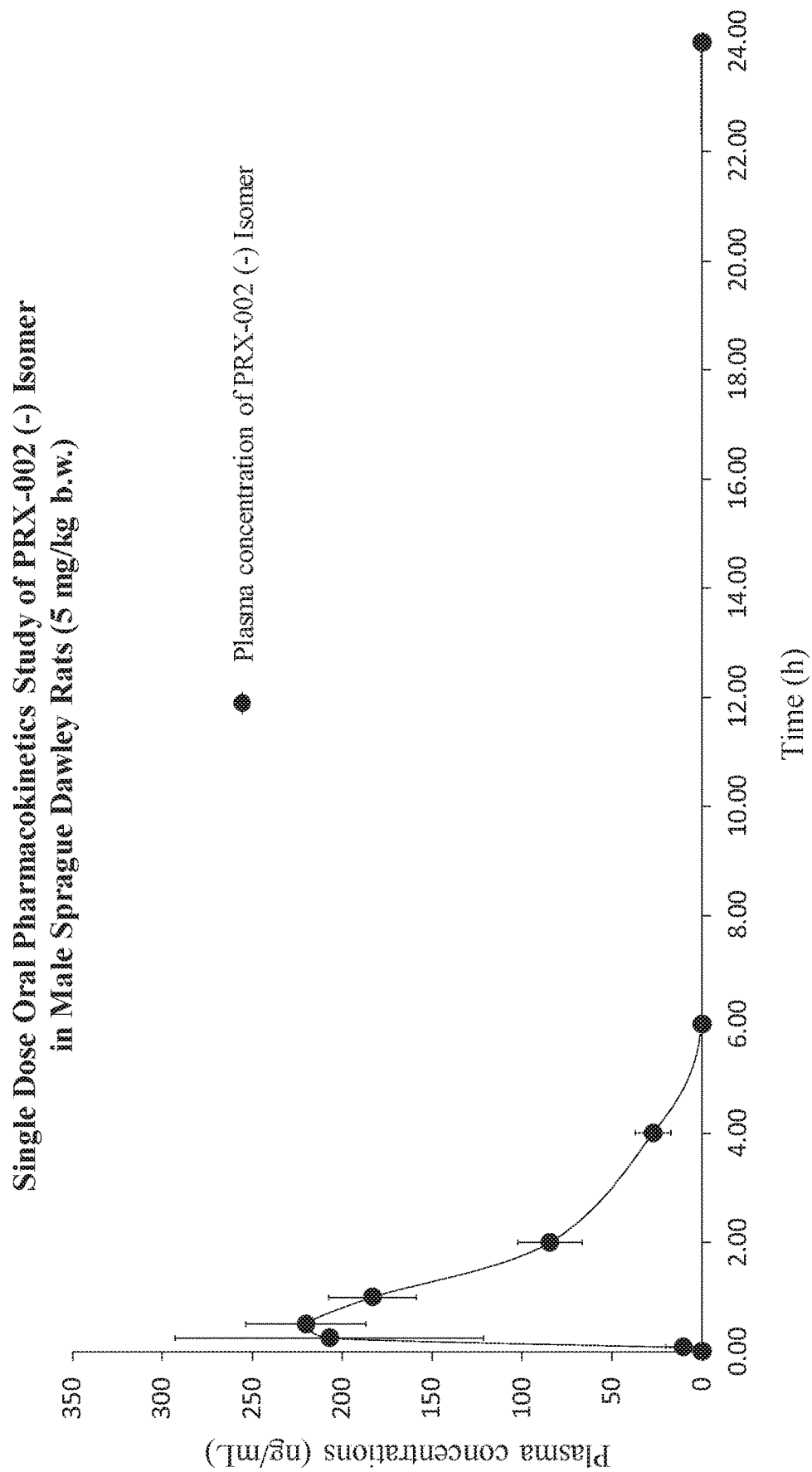
FIGS. 10A, 10B, and 10C show graph of PRX-002 (−) administered to the rats at a dose of 5 mg kg orally or 2 mg/kg intravenously.
Figure 10B:
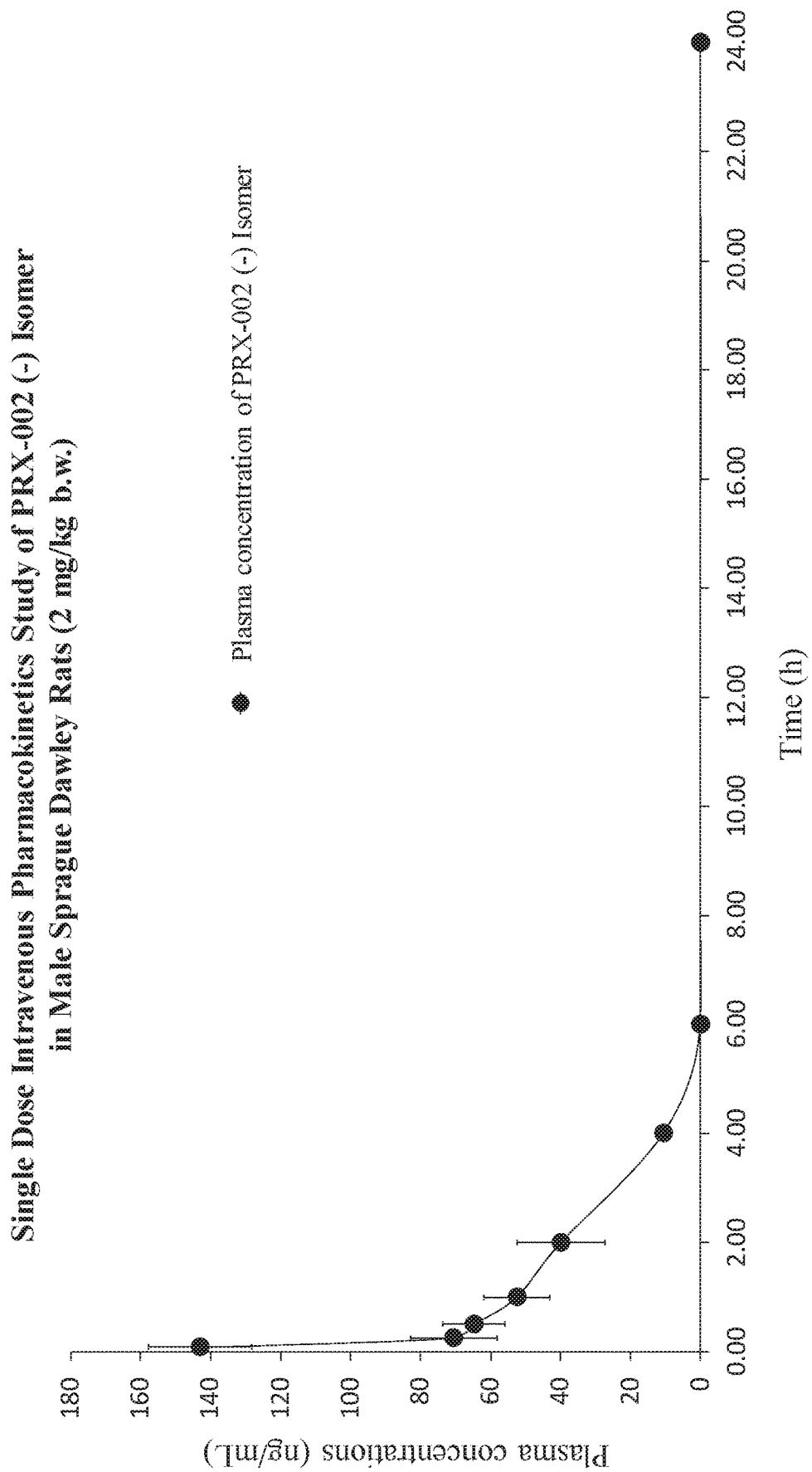
Figure 10C:
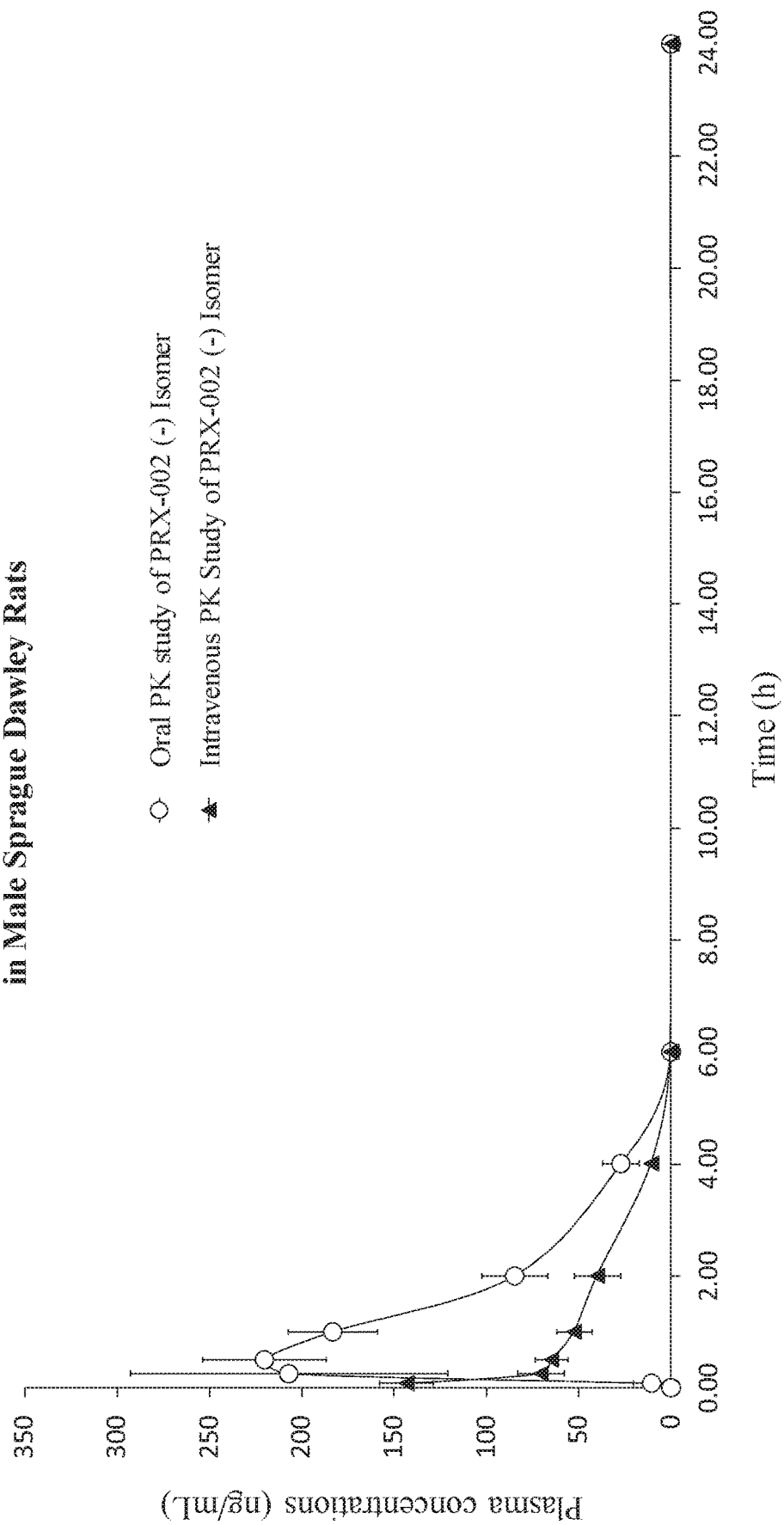

FIGS. 10 A, B, and C show graph of PRX-002 (−) administered to the rats at a dose of 5 mg kg orally or 2 mg/kg intravenously. Tables 39.28 and 39.29 show the detailed oral/IV PK parameters.

TABLE 39.28

Single Dose Oral Pharmacokinetic Study of PRX-002
(−isomer) at 5 mg/kg body weight in Male Sprague Dawley Rats
Mean Plasma PK Parameters

| Parameters | PRX-002 (−isomer) |
|---|---|
| Dose (mg/kg b.w.) | 5 |
| $C_{max}$ (ng/ml) | 231.87 ± 43.45 |
| $T_{max}$ (hr) | 0.5 ± 0.433 |
| $AUC_{last}$ (hr * ng/mL) | 419.097 ± 56.744 |
| $AUC_{inf}$ (hr * ng/ml) | 464.727 ± 51.635 |
| $AUC \%_{extrap}$ (%) | 9.856 ± 5.812 |
| $T_{1/2}$ (hr) | 1.112 ± 0.235 |
| $MRT_{last}$ (hr) | 1.321 ± 0.135 |

TABLE 39.29

Single Dose Intravenous Pharmacokinetic
Study of PRX-002 (−isomer) at 2 mg/kg
body weight in Male Sprague Dawley Rats
Mean Plasma PK Parameters

| Parameters | PRX-002 (−isomer) |
|---|---|
| Route of administration | IV |
| Dose (mg/kg b.w.) | 2 |
| $C_{max}$ (ng/ml) | 143.117 ± 14.745 |
| C0 (ng/ml) | 199.942 ± 15.654 |
| $T_{max}$ (hr) | 0.08 ± 0.00 |
| $AUC_{last}$ (hr * ng/ml) | 174.92 ± 27.20 |
| $AUC_{inf}$ (hr * ng/mL) | 195.559 ± 22.32 |
| $AUC_{extrap}$ (%) | 10.853 ± 4.23 |
| Vss (L/kg) | 18.39 ± 4.50 |

TABLE 39.29-continued

Single Dose Intravenous Pharmacokinetic
Study of PRX-002 (−isomer) at 2 mg/kg
body weight in Male Sprague Dawley Rats
Mean Plasma PK Parameters

| Parameters | PRX-002 (−isomer) |
|---|---|
| CL (mL/min/kg) | 172.018 ± 20.611 |
| $T_{1/2}$ (h) | 1.343 ± 0.239 |
| $MRT_{Last}$ (h) | 1.248 ± 0.036 |

The plasma concentrations of fencamfamine were measured by LC-MS/MS over time. TABLE 39.30 and FIGS. 1-10 demonstrate the different PK curves achieved by the different fencamfamine prodrugs as compared with unconjugated forms and the specific pharmacokinetic parameter data is presented in the Tables above and noted figures. The release of fencamfamine from the prodrugs varied depending on the chain length of the fatty acid linkers attached to fencamfamine. Changes in the amount of fencamfamine released from the prodrugs was measured by the area under the curve and compared to unconjugated fencamfamine.

Various prodrug compositions unexpectedly provided an amount sufficient to provide an extended $T_{max}$ when compared to unconjugated fencamfamine when administered at equimolar doses. The prodrug composition showed an extended or controlled release profile as measured by plasma concentrations of released fencamfamine when compared to unconjugated fencamfamine when administered orally at equimolar doses. However, not all of the compounds displayed all or similar such properties.

In some embodiments, the plasma concentration of fencamfamine released from the prodrug increased more slowly and over a longer period of time after oral administration, resulting in a delay in peak plasma concentration of released fencamfamine and in a longer duration of action when compared to unconjugated fencamfamine.

In addition, as shown by some of the embodiments above, the form of the isomer would also alter the pharmacokinetic profile in unexpected ways.

Thus, the type of blocking moiety associated with the drug (e.g., fatty acid or amino acid, etc.), and the particular isomer of fencamfamine used each resulted in varied properties and for the provision of the drug in question.

A summary of the Oral and IV in vivo data in MSD rats for the various compounds is shown below in Table 39.30, which also demonstrates that alternative candidate prodrugs did not have the desired properties or had different properties. Unless otherwise specified all prodrugs were tested with a dose of 5 mg/kg orally and 2 mg/kg IV [equivalent to PRX-002 (−)]. The formulation and administration procedure is as described in the beginning of the PK section.

TABLE 39.30

MEAN PLASMA PK PARAMETERS IN SPRAGUE DAWLEY RATS

| | Oral PK Parameters (5 mg/kg) | | | | | | IV PK Parameters (2 mg/kg) | | | | | |
|---|---|---|---|---|---|---|---|---|---|---|---|---|
| | $C_{max}$ (ng/mL) | | AUC (h*ng/mL) | | $T_{max}$ (h) | | $C_{max}$ (ng/mL) | | AUC (h*ng/mL) | | $T_{max}$ (h) | |
| Compound | Parent | Prodrug | Parent | Prodrug | Parent | Prodrug | Parent | Prodrug | Parent | Prodrug | Parent | Prodrug |
| PRX-002 (−) isomer | 232 ± 43.3 | | 419 ± 56.7 | | 0.5 ± 0.4 | | 143 ± 14.7 | | 175 ± 27.2 | | 0.08 | |
| PRX-002 (+) isomer | 106.7 ± 25.4 | | 127.9 ± 74.2 | | 0.5 ± 0 | | 234.1 ± 37.9 | | 249.7 ± 15.2 | | 0.08 | |
| PRX-P1-005 | 0 | 32 ± 7.5 | 0 | 42 ± 9.4 | 0 | 0.5 | | | study not performed | | | |
| PRX-P1-013 | 0 | 307 ± 49.6 | 0 | 678 ± 101.2 | 0 | 0.7 ± 0.3 | | | study not performed | | | |
| PRX-P4-002 | 347 ± 124.6 | 0 | 718 ± 432.2 | 0 | 0.8 ± 0.3 | 0 | 321 ± 69.2 | 0 | 960 ± 201.3 | 0 | 1.5 ± 0.9 | 0 |
| PRX-P4-003 | 156.7 ± 85.3 | 0 | 296.9 ± 51.2 | 0 | 0.8 ± 0.3 | 0 | 30.8 ± 10.1 | 172.0 ± 62.6 | 14.3 ± 3.85 | 132.6 ± 32.5 | 0.08 ± 0 | 0.08 ± 0 |
| PRX-P5-002 | 267 ± 80.8 | 0 | 234 ± 69.4 | 0 | 0.50 ± 0 | 0 | 360 ± 104.9 | 0 | 161 ± 42.9 | 0 | 0.08 ± 0 | 0 |
| PRX-P5-006 | 66 ± 16.5 | 0 | 186 ± 52.6 | 0 | 1.0 ± 0 | 0 | NC | 707.2 ± 500 | NC | 409.6 ± 301.4 | NC | 0.08 ± 0 |
| PRX-P5-006* | 144 ± 41.5 | 81.6 ± 42.2 | 459 ± 188.5 | 477.4 ± 54.4 | 1.7 ± 0.6 | 0.8 ± 0.3 | 36 ± 5.0 | 16425 ± 7095 | 125 ± 20.6 | 8061.3 ± 1764.8 | 1.0 ± 0 | 0.08 ± 0 |
| PXR-P5-007 | 39 ± 15.9 | ND | 69 ± 32.6 | ND | 0.5 ± 0 | ND | NP | ND | NP | ND | NP | ND |
| PRX-P5-010 | 59.8 ± 15.0 | NC | 125.7 ± 22.3 | NC | 1.0 ± 0 | NC | | | study not performed | | | |
| PRX-P5-011 | 0 | 0 | 0 | 0 | 0 | 0 | | | not calculated | | | |
| PXR-P6-005 | 0 | 721 ± 35.6 | 0 | 2433 ± 174.5 | 0 | 1.0 ± 0 | | | study not performed | | | |
| PXR-P6-006 | 39 ± 1.8 | 198 ± 19.6 | 45 ± 2.6 | 271 ± 64.8 | 0.3 ± 0.1 | 0.3 ± 0.1 | | | study not performed | | | |
| PRX-P6-011 | 94.6 ± 26.1 | 82.2 ± 30.9 | 227.4 ± 69.8 | 44.2 ± 17.1 | 0.75 ± 0.4 | 0.14 ± 0.1 | | | study not performed | | | |

*PK studies performed at 15 mg/kg dose both orally and intravenously;
NP: study not preformed; NC: parameter not calculated: ND: not determined.

Example 40—Oral and Intravenous Pharmacodynamic (Locomotor) Activity

Example 40A. Pharmacodynamic Response (Spontaneous Locomotor Activity) to PRX-P4-003 by Oral Administration Male Sprague-Dawley (SD) were housed in groups of three under controlled conditions. Water and food were available ad libitum. The rats were kept for 1 week under these conditions before behavioral test. On the day of test rats were allowed to acclimate to the testing room for at least 30 min before test compound administration. Rats were randomly assigned into 4 groups.

Vehicle was 0.1% Tween-80 and 0.5% carboxymethylcellulose to which respective amount of PRX-P4-003 was added to obtain a clear solution.

Animals were p.o. administered with Veh or 3 doses of PRX-P4-003 [1, 5 or 10 mg/kg equivalent dose of active compound PRX-002 (−)] at 60 min before spontaneous locomotor activity (sLMA) test.

The rat was placed at the center of test chamber for the 60 min sLMA video recording. 60 min of spontaneous locomotion activity was video recorded and off line analyzed with Animal Behavior Video Tracking Analysis System (Ji Liang Software Technology Co., Ltd., Shanghai, China). Total traveling distance (cm) and duration (sec) of locomotor activity of every 15 min is presented FIGS. 11A and 11B.

Figure 11A:
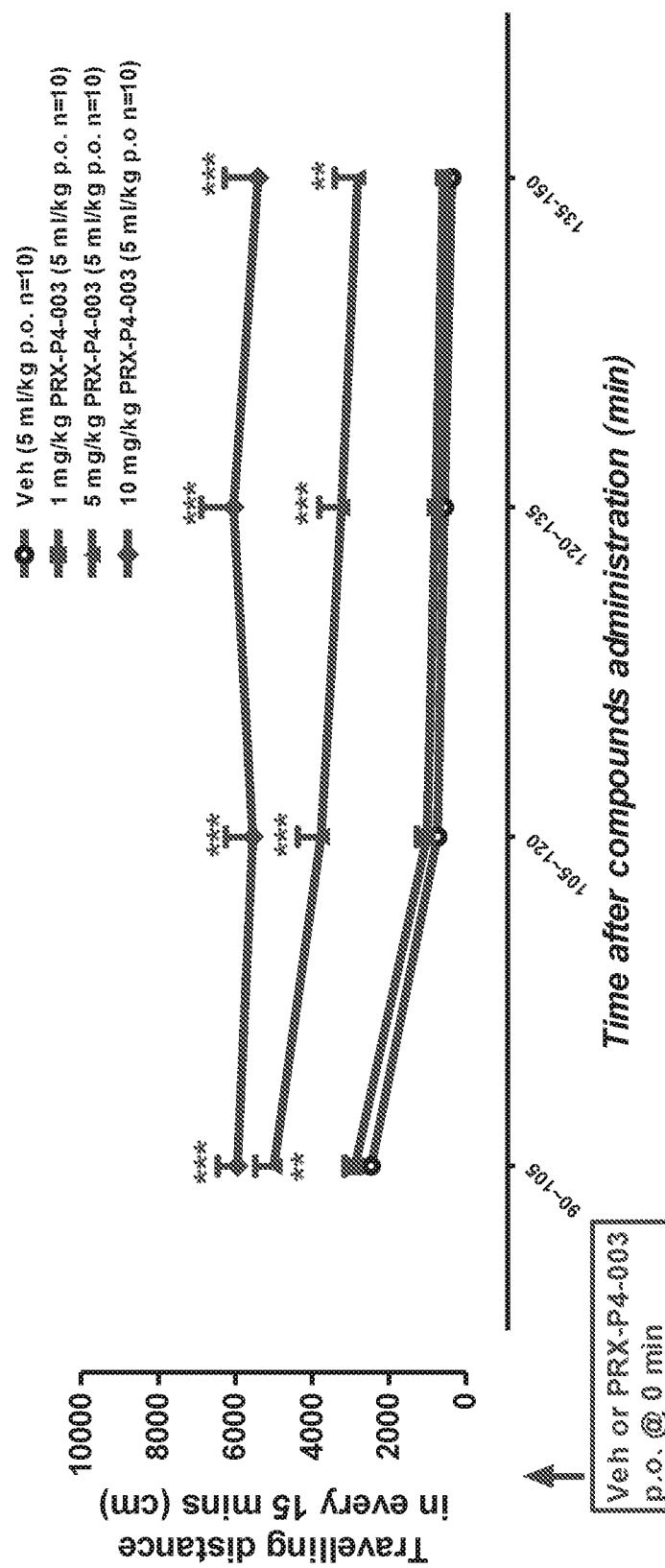
FIGS. 11A and 11B: Total traveling distance (cm, FIG. 11A) and duration (sec, FIG. 11B) of locomotor activity of every 15 min. Data were expressed as Mean±S.E.M. and analyzed with Repeated measures ANOVA followed by Bonferroni test compared to vehicle group. *P<0.05, P<0.01, *P<0.001: vs. Veh group.
Figure 11B:
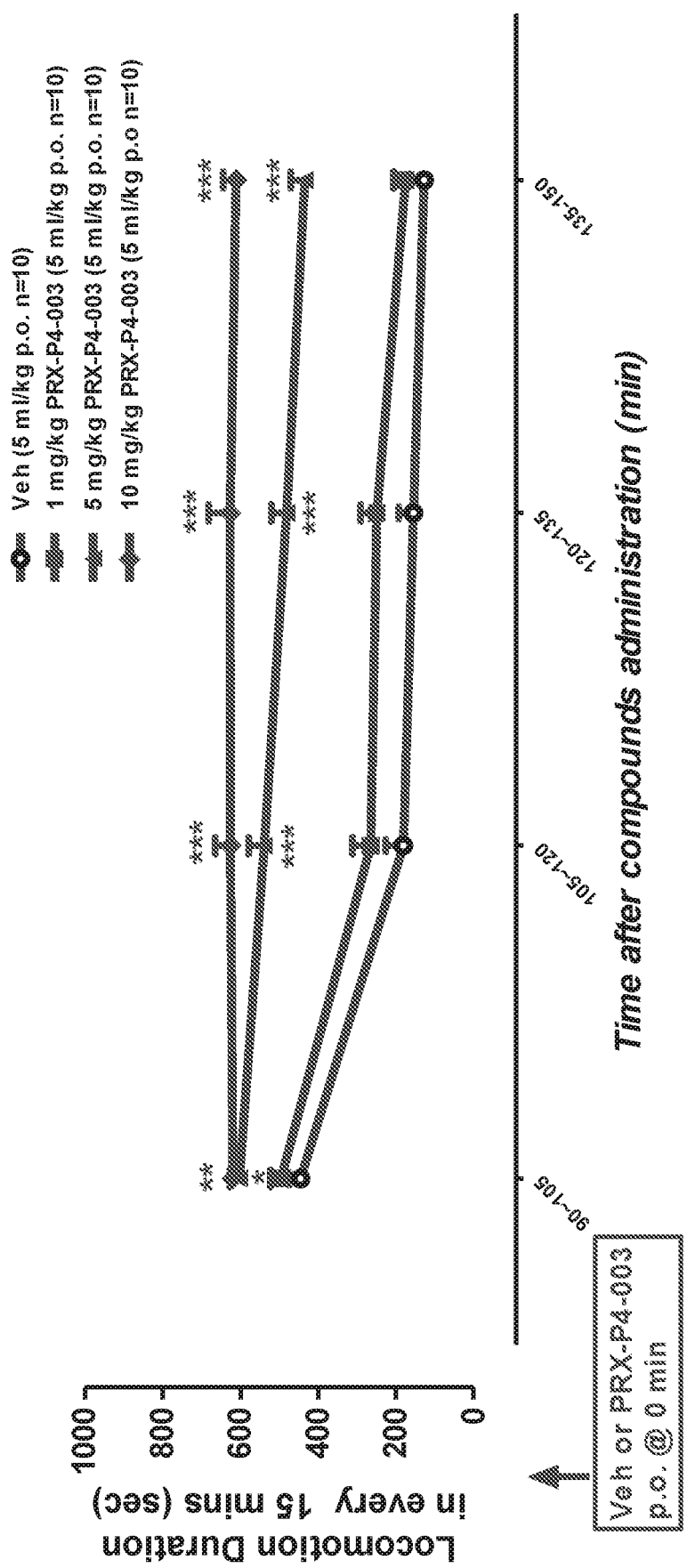

As can be seen in FIGS. 11A and 11B, PRX-P4-003 showed a dose dependent increase in sLMA when given orally.

Example 40B. Pharmacodynamic Response (Spontaneous Locomotor Activity) to PRX-P4-003 by Intravenous Administration Male SD rats were intravenously administered with PRX-002(−) (2 mg/kg) and prodrug PRX-P4-003 [(25.8 mg/kg, equivalent to 10 mg/kg of PRX-002 (−)], and vehicle just before sLMA test.

Vehicle was: 10% PEG 400 (v/v)+30% (v/v) of (50% w/v) Hydroxypropyl-ß-cyclodextrin in water+60% (v/v) sterile water for injection (SWFI): 1 ml/kg volume.

PRX-P4-003 solution was: 25.8 mg/ml PRX-P4-003 (25.8 mg/kg: equivalent to 10 mg/ml active drug, i.v. @volume of 1 ml/kg). 42.3 mg PRX-P4-003 was added to vehicle 1.639 ml, vortexed for 30 min under room temperature to get a uniform suspension solution, suspension solution was continuously stirred during dosage.

The PRX-P4-002(−) solution was: 2 mg/ml PRX-P4-002 (−) (2 mg/kg, i.v.@volume of 1 ml/kg). 4.5 mg PRX-002(−) was added to 2.25 ml Vehicle, vortexed for 30 min under room temperature to get a clear solution, the solution was continuously stirred during dosage.

Rat was placed at the center of test chamber for the 90 min sLMA video recording. (n=3/group).

Figure 12A:
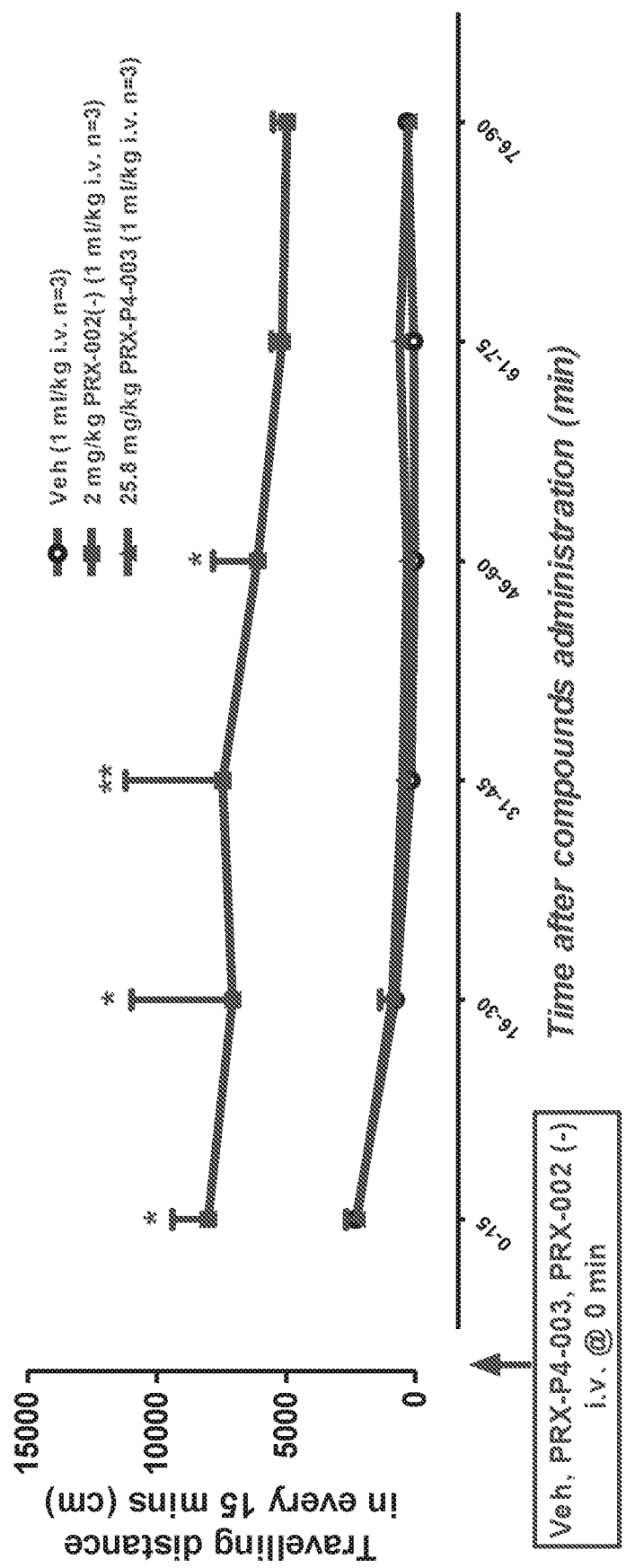
FIGS. 12A and 12B: Total traveling distance (cm, FIG. 12A) and duration (sec, FIG. 12B) of locomotor activity of every 15 min. Data were expressed as Mean±S.E.M. and analyzed with Repeated measures ANOVA followed by Bonferroni test compared to vehicle group. *P<0.05, P<0.01, *P<0.001: vs. Veh group.
Figure 12B:
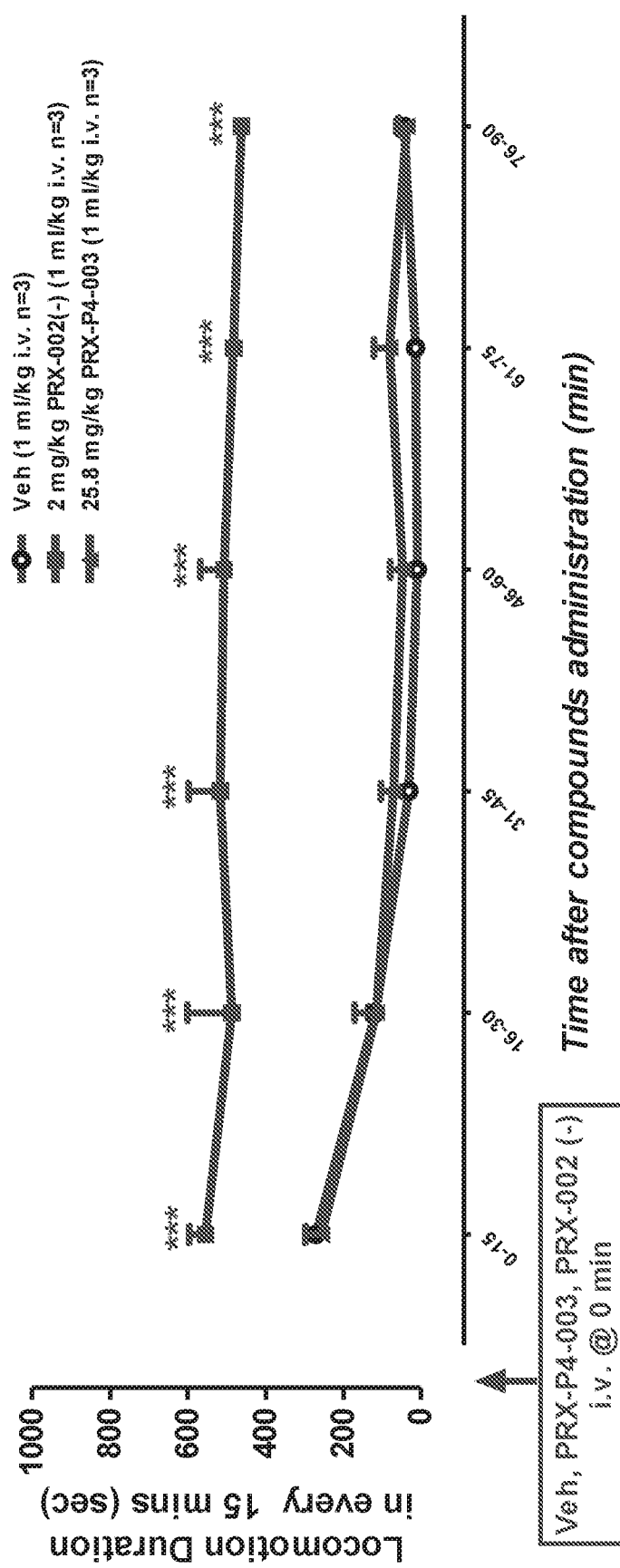

Total traveling distance (cm) and duration (sec) of locomotor activity of every 15 min is presented in FIGS. 12A and 12B. Consistent with the the present disclosures, intravenous PRX-002 (−) significantly increased sLMA but prodrug PRX-P4-003 showed no increase in sLMA (even at a 5 times equivalent dose of active) compared to vehicle, even when given intravenously.

As can be seen in the comparison of the results in Example 40A and Example 40B, the prodrug PRX-P4-003 resulted in higher levels of sLMA activity when administered orally than intravenously. Indeed, while both traveling distance and locomotion duration increased following the oral administration of the prodrug (FIGS. 11A and 11B), intravenous administration resulted in practically no change (in comparison to the administration of the active ingredient itself (PRX-002(−)). Thus, the active drug's availability and impact upon the subject is dependent upon its route of administration of the prodrug.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the disclosure, but instead as merely intended to highlight alternative or additional features that may or may not be utilized in a particular embodiment of the disclosure. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the disclosure to the specific embodiments and examples described herein, but rather to also cover all modification and alternatives coming with the true scope and spirit of the disclosure.

What is claimed is:

1. A prodrug composition comprising at least one conjugate of N-ethyl-3-phenylbicyclo[2.2.1]heptan-2-amine or any of its stereoisomers, wherein the conjugate is a compound selected from the group consisting of:

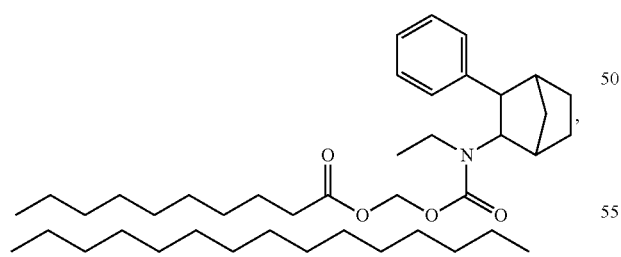

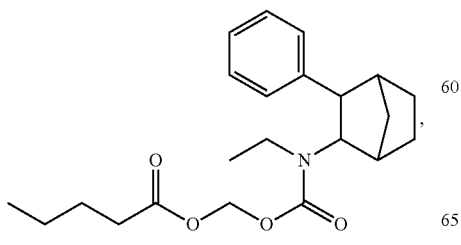

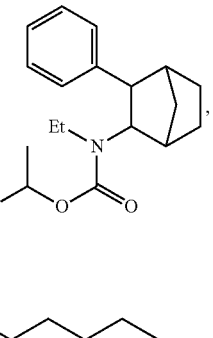

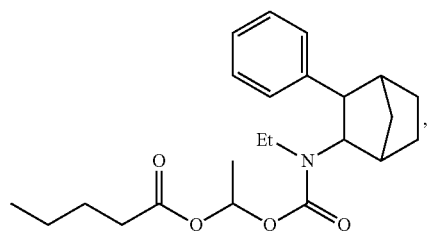

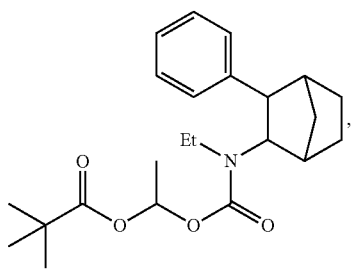

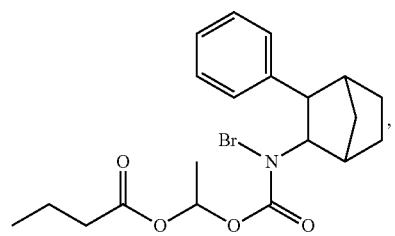

-continued

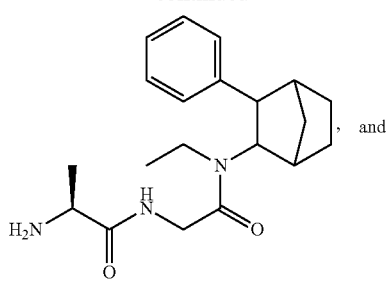, and

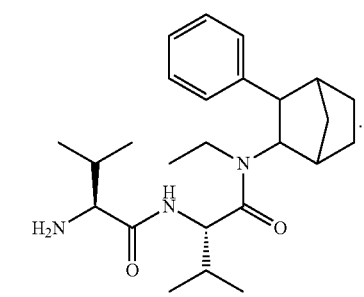

2. The prodrug composition of claim 1, wherein the compound has the structure of:

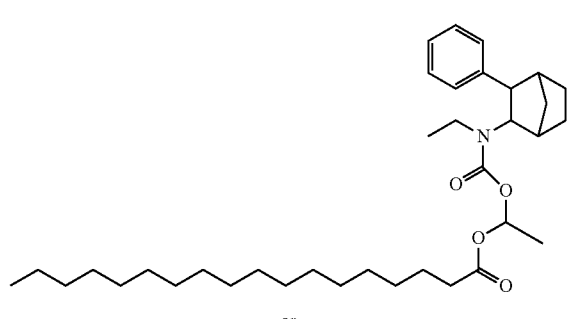

or

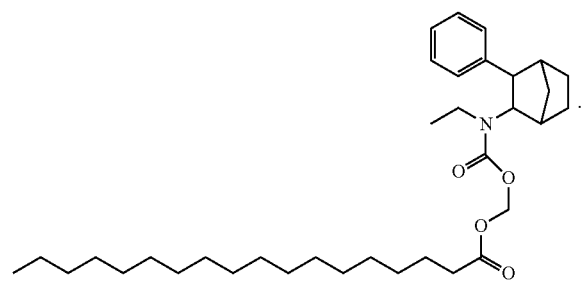

3. The prodrug composition of claim 1, wherein the compound has the structure of:

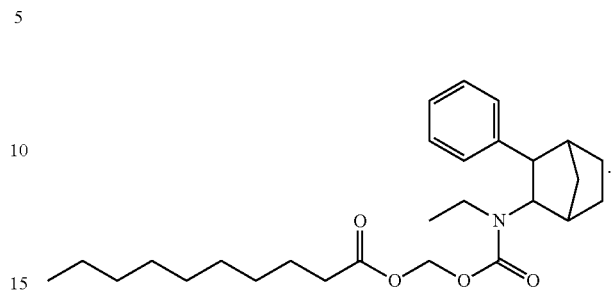

4. The prodrug composition of claim 1, wherein the compound has the structure of:

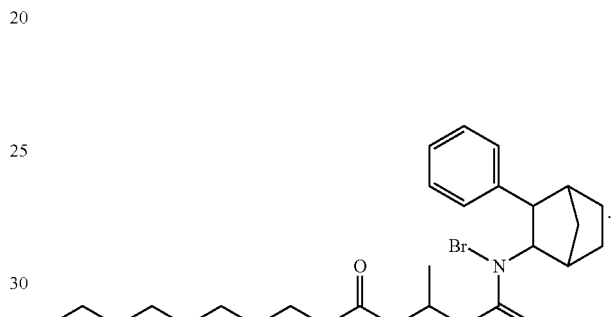

5. The prodrug composition of claim 1, wherein the compound has the structure of:

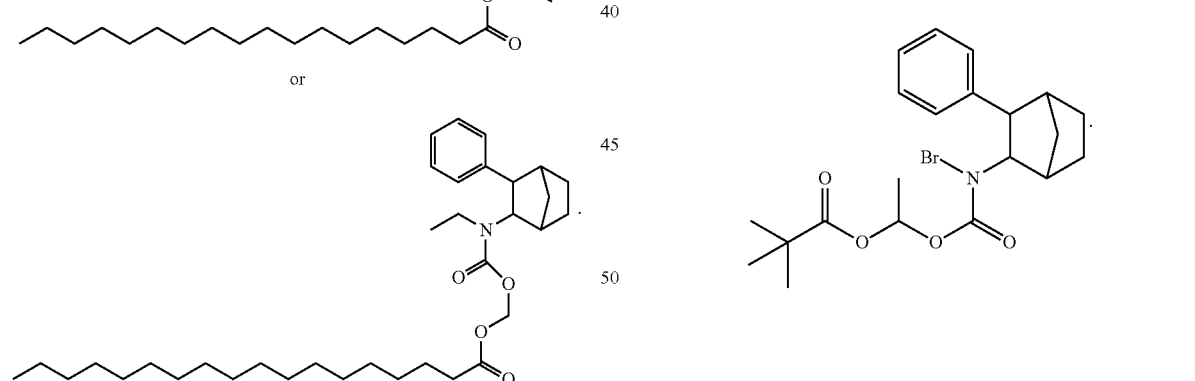

6. The prodrug composition of claim 1, wherein the compound has the structure of:

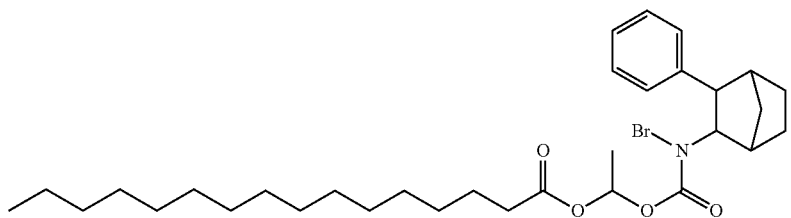

7. The prodrug composition of claim 1, wherein the compound has the structure of:

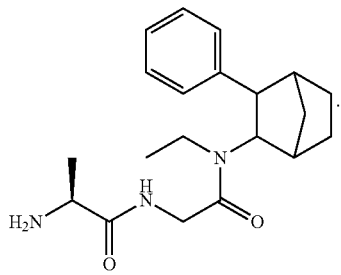 [SMILES: CCN(C(=O)CNC(=O)[C@H](C)N)C1C2CCC(C2)C1c1ccccc1]

8. The prodrug composition of claim 1, wherein the compound has the structure of:

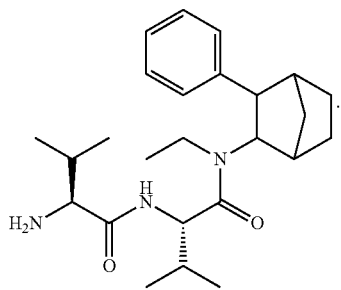 [SMILES: CCN(C(=O)[C@@H](NC(=O)[C@@H](N)C(C)C)C(C)C)C1C2CCC(C2)C1c1ccccc1]

9. The prodrug composition comprising the compound of claim 1, wherein the prodrug composition has an increased plasma or blood concentration of the released N-ethyl-3-phenylbicyclo[2.2.1]heptan-2-amine when administered orally as compared to when it is administered intravenously and when the unconjugated drug is administered in equimolar amounts.

10. The prodrug composition comprising the compound of claim 1, wherein the prodrug composition is in the form comprising a tablet, a capsule, elixir, emulsion solution, suspension solution, or syrup.

11. A method for treating cancer-related fatigue, the method comprising administering an effective amount of the compound of claim 1 to a subject in need thereof.

12. The method of claim 11, wherein the prodrug composition provides reduced ability to abuse the drug composition when compared to the unconjugated N-ethyl-3-phenylbicyclo[2.2.1]heptan-2-amine.

13. The method of claim 12, wherein the subject is mammalian.

14. A method for treating Alzheimer's disease, Parkinson's disease, major depressive disorder, or attention deficit hyperactivity disorder, the method comprising administering an effective amount of the compound of claim 1 to a subject in need thereof.

\* \* \* \* \*